(12) United States Patent
Ohler et al.

(10) Patent No.: US 11,193,078 B2
(45) Date of Patent: Dec. 7, 2021

(54) OLEFINS AND METHODS FOR MAKING THE SAME

(71) Applicant: Amyris, Inc., Emeryville, CA (US)

(72) Inventors: Nicholas Ohler, Emeryville, CA (US); Karl Fisher, Emeryville, CA (US); Jin Ki Hong, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 63 days.

(21) Appl. No.: 16/389,690

(22) Filed: Apr. 19, 2019

(65) Prior Publication Data
US 2019/0249101 A1    Aug. 15, 2019

Related U.S. Application Data

(62) Division of application No. 14/112,235, filed as application No. PCT/US2012/024922 on Feb. 13, 2012, now Pat. No. 10,294,439.

(Continued)

(51) Int. Cl.
| | |
|---|---|
| *C10L 1/04* | (2006.01) |
| *C10M 105/02* | (2006.01) |
| *C10M 105/04* | (2006.01) |
| *C10M 107/14* | (2006.01) |
| *C07C 5/05* | (2006.01) |
| *C07C 5/03* | (2006.01) |

(52) U.S. Cl.
CPC ............ *C10M 105/02* (2013.01); *C07C 5/03* (2013.01); *C07C 5/05* (2013.01); *C10L 1/04* (2013.01); *C10M 105/04* (2013.01); *C10M 107/14* (2013.01); *C07C 2521/04* (2013.01); *C07C 2523/44* (2013.01); *C07C 2523/75* (2013.01); *C10M 2203/003* (2013.01); *C10M 2203/022* (2013.01); *C10M 2203/024* (2013.01); *C10M 2203/0206* (2013.01); *C10M 2205/083* (2013.01); *Y02P 20/582* (2015.11)

(58) Field of Classification Search
None
See application file for complete search history.

(56) References Cited

U.S. PATENT DOCUMENTS

| | | |
|---|---|---|
| 2,417,220 A | 3/1947 | Lee et al. |
| 2,674,634 A | 4/1954 | Greensfelder |

(Continued)

FOREIGN PATENT DOCUMENTS

| | | |
|---|---|---|
| WO | WO 2007/139924 | 12/2007 |
| WO | WO 2010/027464 | 3/2010 |

(Continued)

OTHER PUBLICATIONS

Kim, "Biosynthetic Studies of 4,8-Dimethyldecanal, the Aggregation Pheromone of the Red Flour Beetle, *Tribolium castaneum*", Thesis (Ph. D. in Agricultural Science)—University of Tsukuba, (A), No. 3755, Mar. 25, 2005. (Year: 2005).*

(Continued)

*Primary Examiner* — Philip Y Louie
(74) *Attorney, Agent, or Firm* — Squire Patton Boggs (US) LLP

(57) ABSTRACT

Provided herein are olefinic feedstocks derived from conjugated hydrocarbon terpenes (e.g., $C_{10}$-$C_{30}$ terpenes), methods for making the same, and methods for their use.

5 Claims, 9 Drawing Sheets

Related U.S. Application Data

(60) Provisional application No. 61/524,143, filed on Aug. 16, 2011, provisional application No. 61/502,252, filed on Jun. 28, 2011, provisional application No. 61/493,316, filed on Jun. 3, 2011, provisional application No. 61/482,122, filed on May 3, 2011, provisional application No. 61/475,221, filed on Apr. 13, 2011, provisional application No. 61/475,217, filed on Apr. 13, 2011.

(56) References Cited

U.S. PATENT DOCUMENTS

| | | | |
|---|---|---|---|
| 3,702,348 A | | 11/1972 | Nehring et al. |
| 3,987,121 A | * | 10/1976 | Koppel ............... C07C 7/06 203/64 |
| 4,310,714 A | * | 1/1982 | Pavlin ............... C07C 5/03 585/275 |
| 4,546,110 A | | 10/1985 | Dawson et al. |
| 4,590,319 A | | 5/1986 | Imaki et al. |
| 5,151,172 A | | 9/1992 | Kukes et al. |
| 5,208,405 A | | 5/1993 | Cheung et al. |
| 5,378,767 A | | 1/1995 | Massie |
| 5,475,173 A | | 12/1995 | Cheung et al. |
| 5,723,709 A | * | 3/1998 | Phillips, Jr. ............... C07C 2/02 585/10 |
| 6,403,844 B1 | | 6/2002 | Zhang et al. |
| 7,399,323 B2 | | 7/2008 | Renninger et al. |
| 7,592,295 B1 | | 9/2009 | Fisher et al. |
| 7,659,097 B2 | | 2/2010 | Renninger et al. |
| 8,257,957 B2 | | 9/2012 | Keasling et al. |
| 8,519,204 B2 | | 8/2013 | Ohler et al. |
| 2002/0091214 A1 | * | 7/2002 | Waanders ............ C07C 407/006 526/229 |
| 2008/0274523 A1 | | 11/2008 | Renninger et al. |
| 2009/0137014 A1 | | 5/2009 | Tsuruta et al. |
| 2010/0267971 A1 | | 10/2010 | Ohler et al. |
| 2011/0287988 A1 | | 11/2011 | Fisher et al. |
| 2013/0123379 A1 | | 5/2013 | Mcphee |
| 2013/0252295 A1 | | 9/2013 | Renninger et al. |

FOREIGN PATENT DOCUMENTS

| | | |
|---|---|---|
| WO | WO 2010/042208 | 4/2010 |
| WO | WO 2010/115097 | 10/2010 |
| WO | WO 2012/141784 | 10/2012 |
| WO | WO 2013/028307 | 2/2013 |

OTHER PUBLICATIONS

Lukasik et al., "The influence of hydrogen pressure on the heterogeneous hydrogenation of β-myrcene in a CO2-expanded liquid", The Journal of Supercritical Fluids, ScienceDirect, 2010, p. 46-52. (Year: 2010).*
Xu et al., "Occurrence of C25 highly branched isoprenoids (HBIs) in Florida Bay: Paleoenvironmental indicators of diatom-derived organic matter inputs", Organic Geochemistry, vol. 37, Issue 7, Jul. 2006, pp. 847-859. (Year: 2006).*
Belt et al., "A novel chemical fossil of palaeo sea ice: IP25", Organic Geochemistry, vol. 38, Issue 1, Jan. 2007, pp. 16-27. (Year: 2007).*
U.S. Appl. No. 61/475,217, filed Apr. 13, 2011, Ohler et al.
U.S. Appl. No. 61/475,221, filed Apr. 13, 2011, Tirmizi et al.
U.S. Appl. No. 61/482,122, filed May 3, 2011, Ohler.
U.S. Appl. No. 61/493,316, filed Jun. 3, 2011, Ohler et al.
U.S. Appl. No. 61/502,252, filed Jun. 28, 2011, Fisher et al.
U.S. Appl. No. 61/524,143, filed Aug. 16, 2011, Fisher et al.
International Search Report for PCT/US2012/024922, dated Jul. 12, 2012, 3 pages.
Examination report dated Feb. 13, 2018 for the EP Application No. 12708189.1; 7 pages.
"CRC Handbook of Chemistry and Physics", 95th Edition, Internet version (http://www.hbcpnetbase.com/); Haynes, W.D., ed.; 2015: Ch.3, pp. 216 and 217.
Anet E.F.L.J., "Synthesis of (E,Z)-a- , and (Z)-β-farnesene", Aust. J. Chem. 23(10), 1970, pp. 2101-2108.
Braun et al., "Hexahydro-farnesal and Nor hexahydro-farnesal", Beriche Der Deutsche Chemische Gesellschaft, Jan. 1, 1929, vol. 62, No. 6, pp. 1489-1491, with English translation.
Dieguez et al., "Weakening C—O Bonds: Ti(I11), a New Regent for Alcohol Deoxygenation and Carbonyl Coupling Olefination," J. Am. Chem. Soc., vol. 132, pp. 254-259 (2010).
Frolov et al., "Highly active supported palladium catalysts for selective hydrogenation of conjugated dienes into olefins," Reaction Kinetics and Catalysis Letters, vol. 25, Nos. 3-4, pp. 319-322 (1984) book 4 pgs attached.
Hernandez-Torres et al., "Stereocontrolled generation of the (2R) chroman core of vitamin E: total sysnthesis of (2R,4ORS,8'RS)-alpha-tocopherol", Organic Letters, vol. 11, No. 21, 2009, pp. 4930-4933.
Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem. 55 (6), pp. 1854-1856 (1990).
Smith, J. Am. Chem. Soc. 65, 1943, pp. 745-750.
Speziali et al., "Selective hydrogenation of myrcene catalyzed by complexes of ruthenium, chromium, iridium and rhodium", Journal of Molecular Catalysis A: Chemical, Elsevier, Amsterdam, NL, Sep. 14, 2005, vol. 239, No. 1-2, pp. 10-14.
Tungler et al., "Reduction of Dienes and Polyenes," in The Chemistry of Dienes and Polyenes, vol. 2 (ed. Z. Rappoport), John Wiley & Sons, Ltd, Chichester, UK, (2003).

* cited by examiner

OLEFINS AND METHODS FOR MAKING THE SAME

CROSS-REFERENCE TO RELATED APPLICATIONS

This application is a divisional application of U.S. application Ser. No. 14/112,235 filed Jan. 14, 2014, which is a national phase application of PCT/US2012/024922 filed Feb. 13, 2012, which claims the benefit of and priority to U.S. provisional patent application 61/475,217 filed Apr. 13, 2011, U.S. provisional patent application 61/475,221 filed Apr. 13, 2011, U.S. provisional patent application 61/482,122 filed May 3, 2011, U.S. provisional patent application 61/493,316 filed Jun. 3, 2011, U.S. provisional patent application 61/502,252 filed Jun. 28, 2011, and U.S. provisional patent application 61/524,143 filed Aug. 16, 2011 each of which is incorporated by reference herein in its entirety as if put forth fully below.

STATEMENT REGARDING FEDERALLY FUNDED RESEARCH

Some of the work described herein was funded by Award No. DE-EE0002869 awarded by the U.S. Department of Energy. Accordingly, the Government may have rights to some embodiments of this invention.

FIELD

Described herein are feedstocks derived from an alkene comprising a conjugated diene moiety and one or more additional olefinic bonds, methods of making the feedstocks and methods of their use. The feedstocks described herein may be used to replace or to supplement olefinic feedstocks derived from fossil fuels. In some variations, the alkene used to make the feedstocks is derived from a renewable carbon source.

BACKGROUND

Olefins can be used as raw materials or feedstocks in a variety of industrial processes, such as in the production of plastics, fatty acids, detergents, oils, and the like. Conventional olefinic feedstocks are often derived from petroleum or petroleum products. In some cases, olefins are derived from cracking of petroleum as hydrocarbon streams that are mixtures of olefins, saturated hydrocarbons, and oxygenates. Alternatively, mixtures of alpha olefins and internal olefins having a broad range of carbon numbers are produced by catalytic oligomerization of ethylene or propylene (either of which is typically derived from petroleum). In each case, to obtain an olefin having a desired carbon number or range of carbon numbers, substantial downstream processing can be required to isolate a desired product from a mixture, e.g. chemical separation and/or distillation fractionation. The degree and presence of branching in olefins derived by cracking or through oligomerization of ethylene or propylene is highly catalyst dependent and can vary from batch to batch in some cases. Olefins produced from petroleum can contain sulfur and aromatic compounds, which are environmentally undesirably impurities.

There is a need for renewable olefinic feedstocks that are not derived from fossil fuels. Furthermore, there is a need for alternate olefinic feedstocks, e.g. olefinic feedstocks that include no detectable amounts of sulfur or aromatic compounds. In addition, there is a need for methylated olefinic feedstocks, e.g. methylated olefinic feedstocks in which the methylation position is controlled.

SUMMARY

In certain embodiments, provided herein are olefinic feedstocks comprising partially hydrogenated conjugated alkenes, methods for making the same, methods of using the olefinic feedstocks described herein in manufacture, and products produced by the methods of use. Advantageously, certain methods provided herein are capable of selectively hydrogenating particular olefinic bond(s) of a conjugated alkene to yield mono-olefinic feedstocks. In certain embodiments, the olefinic (e.g., mono-olefinic) feedstocks comprise little or no contaminants.

In one aspect, provided herein are methods of making olefinic feedstocks. In certain embodiments, the olefinic feedstocks are made from a conjugated alkene comprising at least one conjugated diene and at least one additional olefinic bond. According to the methods, in a first stage, the conjugated alkene is reacted with hydrogen in the presence of a first catalyst under conditions suitable to preferentially hydrogenate at least one of the olefinic bonds in the conjugated diene to produce a partially hydrogenated olefinic intermediate in a first stage. For the first stage, catalysts and conditions, such as catalyst loading, catalysis temperatures and catalysis pressure, are described in detail herein. In a second stage, a partially hydrogenated intermediate is reacted with hydrogen in the presence of a second catalyst under conditions suitable for making the desired olefinic feedstock. For the second stage, catalysts and conditions, such as catalyst loading, catalysis temperatures and catalysis pressure, and resulting olefinic feedstocks are described herein. In certain embodiments, the first catalyst and the second catalyst are the same. In other embodiments, the first catalyst and the second catalyst are different.

The conjugated alkene can be any conjugated alkene apparent to one of skill in the art. In certain embodiments, the conjugated alkene comprises the conjugated diene and at least one additional olefinic bond. In certain embodiments, the conjugated alkene comprises the conjugated diene and at least two additional olefinic bonds. In certain embodiments, the conjugated alkene comprises the conjugated diene and at least three additional olefinic bonds. In certain embodiments, the conjugated alkene comprises an alpha-olefinic bond. In certain embodiments, the conjugated diene comprises an alpha-olefinic bond. In certain embodiments, the conjugated alkene is a $C_{10}$-$C_{30}$ alkene. In certain embodiments, the conjugated alkene is a terpene. Exemplary terpenes include myrcene, ocimene and farnesene. In exemplary embodiments, the conjugated terpene is β-farnesene and/or α-farnesene.

In some embodiments, methods described herein comprise selectively hydrogenating a conjugated terpene comprising at least three olefinic bonds wherein two of the at least three olefinic bonds form a conjugated diene, to make a composition comprising at least about 65% mono-olefinic species (e.g., at least about 65%, at least about 70%, at least about 75%, or at least about 80%). In some embodiments, methods described herein comprise selectively hydrogenating a conjugated terpene comprising at least three olefinic bonds wherein two of the at least three olefinic bonds form a conjugated diene, to make a composition comprising at least about 50% mono-olefinic species and at most about 10% di-olefinic species. In some variations, the methods are capable of producing a composition comprising at least about 50%, at least about 60%, at least about 70%, or at least about 80% mono-olefin and at most about 5% di-olefin. In some variations, the methods are capable of producing a composition comprising at least about 50%, at least about 60%, at least about 70%, or at least about 80% mono-olefin and at most about 3%, at most about 2%, at most about 1%, or at most about 0.5% di-olefin. In certain embodiments, the compositions produced by selective hydrogenation of conjugated terpenes comprise about 1% or less, about 0.5% or less, or about 0.1% or less conjugated diene.

In advantageous embodiments, the conjugated alkene (e.g., terpene) is produced by one or more microorganisms. For example, the conjugated alkane can be produced by a bioengineered microorganism, i.e. a microorganism engineered to produce the conjugated alkane starting material, or a precursor thereof. In particular embodiments, the microorganism produces the conjugated alkane, or a precursor thereof, from a renewable carbon source. In such embodiments, the present methods provide renewable sources for the resulting olefinic feedstocks.

In certain embodiments, the resulting olefinic feedstocks comprise a substantial amount of a mono-olefinic partially hydrogenated conjugated alkene. In certain embodiments, the feedstocks comprise a limited amount of the corresponding alkane. In certain embodiments, the feedstocks comprise a limited amount of corresponding species having two or more double bonds. In certain embodiments, the feedstocks comprise a limited amount of the corresponding conjugated alkene. In certain embodiments, the resulting olefinic feedstocks are rich in mono-olefinic species. In certain embodiments, the resulting olefinic feedstocks are rich in mono-olefinic species and contain limited amounts of corresponding di-olefinic species.

In certain embodiments, the olefinic feedstocks comprise at least about 60% mono-olefin, at least about 65% mono-olefin, at least about 70% mono-olefin, at least about 75% mono-olefin, at least about 80% mono-olefin or at least about 85% mono-olefin. In certain embodiments, the olefinic feedstocks comprise less than about 25% alkane, less than about 20% alkane, less than about 15% alkane or less than about 10% alkane. In certain embodiments, the olefinic feedstocks comprise about 15% or less di-olefinic species, e.g., about 10% or less, about 9% or less, about 8% or less, about 7% or less, about 6% or less, about 5% or less, about 4% or less, about 3% or less, about 2% or less, or about 1% or less di-olefins. In certain embodiments, di-olefins that are present are predominantly unconjugated dienes. In certain embodiments, the olefinic feedstocks comprise less than about 25% conjugated alkene, less than about 20% conjugated alkene, less than about 15% conjugated alkene, less than about 10% conjugated alkene, less than about 5% conjugated alkene, or less than about 2% conjugated alkene.

In certain embodiments, the olefinic feedstocks have little or no sulfur or aromatic content. In certain embodiments, the olefinic feedstocks have little or no sulfur content. In certain embodiments, the olefinic feedstocks have little or no aromatic content. In certain embodiments, the olefinic feedstocks have little or no sulfur content and little or no aromatic content. Exemplary amounts of sulfur and/or aromatic content are provided herein.

In another aspect, provided herein are partially hydrogenated olefinic feedstocks comprising a substantial amount of a partially hydrogenated conjugated alkene and a limited amount of the corresponding alkane. In certain embodiments, the partially hydrogenated olefinic feedstocks comprise a limited amount of the conjugated alkene starting material. In another aspect, provided herein are partially hydrogenated olefinic feedstocks comprising a substantial amount of mono-olefinic species and a limited amount of di-olefinic species. In certain embodiments, provided herein are partially hydrogenated olefinic feedstocks comprising a substantial amount of mono-olefinic species, a limited amount of corresponding alkane and little or sulfur or aromatic content. In certain embodiments, provided herein are partially hydrogenated olefinic feedstocks comprising a substantial amount of mono-olefinic species, a limited amount of corresponding di-olefinic species and little or no sulfur or aromatic content. In particular embodiments, the feedstocks are prepared according to the methods described herein.

The olefinic feedstocks described herein may comprise one or more methylated alkenes (e.g. one or more of methylated mono-alkenes, methylated di-alkenes, methylated tri-alkenes, and methylated tetra-alkenes, where the number of carbon atoms in the base alkene for any of the above corresponds to the number of carbon atoms in the main chain of the hydrocarbon terpene used to make the feedstock).

An olefinic feedstock described herein that comprises partially hydrogenated conjugated alkene can exhibit a narrow molecular weight distribution as produced (e.g. a distribution spanning over about 2-10 amu), without requiring a separation process such as distillation. An olefinic feedstock described herein that is derived from more than one conjugated alkene can exhibit a broader but predicted molecular weight distribution as produced, again without the need for a separation process.

In certain embodiments, the olefinic feedstocks provided herein are mixed olefinic feedstocks. The olefinic feedstocks provided herein can further comprise, for example, a second partially hydrogenated conjugated alkene. In certain embodiments, the olefinic feedstocks provided herein may further comprise a linear alpha olefin, a branched alpha olefin, a linear internal olefin or a branched internal olefin.

In a particular aspect, provided are compositions prepared according to any of the methods described herein.

The olefinic feedstocks can be used for any purpose apparent to one of skill in the art. In certain embodiments, the olefinic feedstocks can be used for the preparation of a plastic, a detergent, a lubricant, an oil, or another product desired by one of skill in the art. In certain embodiments, an olefinic feedstock provided herein can supplement a conventional olefinic feedstock derived from fossil fuel in any process deemed suitable by one of skill in the art. In certain embodiments, the olefinic feedstock can replace a conventional olefinic feedstock derived from fossil fuel deemed suitable by one of skill in the art. In certain embodiments, the olefinic feedstocks described herein (e.g., a feedstock rich in mono-olefinic species) can be polymerized, oligomerized, copolymerized, or co-oligomerized to make, for example, an oil or lubricant. In certain embodiments, provided herein are products (e.g. plastics, oils, or alcohols) produced by an industrial process (e.g., oligomerization, polymerization, hydroformylation, carbonylation, and the like) that utilizes a partially hydrogenated $C_{10}$-$C_{30}$ hydrocarbon terpene as a monomer or reactant. In one embodiment, provided herein are methods that comprise using an olefinic feedstock comprising a partially hydrogenated $C_{10}$-$C_{30}$ hydrocarbon terpene as a monomer or reactant in an industrial oligomerization, polymerization, hydroformylation, or carbonylation process.

BRIEF DESCRIPTION OF THE DRAWINGS

FIG. 5A shows % mono-olefin vs. % di-olefin. FIG. 5B shows % di-olefin vs. % farnesane. FIG. 5C shows % mono-olefin vs. % farnesane. FIG. 5D shows % mono-olefin vs. second stage hydrogenation temperature (° C.). FIG. 5E shows % farnesane vs. second stage hydrogenation temperature (° C.). FIG. 5F shows % di-olefin vs. second stage hydrogenation temperature (° C.).

DETAILED DESCRIPTION

Definitions

Figure 1:
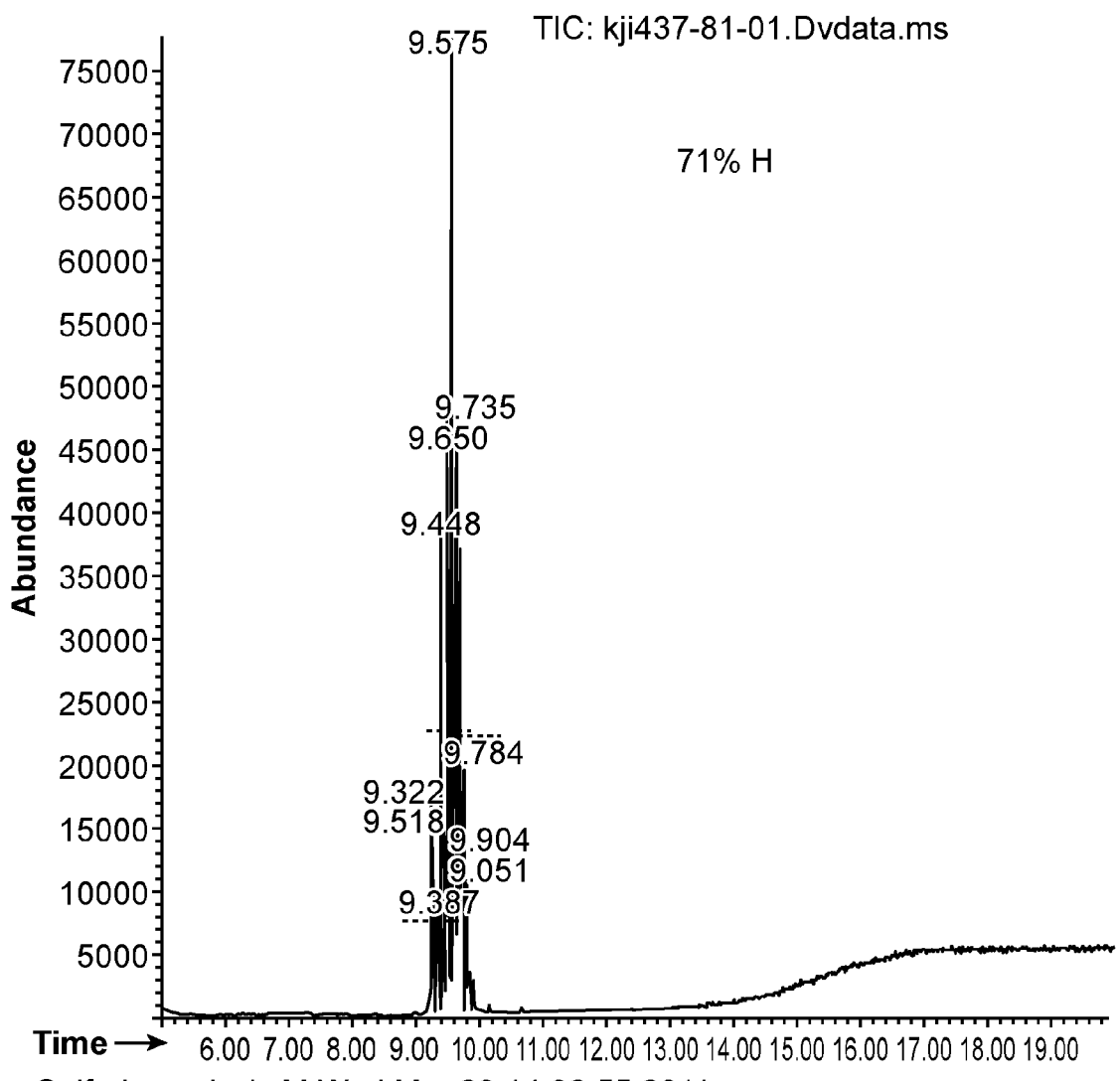
FIG. 1 provides a GC-MS spectrum of β-farnesene that is 71% hydrogenated.

"A conjugated alkene" as used herein encompasses an alkene (which may by linear or branched, acyclic or cyclic) comprising at least one conjugated diene moiety. It should be noted that the conjugated diene may have any stereochemistry (e.g., cis or trans) and the conjugated diene may be part of a longer conjugated segment of the alkene, e.g., the conjugated diene moiety may be part of a conjugated triene.

"Terpene" as used herein is a compound that is capable of being derived from isopentyl pyrophosphate (IPP) or dimethylallyl pyrophosphate (DMAPP), and the term terpene encompasses hemiterpenes, monoterpenes, sesquiterpenes, diterpenes, sesterterpenes, triterpenes, tetraterpenes and polyterpenes. A hydrocarbon terpene contains only hydrogen and carbon atoms and no heteroatoms such as oxygen, and in some embodiments has the general formula $(C_5H_8)_n$, where n is 1 or greater. A "conjugated terpene" or "conjugated hydrocarbon terpene" as used herein refers to a terpene comprising at least one conjugated diene moiety. It should be noted that the conjugated diene moiety of a conjugated terpene may have any stereochemistry (e.g., cis or trans) and may be part of a longer conjugated segment of a terpene, e.g., the conjugated diene moiety may be part of a conjugated triene moiety. It should be understood that hydrocarbon terpenes as used herein also encompasses monoterpenoids, sesquiterpenoids, diterpenoids, triterpenoids, tetraterpenoids and polyterpenoids that exhibit the same carbon skeleton as the corresponding terpene but have either fewer or additional hydrogen atoms than the corresponding terpene, e.g., terpenoids having 2 fewer, 4 fewer, or 6 fewer hydrogen atoms than the corresponding terpene, or terpenoids having 2 additional, 4 additional or 6 additional hydrogen atoms than the corresponding terpene. Some non-limiting examples of conjugated hydrocarbon terpenes include isoprene, myrcene, α-ocimene, β-ocimene, α-farnesene, β-farnesene, β-springene, geranylfarnesene, neophytadiene, cis-phyta-1,3-diene, trans-phyta-1,3-diene, isodehydrosqualene, isosqualane precursor I, and isosqualane precursor II.

The terms terpene and isoprenoids are used interchangeably herein, and are a large and varied class of organic molecules that can be produced by a wide variety of plants and some insects. Some terpenes or isoprenoid compounds can also be made from organic compounds such as sugars by microorganisms, including bioengineered microorganisms. Because terpenes or isoprenoid compounds can be obtained from various renewable sources, they are useful monomers for making eco-friendly and renewable base oils. In certain embodiments, the conjugated hydrocarbon terpenes as described herein are derived from microorganisms using a renewable carbon source, such as a sugar.

"Isoprene" refers to a compound having the following structure:

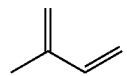

or a stereoisomer thereof.

"Myrcene" refers to a compound having the following structure:

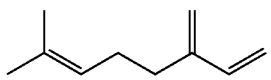

or a stereoisomer thereof.

"Ocimene" refers to α-ocimene, β-ocimene or a mixture thereof.

"α-ocimene" refers to a compound having the following formula:

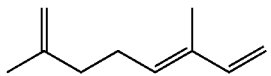

or a stereoisomer thereof.

"β-ocimene" refers to a compound having the following formula:

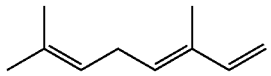

or a stereoisomer thereof.

"Farnesene" as used herein refers to α-farnesene, β-farnesene or a mixture thereof.

"α-Farnesene" refers to a compound having the following structure:

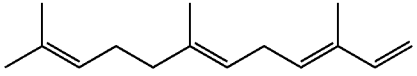

or a stereoisomer (e.g., s-cis isomer) thereof. In some embodiments, α-farnesene comprises a substantially pure stereoisomer of α-farnesene. In some embodiments, α-farnesene comprises a mixture of stereoisomers, such as s-cis and s-trans isomers. In some embodiments, the amount of each of the stereoisomers in an α-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. % or from about 20 wt. % to about 80 wt. %, based on the total weight of the α-farnesene mixture of stereoisomers.

"β-farnesene" refers to a compound having the following structure:

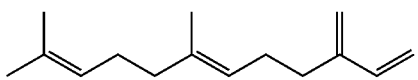

or a stereoisomer thereof. In some embodiments, β-farnesene comprises a substantially pure stereoisomer of β-farnesene. Substantially pure β-farnesene refers to compositions comprising at least 80%, at least 90%, at least 95%, at least 97%, at least 98% or at least 99% β-farnesene by weight, based on total weight of the farnesene. In other embodiments, β-farnesene comprises a mixture of stereoisomers, such as s-cis and s-trans isomers. In some embodiments, the amount of each of the stereoisomers in a β-farnesene mixture is independently from about 0.1 wt. % to about 99.9 wt. %, from about 0.5 wt. % to about 99.5 wt. %, from about 1 wt. % to about 99 wt. %, from about 5 wt. % to about 95 wt. %, from about 10 wt. % to about 90 wt. %, or from about 20 wt. % to about 80 wt. %, based on the total weight of the β-farnesene mixture of stereoisomers.

"Farnesane" refers to a compound having the following structure:

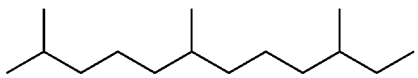

or a stereoisomer thereof.

β-springene (or springene) refers to a compound having the following structure:

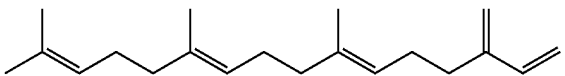 [SMILES: C=CC(=C)CC/C=C(\C)CC/C=C(\C)CCC=C(C)C]

or a stereoisomer thereof.

Neophytadiene refers to a compound having the following structure:

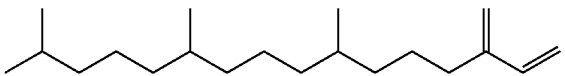 [SMILES: C=CC(=C)CCCC(C)CCCC(C)CCCC(C)C]

or a stereoisomer thereof.

Trans-phyta-1,3-diene refers to a compound having the following structure:

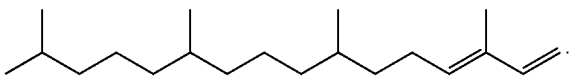 [SMILES: C=C/C(C)=C/CCC(C)CCCC(C)CCCC(C)C ; "."]

Cis-phyta-1,3-diene refers to a compound having the following structure:

"Squalene" refers to a compound having the following structure:

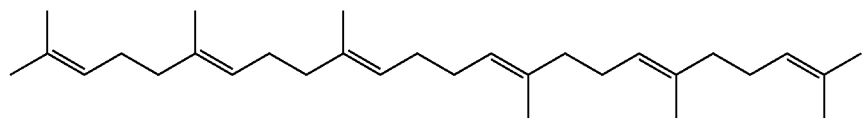 [SMILES: CC(C)=CCC/C(C)=C/CC/C(C)=C/CC/C=C(\C)CC/C=C(\C)CCC=C(C)C]

or a stereoisomer thereof.

As used herein, "isodehydrosqualene" refers to a compound having the following structure:

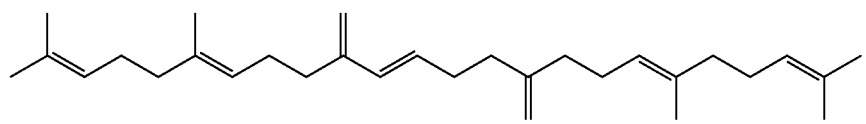 [SMILES: C=C(/C=C/CCC(=C)CC/C=C(\C)CCC=C(C)C)CC/C=C(\C)CCC=C(C)C]

or a stereoisomer thereof.

As used herein, "isosqualane precursor I" or 2,6,18,22-tetramethyl-10-methylene-14-vinyltricosa-2,6,11,17,21-pentaene refers to a compound having the following structure:

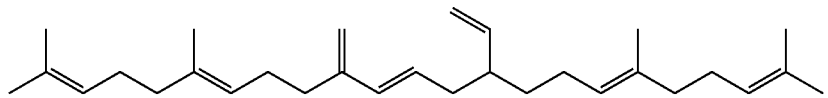 [SMILES: C=CC(C/C=C/C(=C)CC/C=C(\C)CCC=C(C)C)CC/C=C(\C)CCC=C(C)C]

or a stereoisomer thereof.

As used herein, "isosqualane precursor II" or 2,6,14,18,22-pentamethyl-10-vinyltricosa-2,6,10,14,17,21-pentaene refers to a compound having the following structure:

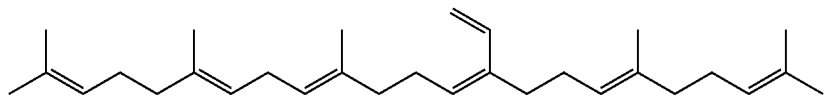 [SMILES: C=C/C(=C\CC/C(C)=C/C/C=C(\C)CCC=C(C)C)CC/C=C(\C)CCC=C(C)C]

or a stereoisomer thereof.

Geranylfarnesene refers to a compound having the following structure:

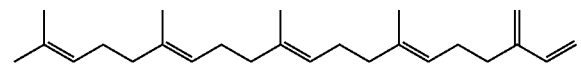 [SMILES: C=CC(=C)CC/C=C(\C)CC/C=C(\C)CC/C=C(\C)CCC=C(C)C]

or a stereoisomer thereof.

"Hydrogenated myrcene" refers to a myrcene molecule in which at least one carbon-carbon double bond is hydrogenated. Hydrogenated myrcene encompasses myrcene in which one, two, or three double bonds are hydrogenated, and any mixtures thereof. Partially hydrogenated myrcene refers to a myrcene molecule in which only one or two double bonds have been hydrogenated, and also refers to a hydrogenated myrcene sample in which at least about 5% of the carbon-carbon double bonds remain unsaturated. A sample of partially hydrogenated myrcene may comprise dihydromyrcene, tetrahydromyrcene, hexahydromyrcene, or any combination thereof. In some cases, a partially hydrogenated myrcene sample comprises myrcene in addition to one or more of dihydromyrcene, tetrahydromyrcene, and hexahydromyrcene.

"Hydrogenated ocimene" refers to an ocimene molecule in which at least one carbon-carbon double bond is hydrogenated. Hydrogenated ocimene encompasses ocimene in which one, two, or three double bonds are hydrogenated, and any mixtures thereof. Partially hydrogenated ocimene refers to an ocimene molecule in which only one or two double bonds have been hydrogenated, and also refers to a hydrogenated ocimene sample in which at least about 5% of the carbon-carbon double bonds remain unsaturated. A sample of partially hydrogenated ocimene may comprise dihydroocimene, tetrahydroocimene, hexahydroocimene, or any combination thereof. In some cases, a partially hydrogenated ocimene sample comprises ocimene in addition to one or more of dihydroocimene, tetrahydroocimene, and hexahydroocimene.

"Hydrogenated farnesene" refers to farnesene (e.g. β-farnesene or α-farnesene) wherein at least one carbon-carbon double bond is hydrogenated. Hydrogenated farnesene encompasses β-farnesene or α-farnesene in which one, two, three or four double bonds are hydrogenated, and any mixtures thereof. Hydrogenated farnesene is obtained by complete or partial hydrogenation of farnesene, and encompasses farnesane. Partially hydrogenated farnesene refers to farnesene (e.g. β-farnesene or α-farnesene) in which one, two, or three double bonds are hydrogenated, and any mixture thereof. Partially hydrogenated farnesene refers to a farnesene molecule in which only one, two or three double bonds have been hydrogenated, and also refers to a hydrogenated farnesene sample in which at least about 5% of the carbon-carbon double bonds remain unsaturated. A sample of partially hydrogenated farnesene may include farnesene in addition to one or more of dihydrofarnesene, tetrahydrofarnesene, hexahydrofarnesene, and farnesane.

In the following description, all numbers disclosed herein are approximate values, regardless of whether the word "about" or "approximate" is used in connection therewith. Numbers may vary by 1%, 2%, 5%, or sometime, 10 to 20%. Whenever a numerical range with a lower limit $R^L$ and an upper limit $R^U$ is disclosed, any number falling within the range is specifically disclosed. In particular, the following numbers $R_k$ within the range are specifically disclosed: $R_k = R^L + k*(R^U - R^L)$, wherein k is a variable ranging from 1% to 100% with a 1% increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Further, any numerical range defined by any two numbers $R_k$ as defined above is also specifically disclosed herein.

As used herein and unless otherwise indicated, a reaction that is "substantially complete" means that the reaction contains more than about 80% desired product by percent yield, more than about 90% desired product by percent yield, more than about 95% desired product by percent yield, or more than about 97% desired product by percent yield. As used herein, a reactant that is "substantially consumed" means that more than about 85%, more than about 90%, more than about 95%, more than about 97% of the reactant has been consumed, by weight %, or by mol %.

A composition that consists "predominantly" of a component refers to a composition comprising 60% or more of that component, unless indicated otherwise. A composition that "consists essentially of" a component refers to a composition comprising 80% or more of that component, unless indicated otherwise.

As used herein, % refers to % measured as wt. % or as area % by GC-MS or GC-FID, unless specifically indicated otherwise.

DESCRIPTION

In general, partial hydrogenation of alkenes comprising multiple carbon-carbon double bonds results in a mixture of species, e.g., a mixture comprising a statistically determined distribution of partially hydrogenated and completely hydrogenated species. However, described herein are methods for partial hydrogenation of conjugated alkenes in which the distribution of species in the final partially hydrogenated product is other than expected by statistical considerations. For example, provided herein are partial hydrogenation methods that produce i) essentially tri-olefinic species with limited amounts of alkane and conjugated diene (referred to herein as a tri-olefinic feedstock); ii) a mixture comprising predominantly a mixture of di-olefinic and mono-olefinic species with limited amounts of alkane, and little or no conjugated diene; iii) at least about 50% mono-olefinic species with limited amounts of alkane, limited amounts of di-olefinic species, limited amounts of tri-olefinic species, and little or no conjugated diene (referred to herein as a mono-olefinic feedstock); or iv) at least about 50% mono-olefinic species with limited amounts of di-olefinic species (e.g., unconjugated di-olefinic species) (also referred to herein as a mono-olefinic feedstock). The partially hydrogenated products described herein have utility as olefinic feedstocks, which may be used as substitutes for or as supplements for conventional olefinic feedstocks in any chemical process to make a variety of end products.

In some variations, the olefinic feedstocks are derived from a conjugated alkene. The conjugated alkene can be cyclic or acyclic, linear or branched. The conjugated alkene generally comprises at least a conjugated diene. The conjugated alkene can further comprise one or more additional olefinic bonds. In certain embodiments, the conjugated alkene further comprises one, two, three, four or more than four additional olefinic bonds. In certain embodiments, the conjugated alkene is a $C_{10}$-$C_{30}$ conjugated alkene. In certain embodiments, the conjugated alkene is a terpene. In certain embodiments, the terpene is a $C_{10}$-$C_{30}$ terpene. In certain embodiments, the terpene is selected from the group consisting of a monoterpene, a sesquiterpene, a diterpene, a triterpene and any combination thereof. In some variations, the olefinic feedstocks are derived from myrcene, ocimene, farnesene, springene, geranylfarnesene, isodehydrosqualene, isosqualane precursor I, or isosqualane precursor II.

In some variations, an olefinic feedstock is derived from a single conjugated hydrocarbon terpene, e.g. a $C_{10}$-$C_{30}$ conjugated hydrocarbon terpene such as myrcene, ocimene, farnesene, springene, geranylfarnesene, isodehydrosqualene, isosqualane precursor I, or isosqualane precursor II. In some variations, an olefinic feedstock is derived from two or more conjugated hydrocarbon terpenes (e.g., an olefinic feedstock produced by partial hydrogenation of a mixture of two or more hydrocarbon terpenes, an olefinic feedstock comprising a mixture of two or more partially hydrogenated hydrocarbon terpenes, or an olefinic feedstock comprising two or more co-feeds, where one co-feed comprises a first partially hydrogenated terpene and another co-feed comprises a different partially hydrogenated terpene). In some variations, the olefinic feedstock is derived from farnesene, e.g. β-farnesene and/or α-farnesene. In certain variations, the olefinic feedstock is derived from a mixture of farnesene (e.g., β-farnesene and/or α-farnesene) and myrcene.

The conjugated terpenes disclosed herein may be obtained from any suitable source. In some embodiments, the conjugated terpene is obtained from naturally occurring plants or marine species. For example, farnesene can be obtained or derived from naturally occurring terpenes that can be produced by a variety of plants, such as *Copaifera langsdorfii*, conifers, and spurges; or by insects, such as swallowtail butterflies, leaf beetles, termites, or pine sawflies; and marine organisms, such as algae, sponges, corals, mollusks, and fish. Terpene oils can also be obtained from conifers and spurges. Conifers belong to the plant division Pinophya or Coniferae and are generally cone-bearing seed plants with vascular tissue. Conifers may be trees or shrubs. Non-limiting examples of suitable conifers include cedar, cypress, douglas fir, fir, juniper, kauris, larch, pine, redwood, spruce and yew. Spurges, also known as *Euphorbia*, are a diverse worldwide genus of plants belonging to the spurge family (euphorbiaceae). Farnesene is a sesquiterpene, a member of the terpene family, and can be derived or isolated from terpene oils for use as described herein. In some embodiments, a conjugated terpene is derived from a fossil fuel (petroleum or coal), for example, by fractional distillation of petroleum or coal tar. In some embodiments, a conjugated terpene is made by chemical synthesis. For example, one non-limiting example of suitable chemical synthesis of farnesene includes dehydrating nerolidol with phosphoryl chloride in pyridine as described in the article by Anet E. F. L. J., "Synthesis of (E,Z)-α-, and (Z)-β-farnesene", Aust. J. Chem. 23(10), 2101-2108, which is incorporated herein by reference in its entirety. U.S. Pat. No. 4,546,110, which is incorporated herein by reference in its entirety, describes synthesis of a mixture of (E)-β-farnesene and (Z)-β-farnesene from nerolidol. Farnesol or nerolidol may be converted into α-farnesene or β-farnesene, or a combination thereof by dehydration with a dehydrating agent or an acid catalyst. Any suitable dehydrating agent or acid catalyst that can convert an alcohol into an alkene may be used. Non-limiting examples of suitable dehydrating agents or acid catalysts include phosphoryl chloride, anhydrous zinc chloride, phosphoric acid, and sulfuric acid.

In some embodiments, a conjugated terpene is obtained using genetically modified organisms that are grown using renewable carbon sources (e.g., sugar cane). In certain embodiments, a conjugated terpene is prepared by contacting a cell capable of making a conjugated terpene with a suitable carbon source under conditions suitable for making a conjugated terpene. Non-limiting examples conjugated terpenes obtained using genetically modified organisms are provided in U.S. Pat. No. 7,399,323, U.S. Pat. Publ. Nos. 2008/0274523 and 2009/0137014, and International Patent Publication WO 2007/140339, and International Patent Publication WO 2007/139924, each of which is incorporated herein by reference in its entirety. Any carbon source that can be converted into one or more isoprenoid compounds can be used herein. In some embodiments, the carbon source is a fermentable carbon source (e.g., sugars), a non-fermentable carbon source or a combination thereof. A non-fermentable carbon source is a carbon source that cannot be converted by an organism into ethanol. Non-limiting examples of suitable non-fermentable carbon sources include acetate, glycerol, lactate and ethanol.

The sugar can be any sugar known to one of skill in the art. For example, in some embodiments, the sugar is a monosaccharide, disaccharide, polysaccharide or a combination thereof. In certain embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose, and combinations thereof. In some embodiments, the sugar is sucrose. In certain embodiments, the carbon source is a polysaccharide. Non-limiting examples of suitable polysaccharides include starch, glycogen, cellulose, chitin, and combinations thereof.

The sugar suitable for making a conjugated terpene can be obtained from a variety of crops or sources. Non-limiting examples of suitable crops or sources include sugar cane, bagasse, miscanthus, sugar beet, sorghum, grain sorghum, switchgrass, barley, hemp, kenaf, potato, sweet potato, cassava, sunflower, fruit, molasses, whey, skim milk, corn, stover, grain, wheat, wood, paper, straw, cotton, cellulose waste, and other biomass. In certain embodiments, suitable crops or sources include sugar cane, sugar beet and corn. In some embodiments, the sugar source is cane juice or molasses.

In certain embodiments, a conjugated terpene can be prepared in a facility capable of biological manufacture of isoprenoids. For example, for making a $C_{15}$ isoprenoid, the facility may comprise any structure useful for preparing $C_{15}$ isoprenoids (e.g., α-farnesene, β-farnesene, nerolidol or farnesol) using a microorganism capable of making the $C_{15}$ isoprenoids with a suitable carbon source under conditions suitable for making the $C_{15}$ isoprenoids. In some embodiments, the biological facility comprises a cell culture comprising a desired isoprenoid (e.g., a $C_5$, $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture. In certain embodiments, the biological facility comprises a fermentor comprising one or more cells capable of generating a desired isoprenoid. Any fermentor that can provide for cells or bacteria a stable and optimal environment in which they can grow or reproduce may be used herein. In some embodiments, the fermentor comprises a culture comprising one or more cells capable of generating a desired isoprenoid (e.g., a $C_{10}$, a $C_{15}$, a $C_{20}$, or a $C_{25}$ isoprenoid). In some embodiments, the fermentor comprises a cell culture capable of biologically manufacturing farnesyl pyrophosphate (FPP). In certain embodiments, the fermentor comprises a cell culture capable of biologically manufacturing isopentenyl diphosphate (IPP). In some embodiments, the fermentor comprises a cell culture comprising a desired isoprenoid (e.g., a $C_{10}$, a $C_{15}$, a $C_{20}$, or a $C_{25}$ isoprenoid) in an amount of at least about 1 wt. %, at least about 5 wt. %, at least about 10 wt. %, at least about 20 wt. %, or at least about 30 wt. %, based on the total weight of the cell culture.

The facility may further comprise any structure capable of manufacturing a chemical derivative from the desired isoprenoid (e.g., a $C_5$, $C_{10}$, a $C_{15}$, a $C_{20}$, or a $C_{25}$ isoprenoid). In some embodiments, a facility comprises a reactor for dehydrating nerolidol or farnesol to α-farnesene or β-farnesene or a combination thereof. In certain embodiments, a facility comprises a reactor for dehydrating linalool to myrcene or ocimene or a combination thereof. Any reactor that can be used to convert an alcohol into an alkene under conditions known to skilled artisans may be used. In some embodiments, the reactor comprises a dehydrating catalyst.

Advantageously, in any of the embodiments described herein, the conjugated alkenes may be produced using renewable resources. As used herein, a "renewable carbon" source refers to a carbon source that is made from modern carbon that can be regenerated within several months, years or decades rather than a carbon source derived from fossil fuels (e.g., petroleum) that takes typically a million years or more to regenerate. The terms "renewable carbon" and "biobased carbon" are used interchangeably herein. "Atmospheric carbon" refers to carbon atoms from carbon dioxide molecules that have been free in earth's atmosphere recently, e.g. in the most recent few decades. For example, conjugated hydrocarbon terpenes used in any one of the embodiments described herein can be made from microorganisms, including bioengineered microorganisms, using a renewable carbon source. Myrcene, ocimene, farnesene, isodehydrosqualene, isosqualane precursor I, and isosqualane precursor II can be derived from a renewable carbon source using genetically modified microbial cells as described in U.S. Pat. Nos. 7,659,097, 7,399,323, International Patent Publication WO 2007/139924, International Patent Publication WO 2010/042208, or U.S. Patent Application Publication No. 2011/0287988, each of which is incorporated herein by reference in its entirety as if put forth fully below. In some variations, the olefinic feedstocks (e.g. $C_{10}$-$C_{30}$ olefins) described herein can be used as substitutes for or as supplements to conventional olefinic feedstocks derived from fossil fuels.

Renewable carbon content can be measured using any suitable method. For example, renewable carbon content can be measured according to ASTM D6866-11, "Standard Test Methods for Determining the Biobased Content of Solid, Liquid, and Gaseous Samples Using Radiocarbon Analysis," published by ASTM International, which is incorporated herein by reference in its entirety. Some carbon in atmospheric carbon dioxide is the radioactive $^{14}C$ isotope, having a half-life of about 5730 years. Atmospheric carbon dioxide is utilized by plants to make organic molecules. The atmospheric $^{14}C$ becomes part of biologically produced substances. As the biologically produced organic molecules degrade to produce carbon dioxide into the atmosphere, no net increase of carbon in the atmosphere is produced as a result, which may control or diminish undesired climate effects that may result when molecules produced from fossil fuels degrade to produce carbon dioxide to increase carbon in the atmosphere.

Isotope fractionation occurs during physical processes and chemical reactions, and is accounted for during radiocarbon measurements. Isotope fractionation results in enrichment of one isotope over another isotope. Exemplary processes that can affect isotope fractionation include diffusion (e.g., thermal diffusion), evaporation, and condensation. In some chemical reactions, certain isotopes may exhibit different equilibrium behaviors than others. In some chemical reactions, kinetic effects may affect isotope ratios. In the carbon cycle of plants, isotope fractionation occurs. During photosynthesis, the relative amounts of different carbon isotopes that are consumed are $^{12}C > ^{13}C > ^{14}C$, due to slower processing of heavier isotopes. Plants species exhibit different isotope fractionation due to isotopic discrimination of photosynthetic enzymes and diffusion effects of their stomata. For example $C_3$ plants exhibit different isotope fractionation than $C_4$ plants. The international reference standard for isotope fractionation between $^{13}C$ and $^{12}C$ is PDB (Pee Dee Belemnite standard) or VPDB (Vienna Pee Dee Belemnite standard, replacement for depleted PDB standard). For a given sample, isotope fractionation can be expressed as $\delta\ ^{13}C$ (per mil)={[R(sample)/R(VPDB standard)]−1}×1000‰, where R(sample)=$^{13}C/^{12}C$ and R(VPDB standard)=$^{13}C/^{12}C$ for the VPDB standard. Instead of a $^{13}C/^{12}C$ ratio, $\delta^{13}C$ is the relative change of the $^{13}C/^{12}C$ ratio for a given sample from that of the VPDB standard. Carbon isotopic ratios are reported on a scale defined by adopting a $\delta^{13}C$ value of +0.00195 for NBS-19 limestone (RM 8544) relative to VPDB. "New IUPAC guidelines for the reporting of stable hydrogen, carbon, and oxygen isotope-ratio data," Letter to the Editor, J. Res. Natl. Stand. Technol. 100, 285 (1995). Most naturally occurring materials exhibit negative $\delta^{13}$ values. In general, for atmospheric $CO_2$ $\delta^{13}$ ranges between −11 to −6‰, for $C_3$ plants, $\delta^{13}C$ varies between −22 and −32‰, and for $C_4$ plants $\delta^{13}C$ varies between −8 to −18√. The $^{14}C$ fractionation factor can be approximated as the square of the $^{13}C$ fractionation factor. See, e.g., M. Stuiver and S. W. Robinson, Earth and Planetary Science Letters, vol. 23, 87-90.

$^{14}C$ content of a sample can be measured using any suitable method. For example, $^{14}C$ content can be measured using Accelerator Mass Spectrometry (AMS), Isotope Ratio Mass Spectrometry (IRMS), Liquid Scintillation Counting (LSC), or a combination of two or more of the foregoing, using known instruments. Activity refers to the number of decays measured per unit time and per unit mass units. To compare activity of a sample with that of a known reference material, isotope fractionation effects can be normalized. If an activity of a sample is measured to be $A_S$, the sample activity normalized to the reference is $A_{SN}$ and can be expressed as: $A_{SN}=A_S\{[(^{13}/^{12}C)\text{reference}]/[(^{13}C/^{12}C)\text{sample}]\}^2$.

Radiocarbon measurements are performed relative to a standard having known radioactivity. SRM 4990B is an oxalic acid dehydrate Standard Reference Material provided by the U.S. National Bureau of Standards (now National Institute of Standards and Technology, NIST) in the late 1950s having $\delta^{13}C$=−19‰ (PDB). SRM 4990B has been depleted so another standard is used, such as SRM 4990C, a second oxalic acid standard from NIST having $\delta^{13}C$=−17.8‰ (VPDB). Modern carbon, referenced to AD 1950, is 0.95 times $^{14}C$ concentration of SRM 4990B, normalized to $\delta^{13}C$=−19√ (PDB). The factor 0.95 is used to correct the value to 1950 because by the late 1950s, $^{14}C$ in the atmosphere had artificially risen about 5% above natural values due to testing of thermonuclear weapons. Fraction of modern ($f_M$) refers to a radiocarbon measured compared to modern carbon, referenced to AD1950. Modern carbon as defined above has $f_M$=1. For current living plant material not more than a few years old (such as corn), $f_M$ is approximately 1.1. Percent modern carbon (pMC) is $f_M$×100%. The AD 1950 standard had 100 pMC. Fresh plant material may exhibit a pMC value of about 107.5. Biobased carbon content is determined by setting 100% biobased carbon equal to the pMC value of freshly grown plant material (such as corn), and pMC value of zero corresponds to a sample in which all of the carbon is derived from fossil fuel (e.g., petroleum). A sample containing both modern carbon and carbon from fossil fuels will exhibit a biobased carbon content between 0 and 100%. In some cases, a sample that is more than several years old but containing all biobased carbon (such as wood from a mature tree trunk) will exhibit a pMC value to yield a biobased carbon content >100%.

Renewable carbon content or biobased carbon content as used herein refers to fraction or percent modern carbon determined by measuring $^{14}C$ content, e.g., by any of Method A, Method B, or Method C as described in ASTM D6866-11 "Standard Test Methods for Determining the Biobased Content of Solid, Liquid, and Gaseous Samples Using Radiocarbon Analysis." Counts from $^{14}C$ in a sample can be compared directly or through secondary standards to SRM 4990C. A measurement of 0% $^{14}C$ relative to the appropriate standard indicates carbon originating entirely from fossils (e.g., petroleum based). A measurement of 100% $^{14}C$ indicates carbon originating entirely from modern sources. A measurement of >100% $^{14}C$ indicates the source of carbon has an age of more than several years.

In some variations, about 100% of the carbon atoms in the olefinic feedstocks described herein originate from renewable carbon sources. In some variations, the olefinic feedstocks have a $\delta^{13}C$ of from about −11 to about −6‰, from about −15 to about −10‰, from about −22 to about −15‰, from about −22 to about −32‰, from −8 to about −18‰, from about −14 to about −12‰, or from about −13 to about −11‰. In some variations, the olefinic feedstocks have a $f_M$ greater than about 0.3, greater than about 0.4, greater than about 0.5, greater than about 0.6, greater than 0.7, greater than about 0.8, greater than about 0.9, or greater than about 1.0. In some variations, the olefinic feedstocks have a $f_M$ of about 1.0 to about 1.05, about 1.0 to about 1.1, or about 1.1 to about 1.2. In some variations, the olefinic feedstocks have a $\delta^{13}C$ from about −15 to about −10‰ and a $f_M$ greater than about 0.5, greater than about 0.7, or greater than about 1.0. In some variations, the olefinic feedstocks have a $\delta^{13}C$ from about −8 to about −18‰ and a $f_M$ greater than about 0.5, greater than about 0.7, or greater than about 1.0. In some variations, the conjugated hydrocarbon terpene (e.g., myrcene, β-farnesene, or α-farnesene) is made by genetically modified microorganisms using renewable carbon sources such as a sugar (e.g., sugar cane). The renewable carbon content of the olefinic feedstocks may be measured using any suitable method, e.g., using radiocarbon analysis as described herein.

The olefinic feedstocks described herein comprise virtually no sulfur and no aromatic compounds, making them environmentally preferable over conventional olefins derived from fossil fuels, which in many cases contain sulfur and aromatics, such as naphthalenes. In certain embodiments, the olefinic feedstocks comprise less than about 10 ppm sulfur, less than about 1 ppm sulfur, less than about 100 ppb sulfur, less than about 10 ppb sulfur or less than about 1 ppb sulfur. In certain embodiments, the olefinic feedstocks comprise less than about 10 ppm aromatics, less than about 1 ppm aromatics, less than about 100 ppb aromatics, less than about 10 ppb aromatics or less than about 1 ppb aromatics. In certain embodiments, the olefinic feedstocks comprise less than about 10 ppm sulfur and less than about 10 ppm aromatics, less than about 1 ppm sulfur and less than about 1 ppm aromatics, less than about 100 ppb sulfur and less than about 100 ppb aromatics, less than about 10 ppb sulfur and less than about 10 ppb aromatics, or less than about 1 ppb sulfur and less than about 1 ppb aromatics.

In those variations in which the olefinic feedstocks are derived from an acyclic conjugated hydrocarbon alkene, the olefinic feedstocks described herein may comprise less than about 5%, less than about 2%, less than about 1%, less than about 0.1%, or less than about 0.01% cyclic compounds.

In certain embodiments, the olefinic feedstocks described herein comprise one or more methylated alkenes, e.g., one or more methylated mono-alkenes, methylated di-alkenes, methylated tri-alkenes, or methylated tetra-alkenes, where the number of carbon atoms in the base alkene for any of the above corresponds to the number of carbon atoms in the main chain of a conjugated alkene (which may be a hydrocarbon terpene in some variations) used to make the feedstock, and the number of methyl substituents corresponds to the number of methyl substituents (or in some cases, methyl and methylene substituents) on the conjugated alkene (which may be a hydrocarbon terpene in some variations) used to make the feedstock. In some variations, the olefinic feedstocks are derived from a $C_{10}$-$C_{30}$ conjugated alkene comprising 1-10 methyl or methylene substituents, e.g., 1, 2, 3, 4, 5, 6, 7, 8, 9, or 10 methyl or methylene substituents. In some variations, the olefinic feedstocks are derived from a $C_{10}$-$C_{30}$ conjugated alkene comprising at least one ethyl or vinyl substituent. In some variations, the olefinic feedstocks are derived from a $C_{10}$-$C_{30}$ conjugated alkene comprising 1-10 methyl or methylene substituents and at least one ethyl or vinyl substituent.

The olefinic feedstocks described herein can comprise a well-defined distribution of methylated alkenes and (in some cases methylated alkanes) within a very narrow molecular weight range (e.g. a distribution spanning a range from about 2-10 amu, or from about 2-20 amu) as molecules within the distribution have the same number of carbon atoms. Thus, a feedstock comprising a very narrow molecular weight range can be produced directly, without the need for cracking or a separation process such as distilling from a crude mixture, as is commonly employed in the production of $C_{10}$-$C_{30}$ olefinic feedstocks from petroleum products. An olefinic feedstock described herein that is derived from more than one partially hydrocarbon terpene species can exhibit a broader but predictable molecular weight distribution as produced, again without the need for a separation process.

The feedstocks described herein can provide unique methylated olefinic feedstocks that do not require an extra alkylation step to incorporate short chain branching, or any separation step to isolate. Furthermore, the degree of branching, the type of branching, and the branching position in the olefins in feedstocks described herein are predetermined by the source hydrocarbon terpene or terpenes, unlike other feedstocks comprising branched olefins, wherein the branched olefins comprise a complex mixture of isomers wherein the degree of branching, the type of branching and the branching position are all varied.

Provided herein are methods for making olefinic feedstocks from a conjugated alkene (e.g., a $C_{10}$-$C_{30}$ conjugated hydrocarbon terpene) comprising at least one conjugated diene and at least one additional carbon-carbon double bond by controlled partial hydrogenation. In certain variations, an olefinic feedstock is made by controlled partial hydrogenation of myrcene, ocimene, farnesene, springene, geranylfarnesene, isodehydrosqualene, isosqualane precursor I, or isosqualane precursor II.

The controlled partial hydrogenation process may in some variations be staged, so as to comprise two or more stages, with each stage designed to tune the resulting olefin composition of the olefinic feedstock. For example, a multi-stage hydrogenation process may be used to produce an olefinic feedstock that is rich in mono-olefinic species (e.g., comprises at least about 60% mono-olefins). In one variation of a staged hydrogenation process, a first hydrogenation stage may comprise selectively hydrogenating at least one olefinic bond in the conjugated diene to produce an intermediate partially hydrogenated product, and a second hydrogenation stage may comprise selectively hydrogenating the intermediate product in a second hydrogenation stage to produce a desired olefinic composition, e.g., an olefinic composition rich in mono-olefins, and/or an olefinic composition in which alkane formation has been minimized.

Also provided herein are examples of specific compositions for olefinic feedstocks derived by partial hydrogenation of conjugated hydrocarbon terpenes. For example, the following classes of olefinic feedstock compositions are disclosed herein: i) olefinic feedstocks compositions that have very low amounts of conjugated dienes (e.g., less than about 10% conjugated diene, less than about 5% conjugated diene, or less than about 1% conjugated diene); ii) olefinic feedstocks comprised predominantly of mono-olefins and di-olefins (e.g., at least about 80%, or at least about 90%, or at least about 95% mono-olefins and di-olefins); iii) olefinic feedstock compositions comprised predominantly of mono-olefinic species (e.g., at least about 60%, at least about 65%, at least about 70%, at least about 75%, or at least about 80% mono-olefins); v) olefinic feedstock compositions that have limited amounts of alkanes (e.g., less than about 25%, less than about 20%, less than about 15%, less than about 10%, or less than about 5%); vi) olefinic feedstock compositions that have limited amounts of conjugated dienes and limited amounts of alkanes; vii) olefinic feedstock compositions consisting essentially of tri-olefins and having limited amounts of conjugated dienes and alkanes; viii) olefinic feedstock compositions comprised predominantly of mono-olefins and having limited amounts of dienes (both unconjugated and conjugated) and alkanes; and ix) olefinic feedstock compositions comprising substantial amounts of mono-olefins (e.g., at least about 50%, at least about 55%, at least about 60%, at least 65%, at least about 70%, at least about 75%, or at least about 80% mono-olefin) and limited amounts of di-olefins (e.g., at most about 10%, at most about 8%, at most about 5%, at most about 3%, at most about 2%, at most about 1% di-olefin, or at most about 0.5% di-olefin). In some variations, di-olefins that are present may be substantially unconjugated, e.g., so that a composition comprises at most about 2%, at most about 1%, at most about 0.5%, at most about 0.1%, or no detectable conjugated species.

Provided herein are specific species of partially hydrogenated hydrocarbon terpenes. For example, provided herein are alpha-olefins derived from a 1,3-diene conjugated hydrocarbon terpene (e.g., a $C_{10}$-$C_{30}$ conjugated hydrocarbon terpene such as farnesene, myrcene, ocimene, springene, or geranylfarnesene).

Methods

Provided herein are methods for making olefinic feedstocks from a conjugated alkene (e.g., a conjugated hydrocarbon terpene, which may be an acyclic or cyclic $C_{10}$-$C_{30}$ conjugated hydrocarbon terpene) comprising at least one conjugated diene and at least one additional carbon-carbon double bond by controlled (e.g., staged) partial hydrogenation.

A conjugated alkene comprising at least one conjugated diene and at least one additional C—C double bond is represented by structure A1 (or a stereoisomer thereof, including (E,E), (E,Z), (Z,E), and (Z,Z) stereoisomers and rotational isomers):

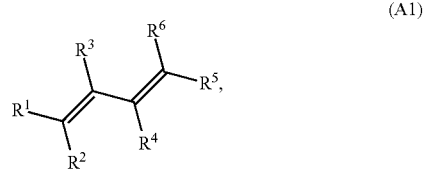

(A1)

where $R^1$, $R^2$, $R^3$, $R^4$, $R^5$, and $R^6$ are each independently H, or a $C_1$-$C_{25}$ linear or branched, cyclic or acrylic, saturated or unsaturated hydrocarbon group, and at least one of the group consisting of $R^1$, $R^2$, $R^3$, $R^4$, $R^5$, and $R^6$ contains at least one carbon carbon double bond. In some variations at least one of $R^1$, $R^2$, $R^3$, $R^4$, $R^5$, and $R^6$ may contain two, three, four, five, or six or more carbon carbon double bonds. In some variations, at least one of $R^1$, $R^2$, $R^3$, $R^4$, $R^5$, and $R^6$ is a monoene substituted with one or more methyl groups or a polyene substituted with one or more methyl groups

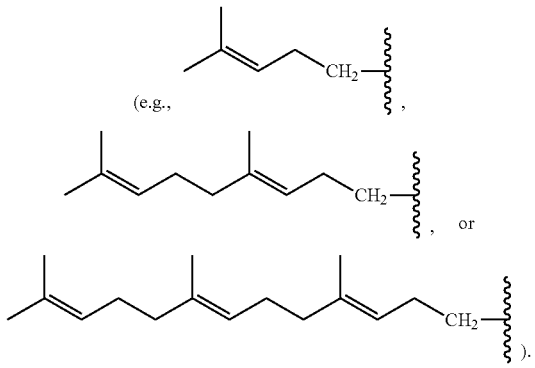

(e.g., ... , or ... ).

In some embodiments, the conjugated alkene comprises a terminal carbon-carbon double bond as part of the conjugated diene and at least one additional carbon-carbon double bond, and has structure A3 (or a stereoisomer thereof including (E,E), (E,Z), (Z,E), and (Z,Z) stereoisomers and rotational isomers):

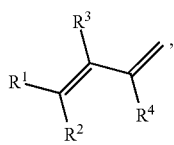

(A3)

where $R^1$, $R^2$, $R^3$, and $R^4$ are each independently H, or a $C_1$-$C_{25}$ linear or branched, cyclic or acyclic, saturated or unsaturated hydrocarbon group, and at least one of the group consisting of $R^1$, $R^2$, $R^3$, and $R^4$ contains at least one carbon carbon double bond. In some variations, at least one of $R^1$, $R^2$, $R^3$, and $R^4$ may contain two, three, four, five, or six or more carbon carbon double bonds. In some variations, at least one of $R^1$, $R^2$, $R^3$, and $R^4$ is a monoene substituted with one or more methyl groups or a polyene substituted with one or more methyl groups

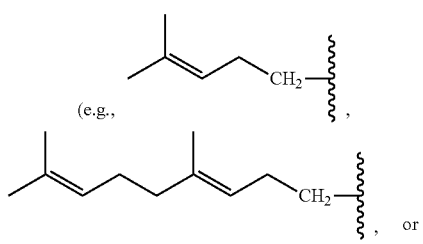

(e.g., ... , or

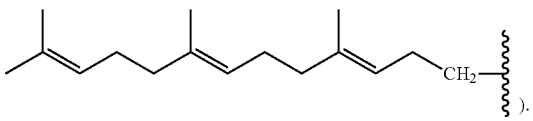

).

In some embodiments, the conjugated alkene has structure A5 (or a stereoisomer thereof):

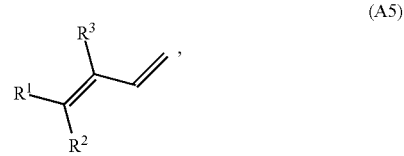

(A5)

where $R^1$, $R^2$ and $R^3$ are each independently H or a $C_1$-$C_{25}$ linear or branched, cyclic or acyclic, saturated or unsaturated hydrocarbon group, and at least one of the group consisting of $R^1$, $R^2$ and $R^3$ contains at least one carbon carbon double bond. In some variations, at least one of $R^1$, $R^2$ and $R^3$ may contain two, three, four, five, or six or more carbon carbon double bonds. In some variations, at least one of $R^1$, $R^2$ and $R^3$ is a monoene substituted with one or more methyl groups or a polyene substituted with one or more methyl groups

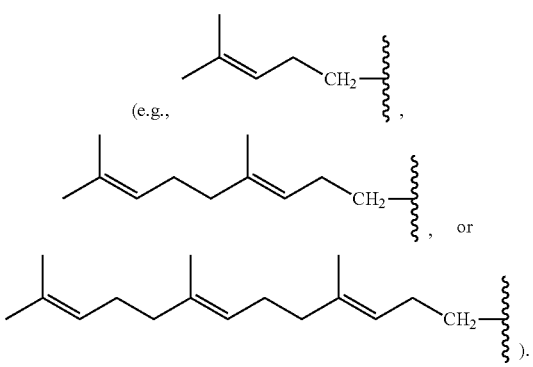

(e.g., ... , ... , or ... ).

In some embodiments, the conjugated alkene has structure A7 (or a stereoisomer thereof including (E,E), (E,Z), (Z,E), and (Z,Z) stereoisomers and rotational isomers):

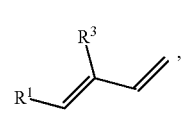

(A7)

where $R^1$ and $R^3$ are each independently H or a $C_1$-$C_{25}$ linear or branched, cyclic or acyclic, saturated or unsaturated hydrocarbon group, and at least one of the group consisting of $R^1$ and $R^3$ contains at least one carbon carbon double bond. In some variations, at least one of $R^1$ and $R^3$ may contain two, three, four, five, or six or more C—C double bonds. In some variations, at least one of $R^1$ and $R^3$ is a monoene substituted with one or more methyl groups, or a polyene substituted with one or methyl groups (e.g., 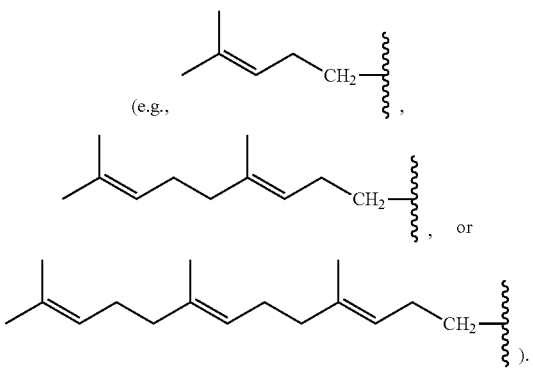).

In some embodiments, the conjugated alkene has structure A9 (or a stereoisomer thereof including (E,E), (E,Z), (Z,E), and (Z,Z) stereoisomers and rotational isomers):

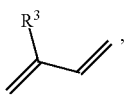 (A9)

where $R^3$ is a $C_5$-$C_{25}$ linear or branched, cyclic or acyclic unsaturated hydrocarbon group containing at least one carbon carbon double bond, or in some variations two, three, four, five, or six or more carbon carbon double bonds. In some variations, at $R^3$ is a monoene substituted with one or more methyl groups or a polyene substituted with one or more methyl groups, (e.g., 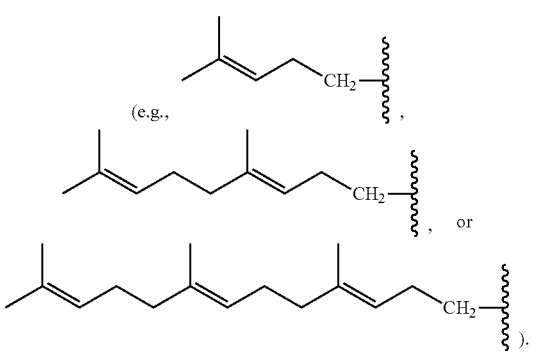).

As stated above, in some variations, a conjugated alkene comprising at least one additional carbon-carbon double bond from which the olefinic feedstock is derived is a conjugated hydrocarbon terpene comprising at least one additional carbon-carbon double bond. Thus a conjugated hydrocarbon terpene having any of the above-listed structures A1-A9 (or stereoisomers thereof) may be used to make the olefinic feedstocks described herein. In some variations, a conjugated hydrocarbon terpene having structure A9 with $R^3$ being a $C_5$-$C_{25}$ monoene or polyene may be used to make the olefinic feedstocks described herein.

Nonlimiting examples of conjugated hydrocarbons comprising at least one additional carbon-carbon double bonds include: myrcene has structure A9 with

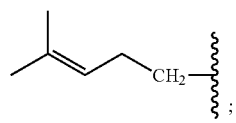

α-ocimene has structure A7 with $R^1$=$CH_3$ and

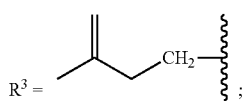

β-ocimene has structure A7 with $R^1$=$CH_3$ and

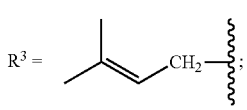

α-farnesene has structure A7 with

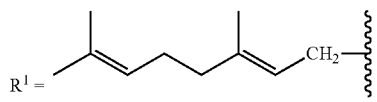 [SMILES: *C/C=C(\C)CCC=C(C)C]

and $R^3$=$CH_3$; β-farnesene has structure A9 with

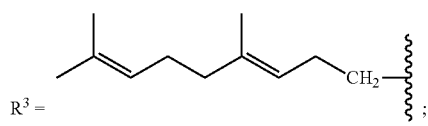 [SMILES: *CC/C=C(\C)CCC=C(C)C]

β-springene has structure A9 with

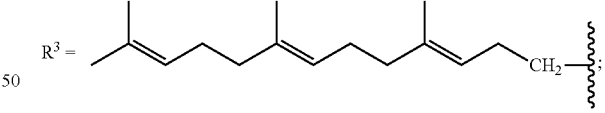

isodehydrosqualene has structure A1 with

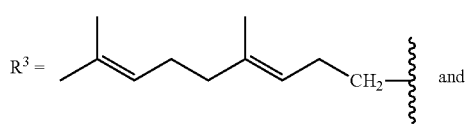 and

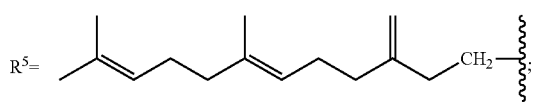

isosqualane precursor I has structure A1 with

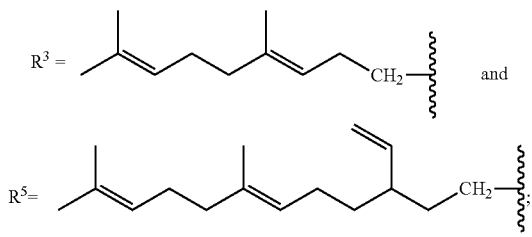

and isosqualane precursor II has structure A1 with $R^1$=H, $R^2$=H, $R^4$=H, $R^6$=H,

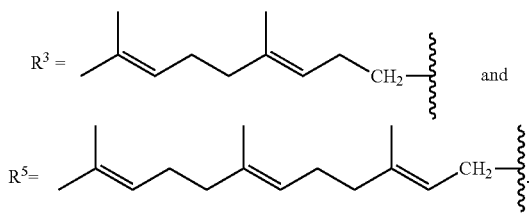

In certain embodiments, methods for making olefinic feedstocks from a conjugated alkene (e.g., a conjugated hydrocarbon terpene) comprising at least one conjugated diene and at least one additional carbon carbon double bond by controlled hydrogenation comprise selectively hydrogenating at least one olefinic bond in the conjugated diene in a first stage to produce a partially hydrogenated olefinic intermediate, and selectively hydrogenating the partially hydrogenated olefinic intermediate in one or more subsequent stages (e.g. a second stage for a two stage process) to produce the olefinic feedstock having a desired composition. Such staged partial hydrogenation methods may be applied to any of the aforementioned conjugated alkenes having structures A1-A9 to produce an olefinic feedstock, including but not limited to $C_{10}$-$C_{30}$ conjugated hydrocarbon terpenes such as myrcene, ocimene, farnesene, springene, geranylfarnesene, isodehydrosqualene, isosqualane precursor I, and isosqualane precursor II. In certain embodiments, an olefinic feedstock is produced by staged partial hydrogenation from a conjugated hydrocarbon terpene produced by a bioengineered microorganism using a renewable carbon source. In some variations, the staged partial hydrogenation is conducted in two stages. In some variations, the staged partial hydrogenation is conducted in three or more stages.

In certain embodiments, methods comprising selectively hydrogenating a conjugated terpene comprising at least three olefinic bonds wherein two of the at least three olefinic bonds form a conjugated diene to make a composition rich in mono-olefins and comprising a limited amount of di-olefins. In some variations, no substantial quantities of conjugated di-olefins are present. Such methods may be utilized when a mono-olefinic feedstock is desired, and the presence of di-olefins causes undesired side reactions, cross-products and the like. For example, the methods may be capable of making a composition comprising at least about 50% mono-olefinic species and at most about 10% di-olefinic species, comprising at least about 50% mono-olefinic species and at most about 10% di-olefinic species, at least about 50% mono-olefinic species and at most about 10% di-olefinic species, at least about 50% mono-olefinic species and at most about 5% di-olefinic species, at least about 50% mono-olefinic species and at most about 3% di-olefinic species, at least about 50% mono-olefinic species and at most about 1% di-olefinic species, at least about 50% mono-olefinic species and at most about 0.5% di-olefinic species, at least about 55% mono-olefinic species and at most about 10% di-olefinic species, at least about 55% mono-olefinic species and at most about 5% di-olefinic species, at least about 55% mono-olefinic species and at most about 3% di-olefinic species, at least about 55% mono-olefinic species and at most about 1% di-olefinic species, at least about 55% mono-olefinic species and at most about 0.5% di-olefinic species, at least about 60% mono-olefinic species and at most about 10% di-olefinic species, at least about 60% mono-olefinic species and at most about 5% di-olefinic species, at least about 60% mono-olefinic species and at most about 3% di-olefinic species, at least about 60% mono-olefinic species and at most about 1% di-olefinic species, at least about 60% mono-olefinic species and at most about 0.5% di-olefinic species, at least about 65% mono-olefinic species and at most about 10% di-olefinic species, at least about 65% mono-olefinic species and at most about 5% di-olefinic species, at least about 65% mono-olefinic species and at most about 1% di-olefinic species, at least about 65% mono-olefinic species and at most about 0.5% di-olefinic species, at least about 70% mono-olefinic species and at most about 10% di-olefinic species, at least about 70% mono-olefinic species and at most about 5% di-olefinic species, at least about 70% mono-olefinic species and at most about 1% di-olefinic species, at least about 70% mono-olefinic species and at most about 0.5% di-olefinic species, at least about 75% mono-olefinic species and at most about 10% di-olefinic species, at least about 75% mono-olefinic species and at most about 5% di-olefinic species, at least about 75% mono-olefinic species and at most about 1% di-olefinic species, at least about 75% mono-olefinic species and at most about 0.5% di-olefinic species, at least about 80% mono-olefinic species and at most about 10% di-olefinic species, at least about 80% mono-olefinic species and at most about 5% di-olefinic species, at least about 80% mono-olefinic species and at most about 1% di-olefinic species, at least about 80% mono-olefinic species and at most about 0.5% di-olefinic species, at least about 85% mono-olefinic species and at most about 10% di-olefinic species, at least about 85% mono-olefinic species and at most about 5% di-olefinic species, at least about 85% mono-olefinic species and at most about 1% di-olefinic species, at least about 85% mono-olefinic species and at most about 0.5% di-olefinic species, at least about 90% mono-olefinic species and at most about 10% di-olefinic species, at least about 90% mono-olefinic species and at most about 5% di-olefinic species, at least about 90% mono-olefinic species and at most about 1% di-olefinic species, at least about 90% mono-olefinic species and at most about 0.5% di-olefinic species. For any of the compositions, the amount of sulfur may be less than about 1 ppm. For any of the compositions, the amount of aromatic compounds may be less than about 1 ppm. For any of the compositions, the amount of sulfur and the amount of aromatic compounds may each be less than 1 ppm. For any of the compositions, the terpene is microbially derived from renewable carbon sources, and has a renewable carbon content of about 100%.

A model stepwise or staged hydrogenation process can be described as follows using farnesene as a model compound. The tetraene is reduced to a triene in a first hydrogenation stage having a first rate constant k[1]; the triene is reduced to a diene in a second hydrogenation stage having a second rate constant k[2]; the diene is reduced to a monoene in a third hydrogenation stage having a third rate constant k[3]; and the monoene is reduced to an alkane in a fourth hydrogenation stage having a fourth rate constant k[4]. The stepwise hydrogenation process can be described as follows:

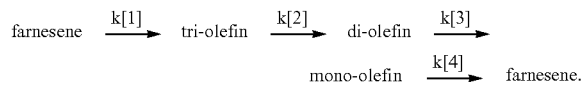

In an uncontrolled partial hydrogenation process, some or all of the four steps may happen nearly coincidentally or in a purely statistical manner so that no or insufficient selectivity as to degree of hydrogenation results. In devising a staged hydrogenation process to produce an olefinic feedstock it is desired to capitalize on the different reactivity of the conjugated diene moiety so as to essentially eliminate the conjugated diene functionality by reducing at least one of the olefinic bonds in the conjugated diene without producing alkane in a first stage so that k[1]>>k[2], followed by selective hydrogenation of one or more of the remaining olefinic bonds while minimizing formation of the alkane in a subsequent stage, e.g., by significantly increasing k[3] and/or reducing k[4] (increasing the ratio k[3]/k[4]). In some variations, it may be desired to produce an olefinic feedstock that comprises predominantly mono-olefinic species, so that a staged hydrogenation process can be devised in which k[3]>>k[4], i.e., so that the di-olefinic species is preferentially hydrogenated over the mono-olefinic species. For example, k[3] may be at least about two times, at least about three times, at least about five times, or at least about ten times k[4]. In some variations, k[1]:k[2] may be at least about 10:1, e.g., about 10:1, 20:1, 30:1, 40:1, 50:1, 60:1, 70:1, 80:1, 90:1, 100:1, 200:1, or even higher. In some variations, k[2] may be similar to k[3], e.g., a ratio k[2]:k[3] may be about 1:1, 2:1, or 1:2. In some variations, a ratio k[1]:k[4] may be at least about 20:1, e.g., about 20:1, 30:1, 40:1, 50:1, 60:1, 70:1, 80:1, 90:1, 100:1, 200:1, or even higher. In some variations, k[1]:k[2]:k[3]:k[4] may be about 80:10:5:1. In some variations, k[1]:k[2]:k[3]:k[4] may about 80:10:5:0.5 or 80:10:5:0.25. In some variations, reaction conditions may be selected such that the ratio k[3]:k[4] results a final olefinic feedstock in which the mono-olefinic content is at least about 60%, at least about 65%, at least about 70%, at least about 75%, or at least about 80%, the di-olefinic content is about 12% or less, about 10% or less, about 8% or less, about 5% or less, or less than 5%, and the alkane content is about 25% or less, about 20% or less, about 18% or less, about 15% or less, about 10% or less, or about 8% or less. The ratio k[3]:k[4] can be tuned using staged hydrogenation processes described herein to tune relative populations of mono-olefinic, di-olefinic, and alkane in an olefinic feedstock. In some variations, it may be desired to have as high a concentration of mono-olefin as possible while achieving as low a concentration of di-olefinic species as possible, as the di-olefinic species may cause side reactions, formation of undesired cross-products, and the like. In some variations, it may be desired to have as high a concentration of mono-olefin as possible while achieving as low a concentration of alkane as possible. Formation of the alkane may cause undesired yield loss. In some variations, it may be desired to have as high a concentration of mono-olefin as possible while achieving as low a concentration of di-olefin as possible. The presence of di-olefins may cause undesired side reactions, cross products, and the like.

As shown in the Examples, the conjugated diene is selectively hydrogenated in the first stage. After selectively reducing the concentration of conjugated diene (e.g., forming tri-olefin in the case of farnesene) in the first stage, hydrogenation in a subsequent stage or stages is controlled to form unconjugated polyenes (e.g., di-olefins) and to selectively favor hydrogenation of the unconjugated polyene (e.g., di-olefins) over hydrogenation of mono-olefin. In the case of farnesene, after the introduction of more than one equivalent of hydrogen in a subsequent stage, the di-olefin population increases, reaches a peak after about two equivalents of hydrogen have been added, and then monotonically decreases. The concentration of mono-olefin monotonically increases as until about three equivalents of hydrogen have been added, and subsequently begins to decrease as more saturated hydrocarbon is formed. As described herein, the degree of hydrogenation can be carefully controlled to achieve a composition in which mono-olefin content is maximized while di-olefin is minimized, to achieve a composition in which mono-olefin content is maximized while alkane is minimized, or to achieve a composition in which mono-olefin content is maximized by di-olefin and alkane are minimized.

In staged partial hydrogenation, the catalysis conditions are changed following a first hydrogenation stage. The catalysis conditions include amount of hydrogen, catalyst, catalyst loading, temperature, hydrogen pressure, and reaction time, and any one of or any combination of each of these variables may be independently varied between the first and subsequent (e.g. second) hydrogenation stages. In certain variations, catalysis conditions of a final (e.g., second stage in a two stage process) stage are selected to favor hydrogenation of polyene species present in an intermediate product over hydrogenation of mono-olefinic species in the intermediate product, thereby limiting the quantity of alkane produced in the final olefinic feedstock and reducing concentration of polyene species. The presence of polyene species in a mono-olefinic feedstock may lead to undesired side reactions and cross-products in some reactions.

In some variations, the amount of hydrogen delivered, the catalyst, catalyst loading, and reaction conditions (reaction temperature, hydrogen pressure and time) in a first stage are selected so that less than about 10%, less than about 5%, less than about 3%, less than about 1%, less than about 0.3% (or even fewer) of the molecules in the intermediate product have a conjugated diene moeity after the first hydrogenation stage.

In some variations, the catalyst type (and associated catalysis conditions) for the first stage are selected to be those that are known in the art to be selective for hydrogenating conjugated diene moieties and are active at temperatures below which thermal dimerization, cyclization, isomerization, or other competing or degradation process of the conjugated alkene occurs. For example, a catalyst system that is active at a temperature in a range from about 20° C. to about 110° C. may be used to catalyze hydrogenation of β-farnesene for a first stage to reduce probability that such a competing process occurs. In some variations, Lindlar's catalyst, palladium catalysts (e.g., palladium catalysts prepared via reduction by organoaluminum compounds of Pd(II) complexes (e.g., PdCl$_2$) with nitrogen-containing ligands; ruthenium compounds, rhodium compounds, chromium compounds, iridium compounds; and cobalt compounds (e.g., as described in U.S. Pat. No. 4,590,319, which is incorporated by reference herein in its entirety), may be selected as a catalyst for a first stage in which the conjugated diene is selectively reduced. Non-limiting examples of regioselective hydrogenation catalysts for 1,3-dienes are provided in Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem., 1990, 55 (6), pp. 1854-1856; in V. M. Frolov et al., "Highly active supported palladium catalysts for selective hydrogenation of conjugated dienes into olefins," Reaction Kinetics and Catalysis Letters, 1984, Volume 25, Numbers 3-4, pp. 319-322; in Tungler, A., Hegedüs, L., Fodor, K., Farkas, G., Fürcht, Á. and Karancsi, Z. P. (2003) "Reduction of Dienes and Polyenes," in *The Chemistry of Dienes and Polyenes, Volume* 2 (ed. Z. Rappoport), John Wiley & Sons, Ltd, Chichester, UK. doi: 10.1002/0470857226.ch12; and in Tungler, A., Hegedüs, L., Fodor, K., Farkas, G., Fürcht, Á. and Karancsi, Z. P., "Reduction of Dienes and Polyenes" in *Patai's Chemistry of Functional Groups* (John Wiley and Sons, Ltd, published online Dec. 15, 2009, DOI: 10.1002/9780470682531.pat0233), each of which is incorporated herein by reference in its entirety.

In some variations, a metal catalyst such as palladium, platinum, nickel, copper, copper-chromium, rhodium, ruthenium or molybdenum on various supports may be used in the first and/or second stage. Nonlimiting examples of palladium-containing catalysts that can be used in the first and/or second hydrogenation stage are Pd/C, Pd/Al$_2$O$_3$, Pd/titanium silicate, Pd/SiO$_2$, Pd on titania, Pd on zirconia, and Pd on alumina-silica). In some variations, catalysis conditions may be selected to be relatively mild in the first stage, e.g., lower activity catalyst, lower catalyst loading, and/or lower temperature (e.g., temperature of 110° C. or lower, or 100° C. or lower) to allow selective hydrogenation of at least one olefinic bond in the conjugated diene over other olefinic bonds that are present, without undesired levels of thermal dimerization, isomerization, or oligomerization. In some variations, a catalyst used in the first and/or subsequent stage is activated before use. For example, some copper-containing catalysts (e.g., Cu/SiO$_2$ or a Cu—Cr catalyst) is activated before use (e.g., at 150-180° C.). In some variations, catalysts that require activation at high temperatures are used in second or subsequent stages of hydrogenation to avoid exposure of the conjugated terpene to temperatures which may cause dimerization and the like. In some variations, more active catalysis conditions are selected for the second or subsequent stages.

In some variations, about 1-1.5 equivalents of hydrogen are consumed during the first hydrogenation stage in which at least one olefinic bond of the conjugated diene is selectively reduced. In some variations, about 1 equivalent of hydrogen is consumed in the first hydrogenation stage. In some variations, about 1.5 equivalents of hydrogen are consumed in the first hydrogenation stage. Thus, if the olefinic intermediate product produced after the first stage contains limited amounts of conjugated diene (e.g., less than about 10%) and limited amounts of alkane (e.g., less than about 1%), the intermediate product consists essentially of unconjugated polyenes in which the number of olefinic bonds is one less than in the starting conjugated alkene. Examples 8 and 9 herein provide non-limiting examples of a first stage of partial hydrogenation of β-farnesene in which one molar equivalent of hydrogen was consumed and the resulting olefinic mixture consists essentially of tri-olefinic species. Examples 16-32 herein provide non-limiting examples of a hydrogenation process in which about 1-1.5 equivalents of hydrogen are consumed in a first hydrogenation stage.

In some variations, about 2-2.5 molar equivalents of hydrogen are consumed during the first hydrogenation stage in which the conjugated diene is selectively reduced. In some variations, about 2 equivalents of hydrogen are consumed in the first hydrogenation stage. In some variations, about 2.5 equivalents of hydrogen are consumed in the first hydrogenation stage. Thus, if the intermediate product produced after the first stage contains limited amounts of conjugated diene (e.g., less than about 10%) and limited amounts of alkane (e.g., less than about 2%), the intermediate product consists essentially of a mixture of monoenes and unconjugated polyenes. Certain Examples herein provide non-limiting examples of partial hydrogenation of β-farnesene in which about 2.5 molar equivalents of hydrogen were consumed and the resulting olefinic mixture consists essentially of monoenes and unconjugated dienes, with less than about 10% trienes, and no detectable amount of alkane or conjugated diene.

The amount of hydrogen, catalyst, catalyst loading, and reaction conditions (reaction temperature, hydrogen pressure and time) can be independently varied in the second stage relative to the first stage to partially hydrogenate the olefinic intermediate product to produce a desired olefinic feedstock. For example, if a mono-olefinic feedstock is desired, the catalyst and catalysis conditions in the second stage may be selected to preferentially hydrogenate unconjugated polyenes over monoenes. In one example, hydrogen pressure and temperature are reduced in the second stage so as to favor hydrogenation of unconjugated polyenes over monoenes.

Although certain staged hydrogenation processes for a conjugated hydrocarbon terpene comprising at least one additional olefinic bond (e.g., α-farnesene or β-farnesene) may include three or more distinct hydrogenation stages, in some variations, a two stage hydrogenation process is used to produce an olefinic feedstock. In the first hydrogenation stage, catalysis conditions are such that at least one olefinic bond in the conjugated diene moiety is preferentially hydrogenated and sufficient hydrogen is delivered (e.g., at least about 1-1.5 molar equivalent of hydrogen, or in some cases about 2-2.5 molar equivalents of hydrogen) so that the quantity of conjugated diene remaining is low, e.g., less than about 10%, less than about 5%, less than about 2%, or less than about 1%. Hydrogenation conditions in the first stage may be relatively mild (e.g., temperature is in a range from about 40° C. to about 110° C.) so that essentially no alkane is formed and essentially no competing reactions (e.g., thermal dimerization, cyclization, isomerization, and the like) occur. In certain variations, about one molar equivalent of hydrogen is consumed and catalyst and catalyst conditions are selected so that the intermediate olefinic product produced after the first stage consists essentially of unconjugated polyenes (e.g., unconjugated trienes in the case of farnesene). In certain variations, the amount of hydrogen, catalyst and catalysis conditions (catalyst loading, temperature, hydrogen pressure and reaction time) are selected so that the intermediate product produced after the first stage consists predominantly of monoenes and unconjugated polyenes (monoenes and unconjugated dienes in the case of farnesene), e.g., at least about 80%, at least about 85%, at least about 90%, at least about 95% unconjugated polyenes, with little or no alkane and little or no conjugated diene.

In the second hydrogenation stage, the amount of hydrogen, the catalyst and the catalysis conditions (catalyst loading, hydrogen pressure, temperature and/or reaction time) may be selected based on the intermediate distribution of species formed in the first stage to produce a desired final distribution of species. For example, if the first stage produced an intermediate product consisting essentially of monoenes and unconjugated polyenes (e.g., monoenes and dienes in the case of farnesene), and a mono-olefinic feedstock is desired, catalysis conditions of the second stage may be tuned to selectively hydrogenate the unconjugated polyenes rather than the mono-olefins so as to produce a feedstock consisting of predominantly mono-olefins, e.g., at least about 60%, at least about 65%, at least about 70%, at least about 75%, at least about 80%, at least about 85%, at least about 90%, or at least about 95% monoolefins, and the amount of alkane produced is limited (e.g., to less than about 25%, less than about 20%, less than about 15%, less than about 10%, or less than about 5%). Certain Examples herein provide nonlimiting examples of two-stage partial hydrogenations of β-farnesene to produce mono-olefinic feedstocks.

In some variations, the temperature of a first hydrogenation stage of a conjugated hydrocarbon terpene (e.g., myrcene, ocimene, α-farnesene or β-farnesene) may be kept low (e.g., kept below about below about 120° C., below about 100° C., or below about 80° C., below about 50° C., or below about 40° C.) to preferentially hydrogenate at least one olefinic bond in the conjugated diene moiety over other olefinic bonds and to reduce occurrence of competing processes (e.g., thermal dimerization, cyclization, isomerization, and the like). After forming an intermediate partially hydrogenated product in which at least one olefinic bond in the conjugated diene moiety has been preferentially hydrogenated, catalysis conditions for a second stage may be selected to preferentially hydrogenate unconjugated polyenes (e.g., di-olefins and tri-olefins in the case of farnesene) over mono-olefins, without creating undesired amounts of completely saturated alkane. For example, a second hydrogenation stage may be conducted at a higher temperature (e.g. at least about 50° C., at least about 100° C., or at least about 150° C. higher than a first hydrogenation stage) to favor hydrogenation of unconjugated polyenes over mono-olefins, thereby enriching the population of mono-olefins in the final partially hydrogenated product. Since the conjugated diene moiety has been eliminated or reduced to a very low concentration by the first stage, probability of thermal dimerization or other competing reactions associated with the conjugated diene are greatly reduced, even at higher temperatures. In certain variations, the catalyst and catalyst loading are kept constant between the first and second stages, but the temperature is increased in the second stage relative to the first stage, e.g., as described here.

In some variations, a metal catalyst such as palladium, platinum, nickel, copper, copper-chromium, rhodium, ruthenium or molybdenum on various supports may be used in the second or subsequent hydrogenation stages. Nonlimiting examples of palladium-containing catalysts that can be used in the second hydrogenation stage are Pd/C, Pd/Al$_2$O$_3$, Pd/titanium silicate, Pd/SiO$_2$, Pd on titania, Pd on zirconia, and Pd on alumina-silica. In some variations, a catalyst used in a second or subsequent stage is activated before use. For example, some copper-containing catalysts (e.g., Cu/SiO$_2$ or a Cu—Cr catalyst) is activated before use (e.g., at 150-180° C.). In some cases, a metal catalyst known in the art for preferentially hydrogenating di-olefins or higher polyenes over mono-olefins is used in the second or subsequent stages.

In some variations, reaction conditions in latter hydrogenation stage are selected to favor dehydrogenation of paraffins. For example, temperature is increased and hydrogen pressure is reduced in a final hydrogenation stage so as to favor dehydrogenation of paraffins, without formation of undesired side products.

In some variations, a second hydrogenation stage may be conducted at a lower hydrogen pressure (e.g., a second stage hydrogen pressure of about 10-100 psig, such as about 10, 20, 30, 40, 50, 60, 70, 80, 90 or 100 psig) than the hydrogen pressure of a first stage to favor hydrogenation of unconjugated polyenes (e.g., di-olefins and tri-olefins in the case of farnesene) over mono-olefins. In some variations, the hydrogen pressure in the second stage is below 50 psig, e.g., about 10, 20, 30, or 40 psig. In some variations, a second hydrogenation stage may be conducted at a higher temperature (e.g., at least about 50° C., 100° C., or 150° C. higher than a first hydrogenation stage) and at a lower hydrogen pressure (e.g. at a pressure that is 10-990 psig lower than pressure in a first stage). In certain variations, the catalyst and catalyst loading are kept constant between the first and second stages, but the temperature is increased in the second stage relative to the first stage and the hydrogen pressure is lowered in the second stage relative to the first stage, e.g., as described here. In some variations, the temperature of the first stage is in a range from about 40° C. to about 160° C. and the hydrogen pressure in the first stage is in a range from about 100 psig to about 1000 psig, and the temperature in the second stage is in a range from about 120° C. to about 260° C. and the hydrogen pressure in the second stage is in a range from about 10 psig to about 100 psig.

In some variations, a staged partial hydrogenation process includes more than two temperature stages, e.g., three, four, five, or more temperature regimes. In some variations, a first temperature stage involves no external heating, and self-heat is provided by the exotherm of the hydrogenation reaction. In some variations, a staged partial hydrogenation process includes a first self-heated stage during which about 0.5 equivalents or less of hydrogen is added (e.g., about 0.3-0.5 equivalents of hydrogen), followed by a second temperature stage during which the temperature is raised (e.g., to about 80-110° C., such as about 80° C., 90° C., 100° C., or 110° C.) and the total hydrogen equivalents added is raised to about 1.5 (e.g., additional 1-1.2 equivalents), followed by a third stage during which an additional 1.5 equivalents hydrogen is added and the temperature is raised to about 160-240° C., e.g., about 160° C., 170° C., 180° C., 190° C., 200° C., 210° C., 220° C., 230° C., or 240° C.). In some cases, the hydrogen pressure is maintained at a relatively constant pressure (e.g., a pressure of about 50-200 psig, such as about 50, 100, 150 or 200 psig) throughout all three stages. In some variations, the hydrogen pressure is maintained (e.g., at about 50-200 psig for the first self-heating stage and the second stage (e.g., a pressure of about 50-200 psig, such as about 50, 100, 150 or 200 psig), and the hydrogen pressure is reduced during the third stage to a pressure less than about 50 psig (e.g., about 5, 10, 15, 20, 25, 30, 35, or 40 psig).

In some variations, a staged hydrogenation process comprises a first self-heat stage during which about 0.5 equivalents or less of hydrogen is added (e.g., about 0.3-0.5 equivalents), a second stage during which about 1-1.2 equivalents of hydrogen is added and the temperature is about 100° C., and a third stage during which about 1.5 equivalents of hydrogen is added and the temperature is about 160° C., where the hydrogen pressure is not varied (e.g., held at about 50 psig, 100 psig, 150 psig, or 200 psig). In one variant, the hydrogen pressure is about 100 psig throughout the hydrogenation process.

In one embodiment, a staged hydrogenation process comprises a first self-heat stage during which about 0.5 equivalents or less of hydrogen is added (e.g., about 0.3-0.5 equivalents) and the hydrogen pressure is about 50-200 psig (e.g., about 50, 100, 150, or 200 psig), a second stage during which about 1-1.2 equivalents of hydrogen is added and the temperature is about 100° C. and the hydrogen pressure is maintained as in the self-heat stage, and a third stage during which the temperature is increased to about 160-240° C. (e.g., about 160° C., 170° C., 180° C., 190° C., 200° C., 210° C., 220° C., 230° C. or 240° C.) and the hydrogen pressure is decreased to a pressure less than about 50 psig (e.g., about 5, 10, 15, 20, 25, 30, 35, or 40 psig). In one variant, the pressure in the first self-heat stage and the second stage is about 100 psig, the temperature in the third stage is about 210° C., and the hydrogen pressure in the third stage is about 20 psig or lower.

Nonlimiting examples of temperature and hydrogen pressure hydrogenation conditions for a first hydrogenation stage in which about 1-2.5 (e.g., about 1-1.5, or about 2-2.5) equivalents of hydrogen are consumed to selectively hydrogenate the conjugated diene are provided in Table 1A. It should be noted that the first hydrogenation stage may or may not be preceded by a self-heated hydrogenation stage as described above. Each "X" in Table 1A discloses reaction conditions comprising the temperature indicated in the column heading and the hydrogen pressure indicated in the row headings. Nonlimiting examples of catalysts that may be used together with the temperatures and hydrogen pressure combinations indicated in Table 1A include Pd/C (e.g., 5-10 wt % Pd), Pd/Al$_2$O$_3$ (e.g., 0.2-0.6 wt % Pd), Pd/SiO$_2$ (e.g., 0.2-0.6 wt % Pd), and Lindlar's catalyst.

TABLE 1A

| | | Temperature (° C.) | | | | | | | | | | | | | |
|---|---|---|---|---|---|---|---|---|---|---|---|---|---|---|
| | | 50 | 55 | 60 | 65 | 70 | 75 | 80 | 85 | 90 | 100 | 105 | 110 | 115 | 120 |
| Hydrogen pressure (Psi) | 50 | X | X | X | X | X | X | X | X | X | X | X | X | X | X |
| | 100 | X | X | X | X | X | X | X | X | X | X | X | X | X | X |
| | 150 | X | X | X | X | X | X | X | X | X | X | X | X | X | X |
| | 200 | X | X | X | X | X | X | X | X | X | X | X | X | X | X |
| | 250 | X | X | X | X | X | X | X | X | X | X | X | X | X | X |
| | 300 | X | X | X | X | X | X | X | X | X | X | X | X | X | X |
| | 350 | X | X | X | X | X | X | X | X | X | X | X | X | X | X |
| | 400 | X | X | X | X | X | X | X | X | X | X | X | X | X | X |
| | 450 | X | X | X | X | X | X | X | X | X | X | X | X | X | X |
| | 500 | X | X | X | X | X | X | X | X | X | X | X | X | X | X |
| | 550 | X | X | X | X | X | X | X | X | X | X | X | X | X | X |
| | 600 | X | X | X | X | X | X | X | X | X | X | X | X | X | X |
| | 650 | X | X | X | X | X | X | X | X | X | X | X | X | X | X |
| | 700 | X | X | X | X | X | X | X | X | X | X | X | X | X | X |
| | 750 | X | X | X | X | X | X | X | X | X | X | X | X | X | X |
| | 800 | X | X | X | X | X | X | X | X | X | X | X | X | X | X |
| | 850 | X | X | X | X | X | X | X | X | X | X | X | X | X | X |
| | 900 | X | X | X | X | X | X | X | X | X | X | X | X | X | X |
| | 950 | X | X | X | X | X | X | X | X | X | X | X | X | X | X |
| | 1000 | X | X | X | X | X | X | X | X | X | X | X | X | X | X |

Nonlimiting examples of hydrogenation conditions for a second hydrogenation stage after about 1-2.5 (e.g., about 1-1.5, or about 2-2.5) equivalents of hydrogen have already been consumed by the conjugated alkene are provided in Table 1B. Each "X" in Table 1B discloses reaction conditions comprising the temperature indicated in the column heading and the hydrogen pressure indicated in the row headings. Nonlimiting examples of catalysts that may be used together with the temperatures and hydrogen pressure combinations indicated in Table 1B include catalysts comprising Pt, Pd, Ni, Cu, Rh, Ru, and Mo on various supports, such as Pd/C (e.g., 5-10 wt % Pd), Pd/Al$_2$O$_3$ (e.g., 0.2-0.6 wt % Pd), Pd/SiO$_2$ (e.g., 0.2-0.6 wt % Pd), Cu-based catalyst (e.g., Cu/SiO2), zeolites impregnated or exchanged with noble metals (e.g., Pd or Pt), and Pt(S)/C. In some variations, the catalyst used for a second hydrogenation stage after about 1-2.5 equivalents of hydrogen have been consumed by the conjugated alkene is 0.3 wt % Pd/Al$_2$O$_3$, and the temperature is about 200-210° C. and the hydrogen pressure is about 1 bar (14 psi). For low hydrogen pressures (e.g., hydrogen pressures lower than about 2 bar), an inert gas such as dry nitrogen may be added to the reactor to increase the overall pressure while achieving a desired partial pressure of hydrogen.

TABLE 1B

| | | Temperature (° C.) | | | | | | | | | | | | | | |
|---|---|---|---|---|---|---|---|---|---|---|---|---|---|---|---|
| | | 120 | 130 | 140 | 150 | 160 | 170 | 180 | 190 | 200 | 210 | 220 | 230 | 240 | 250 | 260 |
| Hydrogen pressure (Psi) | 5 | X | X | X | X | X | X | X | X | X | X | X | X | X | X | X |
| | 10 | X | X | X | X | X | X | X | X | X | X | X | X | X | X | X |
| | 15 | X | X | X | X | X | X | X | X | X | X | X | X | X | X | X |
| | 20 | X | X | X | X | X | X | X | X | X | X | X | X | X | X | X |
| | 25 | X | X | X | X | X | X | X | X | X | X | X | X | X | X | X |
| | 30 | X | X | X | X | X | X | X | X | X | X | X | X | X | X | X |
| | 35 | X | X | X | X | X | X | X | X | X | X | X | X | X | X | X |
| | 40 | X | X | X | X | X | X | X | X | X | X | X | X | X | X | X |
| | 45 | X | X | X | X | X | X | X | X | X | X | X | X | X | X | X |
| | 50 | X | X | X | X | X | X | X | X | X | X | X | X | X | X | X |

A hydrogenation process may comprise any combination of first stage temperature and hydrogen pressure conditions disclosed in Table 1A with second stage temperature and hydrogen pressure conditions described in Table 1B, with the proviso that the combination selected yields the desired selectivity, yield and reaction time. As described above, in some variations, the temperature in the second stage is higher than in the first stage. In some variations, the hydrogen pressure is lower in the second stage than in the first stage. In some variations, the temperature is higher and the hydrogen pressure is lower in the second stage relative to the first stage.

If farnesene is being selectively hydrogenated, after the addition of 1-2.5 equivalents of hydrogen in a first stage, in a second or subsequent stage temperature is increased so as to favor the hydrogenation of di-olefin to form mono-olefin (k[3]) over the hydrogenation of mono-olefin to form saturated hydrocarbon (k[4]). The reaction temperature in a second or subsequent stage may be increased by about 50-150° C., e.g., by about 50° C., by about 60° C., by about 70° C., by about 80° C., by about 90° C., by about 100° C., by about 110° C., by about 120° C., by about 130° C., by about 140° C., or by about 150° C. In some variations, after the addition of 1-1.5 equivalents of hydrogen to farnesene in a first stage, in a second or subsequent stage hydrogen pressure is decreased so as to favor the reaction of di-olefin to form mono-olefin (k[3]) over the reaction of mono-olefin to form saturated hydrocarbon (k[4]). Without being bound by theory, reducing hydrogen pressure in the reactor limits the availability of hydrogen, which leads to favoring the reaction of di-olefin to form mono-olefin over the reaction of mono-olefin to form saturated hydrocarbon. The hydrogen pressure in a second or subsequent stage may be decreased by about 50-100 psig, e.g., by about 50 psig, about 60 psig, about 70 psig, about 80 psig, about 90 psig, or about 100 psig. In some variations, after the addition of 1-2.5 equivalents of hydrogen to farnesene in a first stage, in a second or subsequent stage temperature is increased and hydrogen pressure is decreased so as to favor the reaction of di-olefin to form mono-olefin (k[3]) over the reaction of mono-olefin to form saturated hydrocarbon (k[4]). The reaction temperature in a second or subsequent stage may be increased by about 50-150° C. (e.g., by about 50° C., about 60° C., about 70° C., about 80° C., about 90° C., about 100° C., about 120° C., or about 150° C.), and the hydrogen pressure in a second or subsequent stage may be decrease by about 50-100 psig (e.g., decreased by about 50 psig, about 60 psig, about 70 psig, about 80 psig, about 90 psig, or about 100 psig).

Figure 7A:
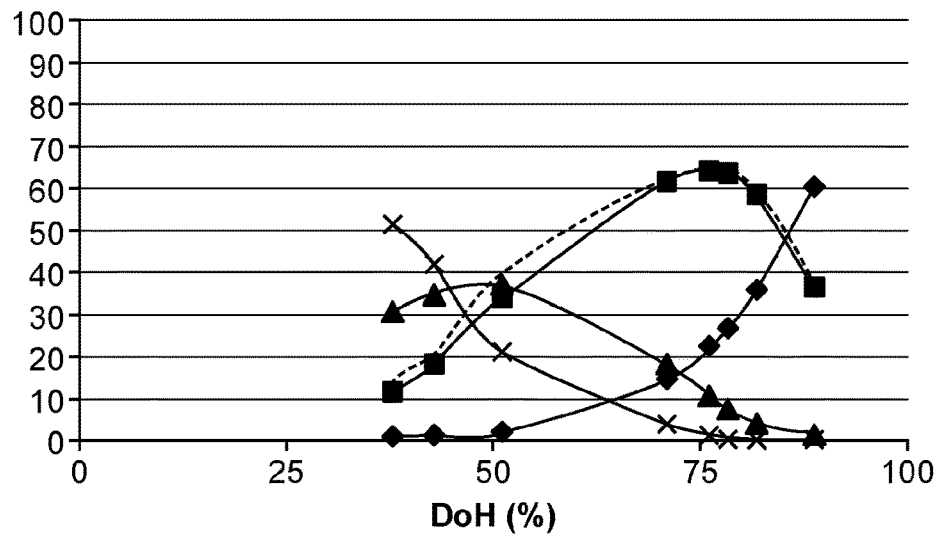
FIGS. 7A-7C provides graphs of populations of various species as hydrogenation proceeds in a second stage for Example 34. Second stage hydrogenation conditions for the data shown in FIG. 7A are 200° C., 2 bar hydrogen pressure; second stage hydrogenation conditions for the data shown in FIG. 7B are 200° C., 1 bar hydrogen pressure; second stage hydrogenation conditions for the data shown in FIG. 7C are 200° C., 0.5 bar hydrogen pressure. "X" represents farnesene content, solid squares represent mono-olefin content, solid triangles represent di-olefin content, and solid diamonds represent farnesane content.
Figure 7B:
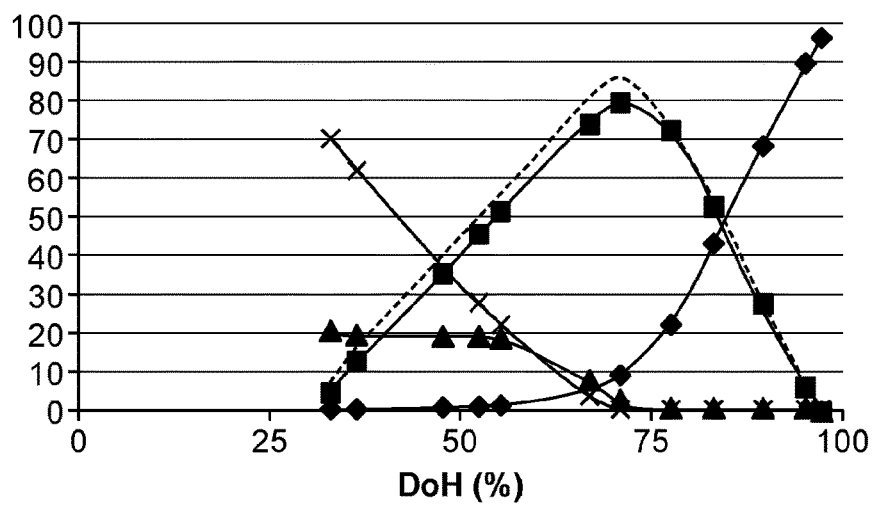
Figure 7C:
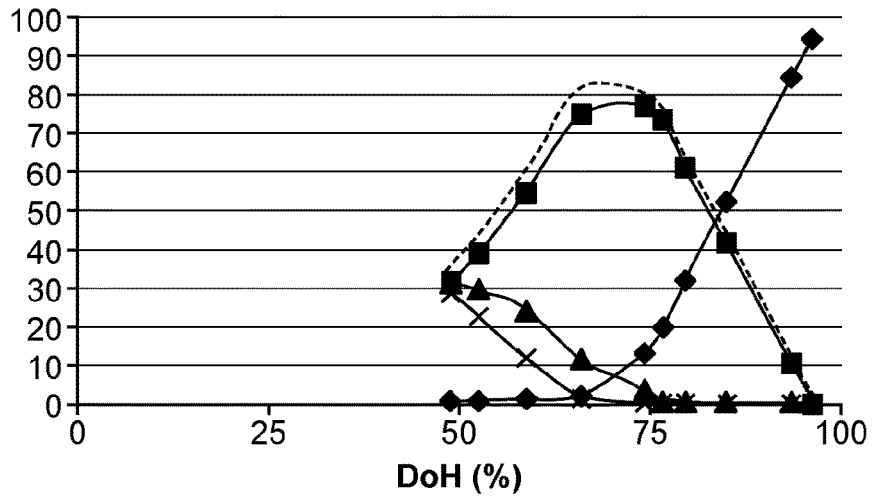

Although nominally the degree of hydrogenation to produce a mono-olefinic hydrocarbon terpene is adjusted to be about one hydrogen equivalent less than total hydrogenation (e.g., 75% hydrogenated for farnesene), the degree of hydrogenation is fine tuned to achieve a desired balance between mono-olefinic content, di-olefinic content and alkane content. In some variations, a desired balance is achieved when the degree of hydrogenation is slightly less than about one hydrogen equivalent less than total hydrogenation (e.g., slightly less than 75% for farnesene). Using farnesene as a model compound, as shown in FIGS. 7A-7C, it is possible to monitor the relative populations of each species as the total degree of hydrogenation proceeds and to identify a degree of hydrogenation at which a desired balance between mono-olefinic, di-olefinic, and alkane content is achieved. In some applications, it may be desired to maximize ratio mono-olefin:di-olefin. In some applications, it may be desired to maximize mono-olefin. As shown in FIG. 7A, under certain temperature and pressure conditions in a second stage, the hydrogenation degree at which mono-olefin is maximum occurs with a total degree of hydrogenation that is about 75% or slightly higher than 75%, and at a point at which alkane content has started to rise. Under these conditions, di-olefin content is not substantially reduced until alkane content has started to rise. Referring now to FIGS. 7B-7C, under other temperature and pressure conditions in a second stage, a degree of hydrogenation can be identified at which mono-olefin content is maximized before alkane content begins to rise steeply, and at a point at which di-olefin content has been substantially reduced. In the examples shown in FIGS. 7B and 7C, the degree of hydrogenation at which olefin content is maximized while both alkane and di-olefin content are minimized occurs at a degree of hydrogenation that is slightly lower than 75%, e.g., at about 70-74.5%, or about 70%, 70.5%, 71%, 72%, 72.5%, 73%, 73.5%, 74%, or 74.5% hydrogenated.

In some variations, hydrogenation conditions are adjusted so that the mono-olefin:di-olefin ratio is about 10:1 or greater, about 20:1 or greater, about 30:1 or greater, about 40:1 or greater, about 50:1 or greater, about 60:1 or greater, about 70:1 or greater, about 80:1 or greater, about 90:1 or greater, about 100:1 or greater, about 120:1 or greater, about 140:1 or greater, about 160:1 or greater, about 180:1 or greater, about 200:1 or greater, about 220:1 or greater, about 240:1 or greater, about 260:1 or greater, about 280:1 or greater, about 300:1 or greater, about 320:1 or greater, about 340:1 or greater, about 360:1 or greater, about 380:1 or greater, about 400:1 or greater, about 500:1 or greater, about 1000:1 or greater, or even greater.

Any suitable configuration for staged partial hydrogenation may be used to carry out the methods described herein. The catalysis conditions (structure of catalyst, type of catalyst, catalyst loading, reaction time, temperature and/or hydrogen pressure) of the first stage, second stage (and subsequent stages, if present) may be independently varied. In some variations, the hydrogenation may be conducted in a single reactor such that the catalyst is not changed between stages. In some variations, the hydrogenation may be conducted in one or more serial reactors so that the catalyst used in different stages may be different. If a single reactor is used for a multi-stage hydrogenation, a batch reactor (e.g., batch slurry reactor) or fixed bed or flow through type reactor may be used. If a batch reactor is used, any suitable type of batch reactor may be used, e.g., a batch slurry reactor.

If a fixed bed or flow through reactor, any suitable type of fixed bed or flow through type reactor may be used. In a flow through reaction, efficient heat transfer to the hydrocarbon terpene and residence time in certain temperature zones are important for effective staged hydrogenation reaction to achieve desired selective hydrogenation as described herein. The reactor operates safely while removing exothermic heat due to the hydrogenation, and while controlling temperature in the desired ranges. In some variations, diameters of fixed bed reactors are limited to allow control of the exotherm and overall temperature control of the reactor. It is desired to tune reaction conditions to avoid formation of thermal dimers. Temperature in a first stage is limited to avoid formation of thermal dimers. Further, dilution by a diluent may be used limit formation of thermal dimers. Thermal dimer formation is second order with respect to terpene concentration, whereas hydrogenation rates are typically between zero order and first order with respect to the terpene, so that dilution by a diluent generally increases the ratio of hydrogenation rate to dimerization rate. Any suitable dilution is used, e.g., about 1:100, 1:50, 1:20, 1:10, 1:5, 1:4, 1:3, 1:2, 1:1, 2:1, 3:1, 4:1, 5:1, or 10:1 terpene:diluent. In some cases, the terpene is diluted about 25% in a diluent. In some variations, use of a higher first stage temperature is possible if sufficient dilution is used to limit formation of dimers. Residence times are adjusted so that the reactants experience hydrogenation conditions in the desired temperature and pressure range. Catalyst activity may be balanced such that activity is high enough to allow desired throughput rates but not so high as to produce undesired amounts of saturated alkane or to induce isomerization. In some variations, the hydrocarbon terpene is carried through the flow reactor in a liquid diluent to provide heat transfer between reactor walls and the terpene. The liquid diluent is selected to consume no hydrogen, to be inert under the reaction conditions, and to provide efficient thermal transfer between the terpene substrate and the source of heat in the reactor. In some variations, a suitable liquid diluent may have a higher boiling point than the terpene, such as a high boiling PAO (e.g., Durasyn® PAOs, such as Durasyn® 164, available from Ineos Oligomers, League City, Tex.), a higher boiling terpene oil (e.g., squalane). In some variations, the hydrocarbon terpene is carried through the flow reactor in an inert solvent such as toluene or heptane. A liquid diluent may be selected to be easily separated from the product, e.g., by distillation. In some variations, the hydrocarbon terpene is carried through the flow reactor in a gaseous diluent, e.g., excess hydrogen.

The multiple stage hydrogenation as described herein may be adapted to a variety of different reactor configurations. In some variations, multiple catalyst beds are used with interstage coolers. In some variations, a multiple tube reactor is used. In some variations, a continuous slurry reactor is used. In some variations, a fluidized bed reactor is used.

Figure 6:
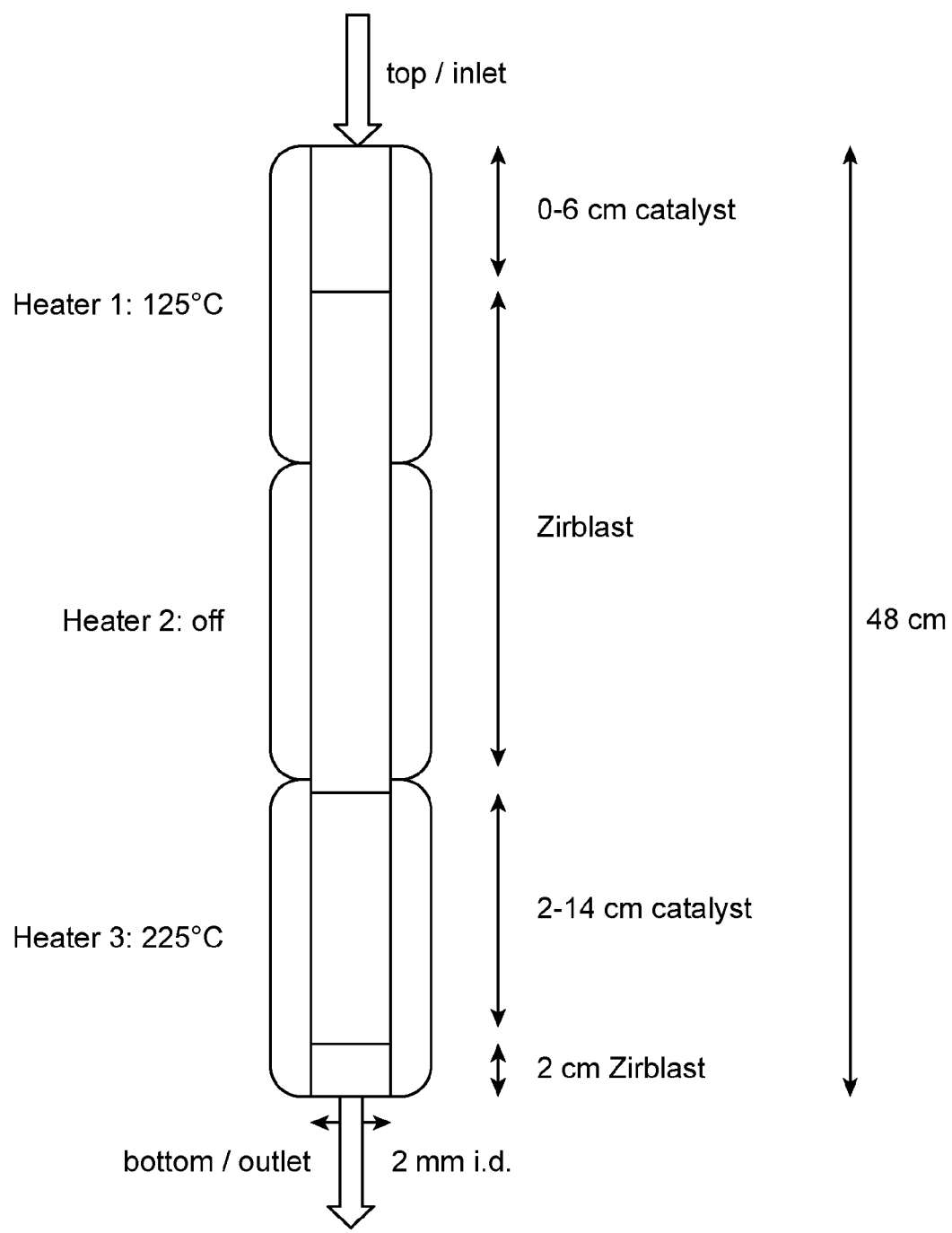
FIG. 6 provides a diagram of a fixed bed reactor used in Example 32.

In some variations, multiple hydrogenation stages are configured as multiple zones in a fixed bed reactor. One non-limiting example of a multi-stage hydrogenation process adapted to a flow through reactor is illustrated in FIG. 6 and provided in Example 32. If multiple reactors are used in a multi-stage hydrogenation, any combination of batch reactors and fixed bed or flow through type reactors may be used.

In some variations, the multi-stage hydrogenation is carried out in a batch reactor (e.g., batch slurry reactor), or in a series of more than one batch reactors, wherein one or more stages (e.g. a first stage) is carried out in a first batch reactor and one or more subsequent stages (e.g. a second stage) is carried out in a second batch reactor, and so on. In some variations, at least one stage (e.g. a first stage or a final stage) of a multi-stage hydrogenation is carried out in a fixed bed or flow through type reactor. In some variations, more than one stage (e.g., all stages) of a multi-stage hydrogenation is carried out in a fixed bed or flow through type reactor. In some variations, a first stage of a multi-stage hydrogenation is carried out in a fixed bed or flow through type reactor and a second or subsequent stage is carried out in a batch reactor. In some variations, a first stage of a multi-stage hydrogenation is carried out in a batch reactor and a second or subsequent stage is carried out in a fixed bed or flow through type reactor.

In some variations, the same catalyst is used in a first and subsequent stages, but the reaction time. temperature and/or hydrogen pressure is varied in the second or subsequent stages. In some variations, the temperature of the first stage is lower than the temperature of the second or subsequent stage, e.g. the temperature of the first stage is at least about 50° C., 75° C., 100° C., or 150° C. lower than the temperature of a second or subsequent stage. In some variations, the partial hydrogenation is conducted in three or more stages, and the temperature is increased with each stage, e.g., by at least about 50° C. In some variations, the temperature is increased with each stage, but the hydrogen pressure is maintained to be about the same in second and subsequent stages. In some variations, the hydrogen pressure of the first stage is higher than the pressure of the second or subsequent stage, e.g., the hydrogen pressure of the first stage is about 10-500 psig, or about 20-500 psig higher than the hydrogen pressure of the second or subsequent stage. In some variations, the temperature is increased with each stage and the hydrogen pressure is decreased with each stage. In some variations, the loading of the catalyst is varied between a first stage and a subsequent stage. In some variations, the same catalyst is used in first and second stages, and hydrogen pressure in the first stage is in a range from about 50 psig to about 500 psig (e.g., about 50, 100, 200, 300, 400, or 500 psig) and the temperature in the first stage is in a range from about 40° C. to about 160° C. (e.g., about 40° C., 50° C., 60° C., 70° C., 80° C., 90° C., 100° C., 110° C., 120° C., 130° C., 140° C., 150° C., or 160° C.), and the hydrogen pressure in the second stage is in a range from about 10 psig to about 50 psig (e.g., about 10, 20, 30, 40, or 50 psig) and the temperature in the second stage is in a range from about 180° C. to about 260° C. (e.g., about 180° C., 200° C., 220° C., 240° C., or 260° C.). In some variations, the same catalyst is used in the first and second stages, and the same hydrogen pressure is used in the first and second stages, but the temperature is increased in the second stage relative to the first stage, e.g., the temperature in the second stage may be about 50° C.-150° C. higher than the first stage. In one variation, the catalyst and hydrogen pressure are kept constant between the first and second stages, the temperature in the first stage is about 40° C.-80° C. (e.g., about 40° C., 50° C., 60° C., 70° C., or 80° C.) and the temperature in the second stage is in a range from about 100° C. to about 200° C. (e.g., about 100° C., 120° C., 140° C., 160° C., 180° C., or 200° C.).

In some variations, the catalysis conditions (structure of catalyst, type of catalyst, catalyst loading, reaction time, temperature and/or hydrogen pressure) are selected so that the total degree of hydrogenation after a first stage is about 20%, 25%, 30%, 35%, 40%, 45%, 50%, 55%, 60%, 65%, or 70%. In some variations, the catalysis conditions are selected so that the total degree of hydrogenation after a final stage (e.g. after a second stage in a two-stage hydrogenation) is about 50%, 55%, 60%, 65%, 70%, 75% or 80%. In some variations, the catalysis conditions are selected so that the total degree of hydrogenation after a first stage is about 20-70% (e.g., about 20%, 25%, 30%, 35%, 40%, 45%, 50%, 55%, 60%, 65% or 70%), and the total degree of hydrogenation after a final stage is about 50-80% (e.g., about 50, 55%, 60%, 65%, 70%, 75% or 80%).

In some variations, the catalysis conditions (structure of catalyst, composition of catalyst, catalyst loading, reaction time, temperature and/or hydrogen pressure) of a first hydrogenation stage are selected to hydrogenate the sample so that at least one olefinic bond in the conjugated diene is selectively hydrogenated. For example, catalysis conditions in a first stage may be selected so that there is less than about 10% starting material (e.g., about 9%, 8%, 7%, 6%, 5%, 4%, 3%, 2%, 1%, 0.5%, 0.3%, less than 0.3%, or no detectable amount as measured by GC-MS). In some variations, the conjugated diene species is effectively eliminated (e.g., so that the amount of species having a conjugated diene less than about 5%, such as about 3%, 2%, 1%, 0.5%, 0.3% or an undetectable amount by GC-MS in a first stage of the hydrogenation, so that the temperature of a second or subsequent stage may be increased without causing significant thermal dimerization. For example, in the case of farnesene, if the conjugated diene species remaining after the first stage is less than about 5%, the temperature of a second or subsequent stage may be increased to be 160° C. or higher, e.g., about 160° C., 170° C., 180° C., 190° C., 200° C., 210° C., 220° C., 230° C., 240° C., 250° C., or 260° C., without forming significant amounts of thermal dimers.

In some variations, a first stage of the hydrogenation produces less than about 10% of the completely hydrogenated alkane (e.g., about 9%, 8%, 7%, 6%, 5%, 4%, 3%, 2%, 1%, 0.5%, 0.3%, less than 0.3%, or no detectable amount as measured by GC/MS). In some variations, in a first stage of the hydrogenation, the catalysis conditions are selected such that there is less than about 10% starting material (e.g., about 9%, 8%, 7%, 6%, 5%, 4%, 3%, 2%, 1%, 0.5%, 0.3%, less than 0.3%, or no detectable amount as measured by GC/MS) and there is less than about 10% of the completely hydrogenated alkane (e.g., about 9%, 8%, 7%, 6%, 5%, 4%, 3%, 2%, 1%, 0.5%, 0.3%, less than 0.3%, or no detectable amount as measured by GC/MS).

If a feedstock comprising predominantly mono-olefins is desired, the catalysis conditions (catalyst composition, catalyst structure, reaction time, temperature and/or hydrogen pressure) of a first stage may be selected to produce a mixture comprising predominantly mono-olefins and di-olefins, without producing undesirably high amounts (e.g., greater than about 1%, 3%, 5% or 10%, depending on the application) of completely hydrogenated alkenes or leaving undesirably high amounts (e.g., greater than about 1%, 3%, 5%, or 10%, depending on the application) of starting material. The catalysis conditions of a second stage (catalyst composition, catalyst structure, reaction time, temperature and/or hydrogen pressure) may be selected to preferentially act on the di-olefins over the mono-olefins, thereby enriching the mono-olefin content without creating a concomitant increase in the amount of saturated alkane. For example, the temperature of a second stage may be increased so that the thermodynamics favor hydrogenation of the di-olefin to make a mono-olefin over hydrogenation of the mono-olefin to make saturated alkane.

If a feedstock comprising primarily hexahydrofarnesene is desired, the catalysis conditions (catalyst composition, catalyst structure, reaction time, temperature and/or hydrogen pressure) of a first stage may be selected to produce a mixture comprising predominantly hexahydrofarnesene and tetrahydrofarnesene while producing less than about 10% (e.g., less than 10%, less than 5%, less than 3%, less than 1%, less than 0.5%, or an undetectable amount by GC/MS) farnesene and less than about 10% (e.g., less than 10%, less than 5%, less than 3%, less than 1%, less than 0.5%, or an undetectable amount by GC/MS) farnesane. For example, a catalyst (e.g., a palladium catalyst such as Pd/Al$_2$O$_3$ (e.g., 0.3 wt %) or a Pd/C catalyst (e.g., 5 wt % or 10 wt %) may be used at a temperature in a range of about 80° C.-160° C. and a hydrogen pressure in a range of about 45 psig-1000 psig in a first stage to create an intermediate partially hydrogenated farnesene composition comprising predominantly hexahydrofarnesene and tetrahydrofarnesene, with less than about 5% (e.g., less than about 1% farnesene and less than about 5%) (e.g., less than about 1%) farnesane. A second stage using the same catalyst but higher temperature (e.g., about 200° C. or greater, such as about 200° C., 210° C., 220° C., 240° C. or 260° C.) and a hydrogen pressure lower than the first stage (e.g., a hydrogen pressure of about 10 psig, 20 psig, 30 psig, 40 psig, 50 psig, 60 psig, 70 psig, 80 psig, 90 psig, or 100 psig) can be implemented to preferentially hydrogenate the di-olefin and tri-olefin (if present) and create partially hydrogenated farnesene comprising at least about 70%, 71%, 72%, 73%, 74%, 75%, 76%, 77%, 78%, 79%, 80%, 81%, 82%, 83%, 84%, 85%, 86%, 87%, 88%, 89% or 90% hexahydrofarnesene.

If a feedstock comprising primarily hexahydrofarnesene with limited amounts of tetrahydrofarnesene is desired, the catalysis conditions (catalyst composition, catalyst structure, reaction time, temperature and/or hydrogen pressure) of a first stage may be selected to produce a mixture comprising predominantly hexahydrofarnesene and tetrahydrofarnesene while producing less than about 10% (e.g., less than 10%, less than 5%, less than 3%, less than 1%, less than 0.5%, or an undetectable amount by GC/MS) farnesene and less than about 10% (e.g., less than 10%, less than 5%, less than 3%, less than 1%, less than 0.5%, or an undetectable amount by GC/MS) farnesane. For example, a catalyst (e.g., a palladium catalyst such as Pd/Al$_2$O$_3$ (e.g., 0.3 wt %) or a Pd/C catalyst (e.g., 5 wt % or 10 wt %) may be used at a temperature in a range of about 80° C.-160° C. and a hydrogen pressure in a range from about 45 psig-1000 psig in a first stage to create an intermediate partially hydrogenated farnesene composition comprising predominantly hexahydrofarnesene and tetrahydrofarnesene, with less than about 5% (e.g., less than about 1% farnesene and less than about 5%) (e.g., less than about 1%) farnesane. A second stage using the same catalyst but higher temperature (e.g., about 200° C. or greater, such as about 200° C., 210° C., 220° C., 240° C. or 260° C.) and a hydrogen pressure lower than the first stage (e.g., a hydrogen pressure of about 10 psig, 20 psig, 30 psig, 40 psig, 50 psig, 60 psig, 70 psig, 80 psig, 90 psig, or 100 psig) can be implemented to preferentially hydrogenate the di-olefin and tri-olefin (if present) and create partially hydrogenated farnesene comprising at least about 70%, 71%, 72%, 73%, 74%, 75%, 76%, 77%, 78%, 79%, 80%, 81%, 82%, 83%, 84%, 85%, 86%, 87%, 88%, 89% or 90% hexahydrofarnesene and about 10% or less, 8% or less, 5% or less, 3% or less, 2% or less, 1% or less, or 0.5% or less tetrahydrofarnesene.

In another non-limiting example, controlled staged partial hydrogenation of β-farnesene to produce olefinic feedstocks is carried out as follows. One aliquot hydrogen corresponding to one molar equivalent hydrogen per mol β-farnesene or (two aliquots, each corresponding to about 0.5 mol equivalent H$_2$ per mol β-farnesene), may be delivered to a reactor containing β-farnesene, and the reaction allowed to proceed until the hydrogen is substantially consumed to form 25% hydrogenated β-farnesene. If 50% hydrogenated β-farnesene is desired, two molar equivalents of hydrogen are added, e.g., a first pair of 0.5 mol equivalents of H$_2$ may be delivered to the reactor and allowed to proceed until the hydrogen is substantially consumed, and a second pair of 0.5 mol equivalents of H$_2$ may be delivered to the reactor and allowed to proceed until the hydrogen is substantially consumed. In an example of a staged hydrogenation to form 75% hydrogenated β-farnesene, a first pair of 0.5 mol equivalents of H$_2$ is delivered to the reactor and allowed to proceed until the hydrogen is substantially consumed, a second pair of 0.5 mol equivalents of H$_2$ is delivered to the reactor and allowed to proceed until the hydrogen is substantially consumed in a first stage. In a second stage, the reactor is heated (e.g. to about 100° C.-140° C.) as the heat generated by the exothermic hydrogenation decreases, and a third pair of 0.5 mol equivalents of H$_2$ is delivered to the reactor while the reactor is heated to a temperature of about 100° C.-140° C. and allowed to proceed until the hydrogen is substantially consumed.

In some variations, the methods comprise reacting a controlled amount of hydrogen with a hydrocarbon terpene having a conjugated diene in the presence of a catalyst under controlled (without involving multiples stages) reaction conditions to produce an olefin comprising partially hydrogenated hydrocarbon terpene, wherein the catalyst and reaction conditions are selected to preferentially hydrogenate at least one olefinic bond in the conjugated diene and to preferentially produce mono-olefin species in the olefin comprising the partially hydrogenated hydrocarbon terpene. Some non-limiting examples of β-farnesene that has been partially hydrogenated to produce partially hydrogenated β-farnesene in which hexahydrofarnesene has been preferentially produced with less than 0.3% β-farnesene in a single stage hydrogenation are shown in Examples herein.

In certain variations, a single stage partial hydrogenation process can be used to make an olefinic feedstock rich in a desired species (e.g., mono-olefins) if the catalyst is sufficiently selective, whereas a multi-stage partial hydrogenation process is used in those instances in which the catalyst itself is not particularly selective, but the process conditions (e.g., temperature and/or hydrogen pressure) can be changed between a first stage and a second stage to tune the composition of the final olefinic mixture by choosing process conditions that kinetically and/or thermodynamically favor hydrogenation of certain species over others (e.g., process conditions that favor hydrogenation of polyenes over monoenes to form a mono-olefinic feedstock that comprises limited amounts of alkane).

In some variations, the single stage hydrogenation methods comprise reacting a controlled amount of hydrogen with a hydrocarbon terpene having a conjugated diene in the presence of a catalyst under controlled reaction conditions to produce an olefin comprising partially hydrogenated hydrocarbon terpene, wherein the catalyst and reaction conditions are selected to preferentially hydrogenate one olefinic bond in the conjugated diene and to preferentially produce dihydro hydrocarbon terpene species (with one carbon-carbon double bond reduced). Non-limiting examples are shown in Examples 8-9 herein. The resulting dihydro hydrocarbon terpene species may be used as-is as an olefinic feedstock, or may be further hydrogenated in a second stage (in which one or more of or any combination of catalyst, catalyst loading, temperature and hydrogen pressure may be varied relative to the first stage) to produce an olefinic feedstock.

In some variations, the methods comprise reacting a controlled amount of hydrogen with a hydrocarbon terpene having a conjugated diene in the presence of a catalyst under controlled reaction conditions to produce an olefin comprising partially hydrogenated hydrocarbon terpene, wherein the catalyst and reaction conditions are selected to preferentially hydrogenate one olefinic bond in the conjugated diene and to produce predominantly dihydro hydrocarbon terpene species and tetrahydro hydrocarbon terpene species (e.g., the dihydro and tetrahydro species combined make up at least about 75%, at least about 80%, at least about 85%, at least about 90%, or at least about 95% of the partially hydrogenated product), with less than about 5% (or less than about 1%) conjugated hydrocarbon terpene remaining, and less than about 5% (or less than about 1%) alkane formed. In certain variations, the ratio of dihydro:tetrahydro species in the partially hydrogenated mixture is about 50:50, or 40:60, or 60:40. Non-limiting examples are shown in Examples 1 and 12 herein. The resulting mixture may be used as-is as an olefinic feedstock, or may be further hydrogenated in a second stage (in which one or more of or any combination of catalyst, catalyst loading, temperature and hydrogen pressure may be varied relative to the first stage) to produce an olefinic feedstock. In certain variations, the amount of hydrogen, catalyst and catalyst conditions may be selected in a second hydrogenation stage to selectively hydrogenate the tetrahydro species over the dihydro species to result in a composition rich in dihydro species while minimizing formation of alkane.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a single stage to produce a partially hydrogenated terpene that is rich in mono-olefin and comprises a limited amount of alkane. In some variations, such methods are capable of producing a composition comprising at least about 60% mono-olefin and less than about 25% alkane. In certain variations, the controlled amount of hydrogen, the catalyst, and the reaction conditions are selected to produce an olefin comprising at least about 65% mono-olefin and less than about 20% alkane. In certain variations, the controlled amount of hydrogen, the catalyst, and the reaction conditions are selected to produce an olefin comprising at least about 70% mono-olefin and less than about 20% alkane. In certain variations, the controlled amount of hydrogen, the catalyst, and the reaction conditions are selected to produce an olefin comprising at least about 75% mono-olefin and less than about 15% alkane, or less than about 10% alkane. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a single stage to produce a partially hydrogenated terpene comprising a substantial amount of mono-olefin and a limited amount of di-olefin. In some variations, any di-olefin that is present may be substantially unconjugated, e.g., so that an amount of conjugated species in the composition is about 2% or less or about 1% or less. Such methods may be selected when a feedstock rich in mono-olefins is desired and di-olefins cause undesired side reactions, cross-products, and the like. In some variations, the methods are capable of producing a mono-olefinic feedstock comprising at least about 50% mono-olefin and about 10% or less di-olefin, at least about 50% mono-olefin and about 5% or less di-olefin, at least about 50% mono-olefin and about 3% or less di-olefin, at least about 55% mono-olefin and about 10% or less di-olefin, at least about 55% mono-olefin and about 5% or less di-olefin, at least about 55% mono-olefin and about 3% or less di-olefin, at least about 60% mono-olefin and about 10% or less di-olefin, at least about 60% mono-olefin and about 5% or less di-olefin, at least about 60% mono-olefin and about 3% or less di-olefin, at least about 65% mono-olefin and about 10% or less di-olefin, at least about 65% mono-olefin and about 5% or less di-olefin, at least about 65% mono-olefin and about 3% or less di-olefin, at least about 70% mono-olefin and about 10% or less di-olefin, at least about 70% mono-olefin and about 5% or less di-olefin, at least about 70% mono-olefin and about 3% or less di-olefin, at least about 75% mono-olefin and about 10% or less di-olefin, at least about 75% mono-olefin and about 5% or less di-olefin, at least about 75% mono-olefin and about 3% or less di-olefin, at least about 80% mono-olefin and about 10% or less di-olefin, at least about 80% mono-olefin and about 5% or less di-olefin, at least about 80% mono-olefin and about 3% or less di-olefin, at least about 85% mono-olefin and about 10% or less di-olefin, at least about 85% mono-olefin and about 5% or less di-olefin, at least about 85% mono-olefin and about 3% or less di-olefin. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a multiple stages (e.g., two or more stages) to produce a partially hydrogenated terpene rich in mono-olefin and comprising a limited amount of alkane. In some variations, such methods are capable of producing a partially hydrogenated terpene comprising at least about 60% mono-olefin and less than about 25% alkane. In certain variations, the controlled amount of hydrogen, the catalyst, and the reaction conditions are selected to produce an olefin comprising at least about 65% mono-olefin and less than about 20% alkane. In certain variations, the controlled amount of hydrogen, the catalyst, and the reaction conditions are selected to produce an olefin comprising at least about 70% mono-olefin and less than about 20% alkane. In certain variations, the controlled amount of hydrogen, the catalyst, and the reaction conditions are selected to produce an olefin comprising at least about 75% mono-olefin and less than about 15% alkane, or less than about 10% alkane. In some variations, the hydrocarbon terpene is made by a bioengineered microorganism using a renewable carbon source. At least one of the group consisting of catalyst, catalyst loading, temperature, and hydrogen pressure is varied between a first stage and a subsequent stage of the multi-stage reaction. In some variations, the hydrocarbon terpene is made by a bioengineered microorganism using a renewable carbon source.

In one embodiment, a method for making an olefinic feedstock comprises reacting a controlled amount of hydrogen with a $C_{10}$-$C_{30}$ hydrocarbon terpene (e.g. β-farnesene or α-farnesene) in the presence of a catalyst under controlled reaction conditions in a multiple stages (e.g., two or more stages) to produce a partially hydrogenated terpene rich in mono-olefin and comprising a limited amount of di-olefin. In some variations, such methods are capable of producing a partially hydrogenated terpene comprising a substantial amount of mono-olefin and a limited amount of di-olefin. In some variations, any di-olefin that is present may be substantially unconjugated, e.g., so that an amount of conjugated species in the composition is about 2% or less or about 1% or less. Such methods may be selected when a feedstock rich in mono-olefins is desired and di-olefins cause undesired side reactions, cross-products, and the like. In some variations, the methods are capable of producing a mono-olefinic feedstock comprising at least about 50% mono-olefin and about 10% or less di-olefin, at least about 50% mono-olefin and about 5% or less di-olefin, at least about 50% mono-olefin and about 3% or less di-olefin, at least about 55% mono-olefin and about 10% or less di-olefin, at least about 55% mono-olefin and about 5% or less di-olefin, at least about 55% mono-olefin and about 3% or less di-olefin, at least about 60% mono-olefin and about 10% or less di-olefin, at least about 60% mono-olefin and about 5% or less di-olefin, at least about 60% mono-olefin and about 3% or less di-olefin, at least about 65% mono-olefin and about 10% or less di-olefin, at least about 65% mono-olefin and about 5% or less di-olefin, at least about 65% mono-olefin and about 3% or less di-olefin, at least about 70% mono-olefin and about 10% or less di-olefin, at least about 70% mono-olefin and about 5% or less di-olefin, at least about 70% mono-olefin and about 3% or less di-olefin, at least about 75% mono-olefin and about 10% or less di-olefin, at least about 75% mono-olefin and about 5% or less di-olefin, at least about 75% mono-olefin and about 3% or less di-olefin, at least about 80% mono-olefin and about 10% or less di-olefin, at least about 80% mono-olefin and about 5% or less di-olefin, at least about 80% mono-olefin and about 3% or less di-olefin, at least about 85% mono-olefin and about 10% or less di-olefin, at least about 85% mono-olefin and about 5% or less di-olefin, at least about 85% mono-olefin and about 3% or less di-olefin. In some variations, the hydrocarbon terpene is made by a bioengineered microorganism using a renewable carbon source.

For any of the methods described herein, any suitable hydrogenation catalyst may be used. For example, in some variations, a catalyst used for first and/or subsequent hydrogenation stages is selected from the group consisting of Pd, Pt, Ni, Ru, Ir, Cu, Fe, Raney-type porous catalysts such as Ni/Al, Co/Al and Cu/Al, alloys of platinum group catalysts with promoters or stabilizers such as Mo, Co, Mg and Zn, and hydroprocessing catalysts such as NiMoS and CoMoS. Exemplary catalysts are described in U.S. Pat. Nos. 6,403,844; 5,378,767; 5,151,172; and 3,702,348, each of which is incorporated herein by reference in its entirety. In some variations, the catalyst used for first and/or subsequent hydrogenation stages is or comprises Pd/C, e.g. 5 wt % Pd/C or 10 wt % Pd/C. In some variations, the catalyst for first and/or subsequent hydrogenation stages is or comprises Pd/Al$_2$O$_3$, e.g. 0.3 wt % Pd/Al$_2$O$_3$. In some variations, the catalyst for first and/or subsequent hydrogenation stages is or comprises a Lindlar catalyst, e.g., Pd on calcium carbonate or barium carbonate and treated with lead (e.g., lead oxide or lead acetate). For example, a Lindlar catalyst comprising Pd/Pb/BaCO$_3$ may be used. In some variations, the catalyst for first and/or subsequent hydrogenation stages is or comprises Ni, e.g. Raney Ni, sponge nickel, or skeletal nickel. In some variations, a nickel catalyst is used that is supported by Al$_2$O$_3$, e.g. about 20%, 12% or 8% Ni/Al$_2$O$_3$. In some variations the catalyst used for first and/or subsequent hydrogenation stages comprises nickel sulfide. In some variations, the catalyst used for first and/or subsequent hydrogenation stages comprises molybdenum sulfide, e.g. molybdenum sulfide catalysts having a Mo:S ratio of sulfur to molybdenum, e.g. MoS$_2$ supported on alumina, e.g. activated alumina having a surface area of about 300 square meters per gram or more, or silica gel, activated charcoal, acid treated clay, silica-alumina complexes, e.g. as disclosed in U.S. Pat. No. 2,674,634 which is incorporated by reference herein in its entirety.

For any of the methods described herein, the catalyst can be provided in any suitable form, e.g. with a minimum dimension of at least about 1 mm. Particle dimensions may be selected depending on catalyst type and catalysis conditions (e.g. slurry batch, fixed bed, fluidized bed, or continuous flow reactor). The catalyst may be selected to have a specified surface area to produce the desired distribution of partially hydrogenated hydrocarbon terpene species, and may be formed in any suitable form factor, e.g. cylinders, tablets, granules, spheres, lobed cylinders, and the like. In certain variations, the catalyst contains voids, e.g. in the form of channels, passages, or holes. In some variations, the catalyst used for first and/or subsequent hydrogenation stages comprises a shell type catalyst. In some variations, the catalyst comprises an extrudate, e.g., an extrude having a desired cross-sectional shape, such as a lobed extrude (e.g., trilobe extrudate). In some variations, the catalyst used for first and/or subsequent stages is or comprises Pd/Al$_2$O$_3$, e.g., 0.3 wt % Pd/Al$_2$O$_3$ trilobe extrudate.

A continuous flow reactor scheme may be designed to incorporate the multistage hydrogenation process as described herein. For example, multiple reactors may be placed in series, where the temperature and hydrogen pressure in each reactor are adjusted to reflect the stage of the hydrogenation process. Any of the hydrogenation processes described herein may be adapted to a continuous flow reactor using known techniques for supporting catalysts, selecting appropriate diluents, providing heat and temperature control, providing hydrogen and pressure control, and separation of product from diluents, byproducts, residual starting material and impurities. In some variations, two reactors are placed in series, where the temperature in the first reactor is in a range from about 80° C. to about 110° C. and the hydrogen pressure in the first reactor is in a range from about 50-300 psig, and the temperature in the second reactor is in a range from about 160° C. to about 240° C. and the hydrogen pressure in the second reactor is in a range from about 10-40 psig. In some variations, three reactors are placed in series, where the first reactor is self-heated and the hydrogen pressure in the first reactor is in a range from about 50-300 psig, the temperature in the second reactor is in a range from about 80° C. to about 240° C. and the hydrogen pressure in the second reactor is in a range from about 50-300 psig, and the temperature in the third reactor is in a range from about 160° C. to about 240° C. and the hydrogen pressure in the third reactor is in a range from about 10-40 psig. When multiple reactors are used in series, catalysts used in each of the reactors may be the same or different. For example, in some variations, a catalyst comprising Pd (e.g., Pd/Al$_2$O$_3$) is used in some or all series reactors in a continuous flow reactor scheme. In other variations, the catalyst is different in series reactors in a continuous flow reactor scheme. For example, a catalyst that selectively catalyzes hydrogenation of conjugated dienes may be used in a first reactor in some variations. In some variations, a catalyst that selectively hydrogenates dienes is used in a final reactor. In some variations, a catalyst that selectively catalyzes dehydrogenation of paraffins to form mono-olefins may be used in a final reactor.

In some variations, a single continuous flow reactor with multiple zones in series is used to carry out staged partial hydrogenation as described herein. The temperature and hydrogen pressure and catalyst may each be independently varied between zones to achieve a staged hydrogenation process as described herein within a single reactor. Any multi-zone reactor known in the art may be adapted for this purpose, and known techniques for use of diluents, catalyst support, heating and temperature control, feeding in of hydrogen and pressure control, and separation of products from diluents, reactants, byproducts, impurities and the like may be used. In some variations, a reactor comprises two zones in series, where the temperature in the first zone is in a range from about 80° C. to about 110° C. and the hydrogen pressure in the first zone is in a range from about 50-300 psig, and the temperature in the second zone is in a range from about 160° C. to about 240° C. and the hydrogen pressure in the second zone is in a range from about 10-40 psig. In some variations, a reactor comprises three zones in series, where the first zone is self-heated and the hydrogen pressure in the first zone is in a range from about 50-300 psig, the temperature in the second zone is in a range from about 80° C. to about 240° C. and the hydrogen pressure in the second zone is in a range from about 50-300 psig, and the temperature in the third zone is in a range from about 160° C. to about 240° C. and the hydrogen pressure in the third zone is in a range from about 10-40 psig. When a reactor comprising multiple zones in series is used, catalysts used in each of the zones may be the same or different. For example, in some variations, a catalyst comprising Pd (e.g., Pd/Al$_2$O$_3$) is used in some or all zones in a continuous flow reactor. In other variations, the catalyst is different between zones. For example, a catalyst that selectively catalyzes hydrogenation of conjugated dienes may be used in a first zone, or in first and second zones in some variations. In some variations, a catalyst that selectively hydrogenates dienes is used in a final zone. In some variations, a catalyst that selectively catalyzes dehydrogenation of paraffins to form mono-olefins may be used in a final zone.

It should be understood that in batch reactors or continuous flow reactors implementing the staged hydrogenation process described herein, there may be a gradual or ramped, rather than abrupt, change in temperature and/or hydrogen pressure between the different stages of the hydrogenation process. That is, a continuous process incorporating the multiple stages may be devised.

When the catalyst is used with a support, any suitable support can be used, e.g. carbon, silica, titania, zirconia, alumina, kieselguhr, magnesia, calcium aluminate cements, and other inorganic materials. In some cases, supports are activated. Modified versions of such supports can be used, e.g. base-treated supports or supports treated with stabilizing additives such as MgO. A support can have any suitable form factor (e.g. a pellet or extrudate) with dimensions on the order of about 0.1-5 mm, 0.5-5 mm, 1-5 mm, 1-4 mm, or 1-3 mm.

The hydrogenation catalyst may be used in any effective loading. In some variations (e.g. for 5 wt % Pd/C or 10 wt % Pd/C), an effective catalyst loading may be about 1/50, 1/100, 1/1000, 2/1000, 3/1000, 4/1000, 5/1000, 1/2000, 1/5000, or 1/10000 (ratio refers to weight metal/weight substrate). For example, in some variations β-farnesene can be partially hydrogenated using 5 wt % Pd/C at a loading of 1/10000, 1/7000, 1/6000, 1/5000, 1/4000, 1/3000, 1/2000, 1/1000, 2/1000, 3/1000, 4/1000, or 5/1000. In some variations (e.g., for 0.3 wt % Pd/Al$_2$O$_3$), an effective catalyst loading may be about 1/50, 1/100, 1/200, 1/300, 1/400, 1/500, 1/750, 1/1000, 1/2000, 1/5000, 1/10000 g metal/g substrate, or in a range from about 10-1000 ppm, 10-100 ppm, (e.g., 10-60 ppm), where ppm refers to g metal/g substrate. In some variations (e.g., for 0.3 wt % Pd/Al$_2$O$_3$), an effective catalyst loading may be about 10 ppm, about 12 ppm, about 14 ppm, about 16 ppm, about 18 ppm, about 20 ppm, about 30 ppm, about 40 ppm, about 50 ppm, about 60 ppm, about 70 ppm, about 80 ppm, about 90 ppm, or about 100 ppm in a first or a second hydrogenation stage.

During the partial hydrogenation process, it is desired to deliver a controlled amount of hydrogen under controlled reaction conditions so as to control the extent of and site selectivity of the hydrogenation. Such controlled hydrogenation can be accomplished in a variety of ways, and using a variety of equipment setups. For example, continuous hydrogen uptake by the sample may be controlled and/or measured using a flow meter, flow totalizer, or the like, or hydrogen may be delivered to the sample in discrete or quantized molar aliquots, e.g. discrete aliquots of 0.25, 0.5, or 1 mol H$_2$ per mol hydrocarbon terpene. In some variations, a batch slurry hydrogenation reactor is used. In some variations, a fixed bed reactor is used for partial hydrogenation. In some variations, a fluidized bed reactor is used for partial hydrogenation.

The temperature of the hydrogenation may be selected to control the rate of reaction, which may, in some situations, enhance site selectivity of the hydrogenation. In certain variations, a suitable hydrogenation temperature is in a range from about 40° C. to about 260° C., e.g. about 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., or 260° C. In some variations, the reaction is conducted at about 80° C. In some variations, the reaction is conducted at about 100° C. As described earlier, in some variations, the reaction temperature is varied between a first stage and a subsequent stage. In some variations, the reaction is at least partially self-heated during a first stage when the exothermic reaction is generating sufficient heat, and external heat is added (e.g., to heat the reaction to about 140° C., 150° C. or 160° C.) during a latter stage. In some variations, the reactor is cooled to keep the temperature of the exothermic hydrogenation process under control.

The hydrogen pressure used may be in a range from about 20 psig-1000 psig, e.g. about 20, 30, 40, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1000 psig. As described earlier, in some variations, the hydrogen pressure is varied between a first stage and a subsequent stage of the hydrogenation.

One variation of method for carrying out at least one stage of partially hydrogenating farnesene comprises immersing a catalyst into the liquid hydrocarbon terpene (e.g. β-farnesene) to form a slurry and delivering a controlled amount of hydrogen to the slurry in a closed reactor, where the controlled amount of hydrogen corresponds to a molar equivalent of desired hydrogenation degree. The method comprises hydrogenating the terpene at a temperature between about 50° C. and 260° C. until the controlled amount of hydrogen is substantially consumed, and removing the catalyst from the hydrogenated terpene. For example, in the case of β-farnesene, one molar equivalent of hydrogen delivered to the slurry in the closed reactor corresponds to 25% hydrogenation, two molar equivalents of hydrogen delivered to the slurry in the closed reactor corresponds to 50% hydrogenation, and three molar equivalents corresponds to 75% hydrogenation. The controlled amount of hydrogen may be delivered to the slurry in one or more discrete aliquots or as a continuous stream. In one variation, molar equivalents of hydrogen are delivered to the slurry (e.g. 5 wt % Pd/C at a loading of about 1-5 g/kg hydrocarbon terpene or about 3-5 g/kg hydrocarbon terpene, or 0.3 wt % Pd/Al$_2$O$_3$ at a loading of about 25 mg/20-35 ml hydrocarbon terpene) in the closed reactor in discrete aliquots, e.g. each aliquot corresponding to a known molar equivalent H$_2$ per mol hydrocarbon terpene in the reactor, at a pressure of 20-1000 psig. After each aliquot (or pair of aliquots) is delivered to the reactor, the hydrogenation reaction is allowed to proceed until the hydrogen is substantially consumed. If more extensive hydrogenation is desired, another aliquot (or multiple aliquots) is delivered to the reactor and allowed to proceed until the hydrogen is substantially consumed, and so forth. Following the reaction, the catalyst can be removed from the partially hydrogenated farnesene using known techniques.

In another variation of carrying out at least one stage of a partial hydrogenation, a controlled amount of hydrogen is delivered to a closed reactor in a continuous stream. For example, a catalyst (e.g. 5 wt % Pd/C or 10 wt % Pd/C) is immersed in liquid hydrocarbon terpene (e.g. β-farnesene) to form a slurry in a closed reactor. The reactor is evacuated. Hydrogen is delivered to the reactor (e.g. at about 50 psig), and the cumulative uptake of hydrogen is monitored, e.g. using a flow totalizer or a flow meter. The temperature of the reaction is controlled to control the rate of reaction, e.g. at about 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., or 260° C. When the desired molar equivalent of hydrogen has been consumed (e.g. 3 mol equivalents hydrogen/mol farnesene for 75% hydrogenated farnesene), the hydrogen flow is stopped. Catalyst can be removed from the partially hydrogenated hydrocarbon terpene using known techniques.

Any of the methods described herein can be used to produce a $C_{10}$ olefin comprising partially hydrogenated myrcene, a $C_{10}$ olefin comprising partially hydrogenated ocimene, a $C_{15}$ olefin comprising partially hydrogenated β-farnesene, a $C_{15}$ olefin comprising partially hydrogenated α-farnesene, a $C_{20}$ olefin comprising partially hydrogenated springene, a $C_{25}$ olefin comprising partially hydrogenated geranylfarnesene, a $C_{30}$ olefin comprising partially hydrogenated isodehydrosqualene, or a $C_{30}$ olefin comprising partially hydrogenated isosqualane precursor I or II.

Figure 3:
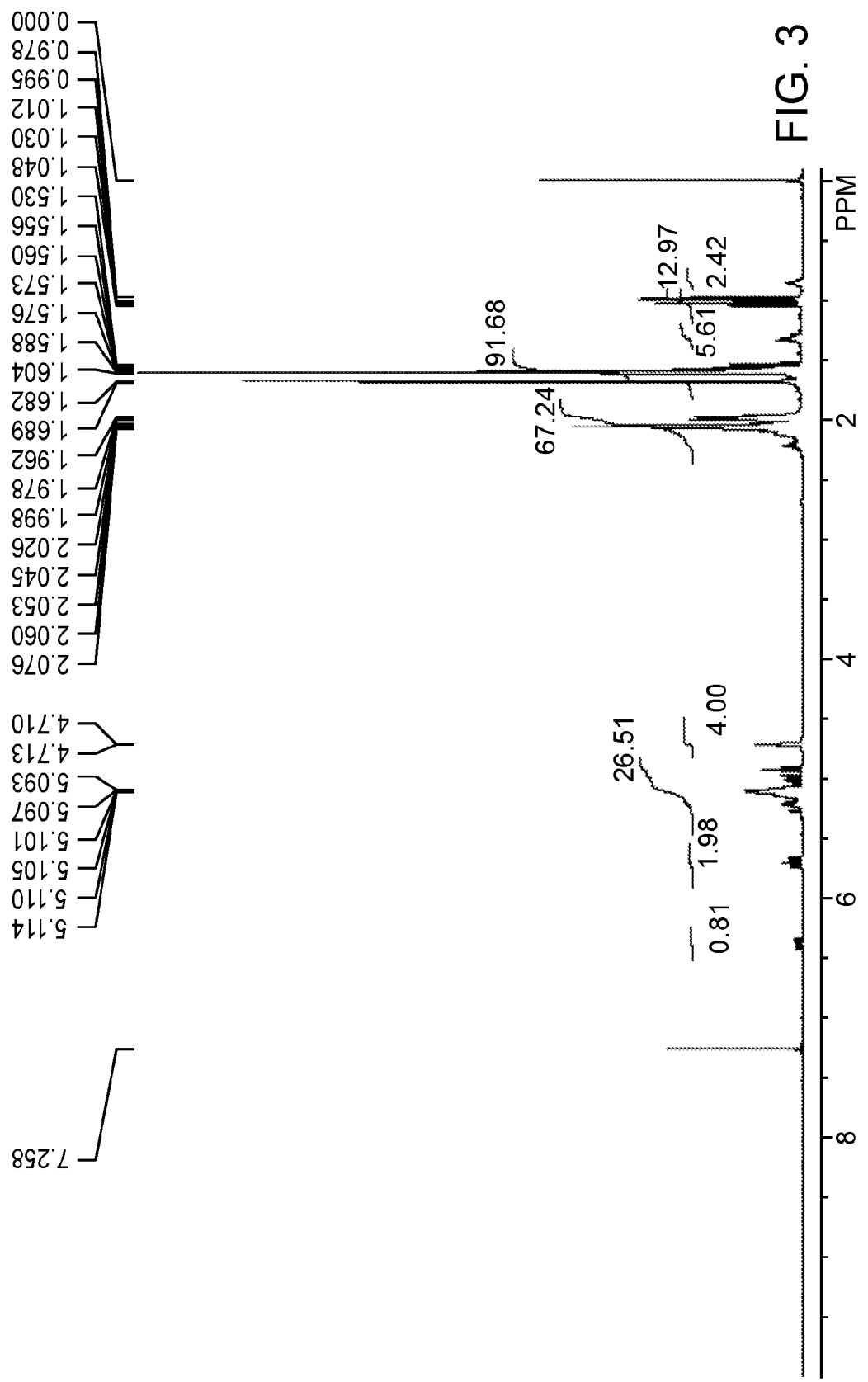
FIG. 3 provides a $^1$H NMR spectrum of β-farnesene that is 25% hydrogenated.

Referring now to FIG. 3 and Examples 8 and 9, microbial-derived farnesene is partially hydrogenated to produce a feedstock comprising a mixture of $C_{15}$ trienes. As shown in Example 8, delivering a controlled amount of hydrogen (1 mol equivalent hydrogen) under controlled reaction conditions with a suitable catalyst (5 wt % Pd/C at a loading of 3 g/kg) yields an olefinic mixture comprising almost exclusively dihydrofarnesene, with less than 10% of the mono-olefin molecules exhibiting a conjugated diene moiety. As shown in Example 9, delivering a controlled amount of hydrogen (1 molar equivalent of hydrogen) under controlled reaction conditions with a Lindlar catalyst yields an olefinic mixture comprising almost exclusively dihydrofarnesene, with less than 12% of the mixture attributed to tetrahydrofarnesene.

The methods described herein may be used to produce a partially hydrogenated β-farnesene feedstock that comprises about 60, 65, 70, 75, 76, 77, 78, 79, 80, 81, 82, 83, 84, 85, 86, 87, 88, 89 or 90% hexahydrofarnesene. For example, partially hydrogenated farnesene produced by delivering about 2.4-3.4 (or about 2.5-3.2, or about 2.7-3.1) mol equivalents H$_2$/mol farnesene in a controlled manner or multi-stage as described herein may comprise about 50, 55, 60, 65, 70, 75, 76, 77, 78, 79, 80, 81, 82, 83, 84, 85, 86, 87, 88, 89 or 90% hexahydrofarnesene. As described herein and illustrated in Example 34 and FIGS. 7A-7C, the amount of hydrogen delivered can be carefully controlled to achieve a desired balance between mono-olefinic, di-olefinic and alkane species.

In some variations, the olefinic feedstocks derived from partially hydrogenated hydrocarbon terpenes using the methods disclosed herein are suitable for catalytic oligomerization to form a mixture of isoparaffins. In some variations, at least a portion of the mixture of isoparaffins so produced may be used as a base oil.

In some variations, the olefinic feedstocks derived from partially hydrogenated hydrocarbon terpenes using the methods disclosed herein are suitable for catalytic reaction with one or more alphaolefins to form a mixture of isoparaffins comprising adducts of the terpene and the one or more alphaolefins. In some variations, at least a portion of the mixture of isoparaffins so produced may be used as a base oil. Non-limiting examples of base oils that are produced using olefinic feedstocks described herein are described in U.S. provisional patent application 61/475,221 filed 13 Apr. 2011, U.S. provisional patent application 61/482,122 filed 3 May 2011, U.S. provisional patent application 61/502,252 filed 28 Jun. 2011, U.S. provisional patent application 61/524,143 filed 16 Aug. 2011, and PCT International Application No. US2012/024926 entitled "BASE OILS AND METHODS FOR MAKING THE SAME" filed 13 Feb. 2012 concurrently herewith which claims priority from U.S. provisional applications 61/475,217, 61/475,221, 61/482,122, 61/493,316, 61/502,252, and 61/524,143), each of which is incorporated herein by reference in its entirety.

Methods are disclosed herein that comprise using an olefinic feedstock comprising a partially hydrogenated $C_{10}$-$C_{30}$ hydrocarbon terpene as a monomer or reactant in any industrial process, e.g., an industrial oligomerization, polymerization, hydroformylation, or carbonylation process. Products produced by such methods are disclosed, e.g. alcohols, detergents, surfactants, polymers, plastics, rubbers, or oils.

Compositions

If hydrogenation of a conjugated alkene (e.g. a $C_{10}$-$C_{30}$ hydrocarbon terpene such as myrcene, ocimene or farnesene) is carried out with insufficient hydrogen to saturate substantially all carbon-carbon double bonds, a mixture comprising molecules having different degrees of hydrogenation may be produced. For conjugated alkenes containing a conjugated diene and at least one additional olefinic bond, partial hydrogenation (e.g. with about 2 molar equivalents of hydrogen, or about 1 molar equivalent or less of hydrogen) may preferentially reduce or eliminate at least one olefinic bond of the conjugated diene moiety, as described herein.

Partial hydrogenation of a conjugated alkene may result in a distribution of species. For example, myrcene can be partially hydrogenated to result in distribution of hexahydromyrcene, tetrahydromyrcene, dihydromyrcene, and myrcene. Farnesene can be partially hydrogenated to result in a distribution of farnesane, hexahydrofarnesene, tetrahydrofarnesene, dihydrofarnesene, and farnesene.

However, the distribution of species produced by partial hydrogenation can be tuned through selecting the type, activity and loading of the catalyst, and the catalysis conditions (e.g. temperature and/or controlled hydrogen delivery).

As described herein, in some variations, the hydrogenation may be accomplished in two or more stages to produce a desired distribution of species in a partially hydrogenated terpene hydrocarbon. For example, the amount of hydrogen, catalysis conditions (structure and type of catalyst, catalyst loading, reaction time, temperature and/or hydrogen pressure) of a first stage may be selected to produce an intermediate distribution of species, and the amount of hydrogen and catalysis conditions (structure and type of catalyst, temperature and/or hydrogen pressure) for a second hydrogenation stage may be selected based on the intermediate distribution of species formed in the first stage to produce a desired final distribution of species. In certain variations, the catalysis conditions of a second stage may be selected so as to minimize formation of alkane.

For example, the catalysis conditions (catalyst type, catalyst structure, catalyst loading, temperature, hydrogen pressure and/or reaction time used in one or more hydrogenation stages as described herein) may be selected so that partial hydrogenation of a hydrocarbon terpene (e.g. myrcene, ocimene, or farnesene) results in a distribution that is unexpectedly rich in mono-olefinic species. Myrcene can be hydrogenated to produce partially hydrogenated myrcene in which tetrahydromyrcene is the predominant species (e.g. at least about 50%, 55%, 60%, 70% or 80% of the sample is tetrahydromyrcene). Farnesene can be hydrogenated to produce partially hydrogenated farnesene in which hexahydrofarnesene is the predominant species (e.g. at least about 50%, 55%, 60%, 70% or 80% of the sample is hexahydrofarnesene).

In certain variations, the hydrogenation is conducted in a single stage, and the catalyst and/or catalysis conditions are selected to provide a desired distribution of species. In one non-limiting example, a catalyst and catalyst conditions that are known to selectively reduce at least one olefinic bond in a conjugated diene moiety may be used to produce a composition rich in tri-olefinic species. In another non-limiting example, a catalyst and catalysis conditions that are known to selectively produce mono-olefins may be used to produce a composition rich in mono-olefinic species.

Provided herein are examples of specific compositions for olefinic feedstocks derived by partial hydrogenation of conjugated hydrocarbon terpenes. For example, the following classes of olefinic feedstock compositions are disclosed herein: i) olefinic feedstocks compositions that have very low amounts of conjugated dienes (e.g., less than about 10% conjugated diene, less than about 5% conjugated diene, or less than about 1% conjugated diene); ii) olefinic feedstocks comprised predominantly of mono-olefins and di-olefins (e.g., at least about 80%, or at least about 90%, or at least about 95% mono-olefins and di-olefins); iii) olefinic feedstock compositions comprised predominantly of mono-olefinic species (e.g., at least about 60%, at least about 65%, at least about 70%, at least about 75%, or at least about 80% mono-olefins); v) olefinic feedstock compositions that have limited amounts of alkanes (e.g., less than about 25%, less than about 20%, less than about 15%, less than about 10%, or less than about 5%); vi) olefinic feedstock compositions that have limited amounts of conjugated dienes and limited amounts of alkanes; vii) olefinic feedstock compositions consisting essentially of tri-olefins and having limited amounts of conjugated dienes and alkanes; viii) olefinic feedstock compositions comprised predominantly of mono-olefins and having limited amounts of conjugated dienes and alkanes; and ix) olefinic feedstock compositions comprising substantial amounts of mono-olefins (e.g., at least about 50%, at least about 55%, at least about 60%, at least 65%, at least about 70%, at least about 75%, or at least about 80% mono-olefin) and limited amounts of di-olefins (e.g., at most about 10%, at most about 8%, at most about 5%, at most about 3%, at most about 2%, at most about 1% di-olefin, or at most about 0.5% di-olefin). In some variations, di-olefins that are present may be substantially unconjugated, e.g., so that a composition comprises at most about 2%, at most about 1%, at most about 0.5%, at most about 0.1%, or no detectable conjugated species.

Partially hydrogenated α-farnesene or β-farnesene may comprise any amount of and any combination of dihydrofarnesene, tetrahydrofarnesene, hexahydrofarnesene, farnesane, and farnesene. Nonlimiting, exemplary structures for various species of dihydrofarnesene, tetrahydrofarnesene and hexahydrofarnesene are shown below.

Dihydrofarnesene:

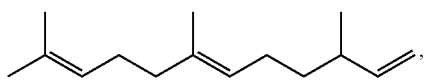

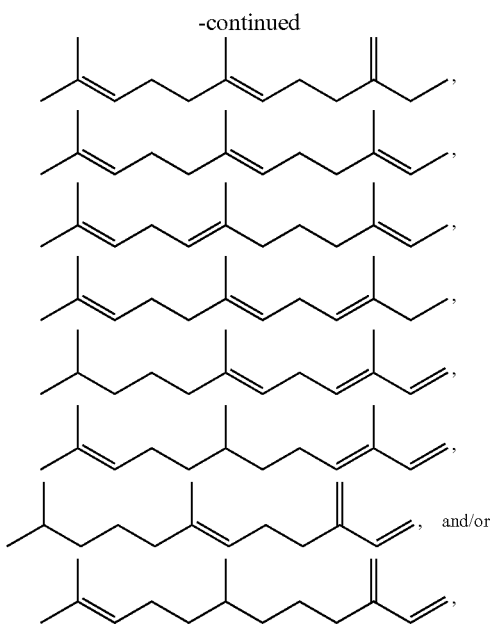

including isomers of the foregoing.
Tetrahydrofarnesene:

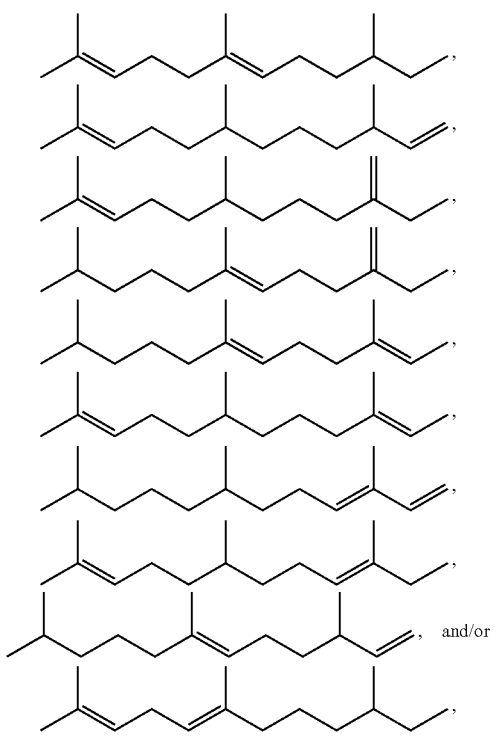

including any isomers of the foregoing.
Hexahydrofarnesene:

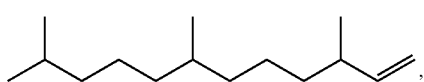

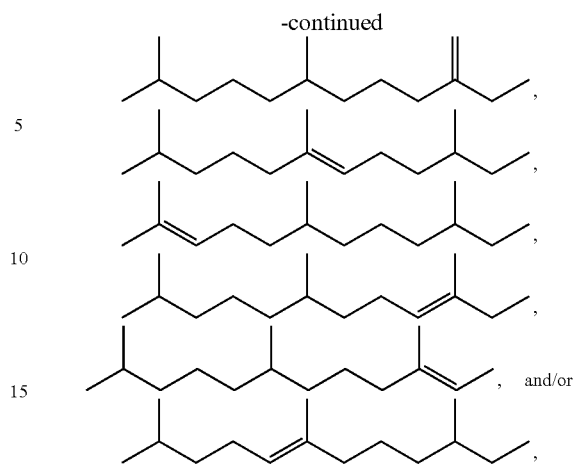

including any isomers of the foregoing.

Partially hydrogenated myrcene may comprise any amount of, and any combination of, dihydromyrcene, tetrahydromyrcene, 2,6-dimethyloctane, and myrcene. Nonlimiting exemplary structures for various species of dihydromyrcene and tetrahydromyrcene are shown below.

Dihydromyrcene:

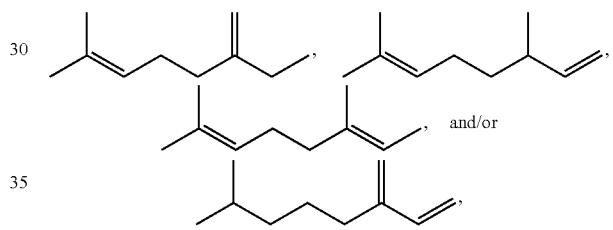

including any isomers of the foregoing.
Tetrahydromyrcene:

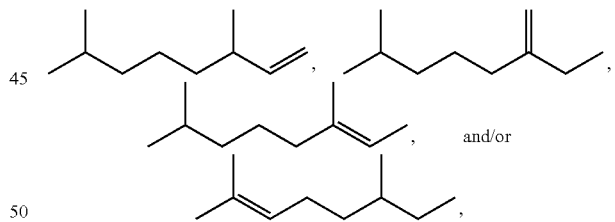

including any isomers of the foregoing.

Partially hydrogenated ocimene may comprise any amount of and any combination of dihydroocimene, tetrahydroocimene, 2,6-dimethyloctane, and ocimene. Nonlimiting exemplary structures for various species of dihydroocimene and tetrahydroocimene are shown below.

Dihydroocimene:

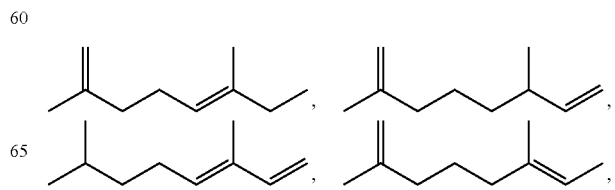

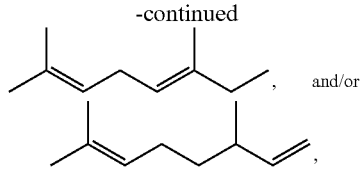, and/or including any isomers of the foregoing.
Tetrahydroocimene:

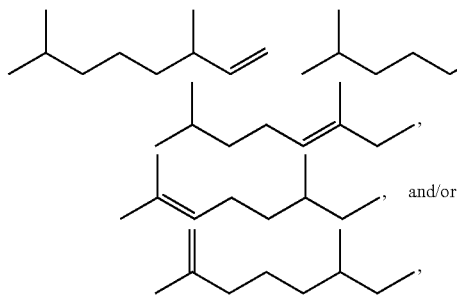, and/or including any isomers of the foregoing.

The degree of hydrogenation in a partially hydrogenated hydrocarbon terpene (e.g., farnesene) sample can be quantified by a variety of methods, e.g. by mol of $H_2$ consumed per mol hydrocarbon terpene (e.g. per mol farnesene) in the hydrogenation process, by an analysis of the degree of unsaturation in the sample (e.g. by Bromine number, which may be measured according to ASTM D1159-07 "Standard Test Method for Bromine Numbers of Petroleum Distillates and Commercial Aliphatic Olefins by Electrometric Titration" which is incorporated herein by reference in its entirety, or by Bromine index, which may be measured according to ASTM D2710-09 "Standard Test Method for Bromine Index of Petroleum Hydrocarbons by Electrometric Titration" which is incorporated herein by reference in its entirety), or by measuring the relative populations of each species (e.g., farnesene, farnesane, hexahydrofarnesene, tetrahydrofarnesene, and dihydrofarnesene), e.g. by GC-MS or GC-FID. In some variations, species in a partially hydrogenated sample may be determined by GC-MS or GC-FID as follows. Peak areas associated with ions corresponding to each of farnesane, hexahydrofarnesene, tetrahydrofarnesene, and dihydrofarnesene can be calculated, and the resulting relative populations of each species can be determined. Alternatively, if the degree of unsaturation (e.g., as measured by Br number) and the area % farnesane for a sample are known, and assuming only mono-olefinic and di-olefinic species are present in significant amounts (e.g. greater than about 1 area % in a GC-MS measurement), the relative amounts of mono-olefinic and di-olefinic species can be calculated. Table 1 shows a theoretical correlation between % unsaturation and Bromine number, assuming that partially hydrogenated farnesene responds to bromine as a tri-unsaturate. An experimentally measured Bromine number may be used to estimate a % hydrogenation in a sample using Table 1. An experimentally measured % hydrogenation (e.g., by GC-FID or GC-MS) can be used to estimate a Br number in a number using Table 1.

Table 1 provides an expected Bromine number for various partially hydrogenated farnesene feedstocks.

TABLE 1

| Mol $H_2$/mol farnesene | % hydrogen saturation | Corresponding Br number |
|---|---|---|
| 0.25 | 6.3 | 293 |
| 0.5 | 12.5 | 272 |
| 0.75 | 18.8 | 252 |
| 1 | 25 | 232 |
| 1.25 | 31.3 | 212 |
| 1.5 | 37.5 | 193 |
| 1.75 | 43.8 | 173 |
| 2 | 50 | 153 |
| 2.25 | 56.3 | 134 |
| 2.5 | 63.5 | 115 |
| 2.75 | 68.8 | 95 |
| 3 | 75 | 76 |
| 3.25 | 81.3 | 57 |
| 3.5 | 87.5 | 38 |
| 3.75 | 93.8 | 19 |
| 4 | 100 | 0 |

In some variations, partially hydrogenated farnesene (e.g. β-farnesene) used as a feedstock comprises hexahydrofarnesene, and may additionally comprise tetrahydrofarnesene and/or farnesane. In some variations, the feedstock may comprise hexahydrofarnesene, tetrahydrofarnesene and farnesane. In some variations, the feedstock may comprise hexahydrofarnesene, tetrahydrofarnesene and dihydrofarnesene. Some feedstocks may comprise hexahydrofarnesene, tetrahydrofarnesene, dihydrofarnesene and farnesane. Some feedstocks may comprise hexahydrofarnesene, tetrahydrofenesene, dihydrofarnesene, farnesane, and farnesene (or an isomer thereof).

In some variations, partially hydrogenated myrcene used as a feedstock comprises tetrahydromyrcene, and, in certain variations, may additionally comprise dihydromyrcene and/or hexahydromyrcene. Partially hydrogenated ocimene used as a feedstock comprises tetrahydroocimene and may, in certain variations, additionally comprise dihydroocimene and/or hexahydroocimene.

Described herein are feedstocks in which the partial hydrogenation proceeds so as to selectively reduce at least one olefinic bond in a conjugated diene moiety in a hydrocarbon terpene (e.g. a $C_{10}$-$C_{30}$ hydrocarbon terpene such as myrcene, ocimene, or farnesene (e.g. β-farnesene)). For example, some feedstocks comprise partially hydrogenated β-farnesene in which the partial hydrogenation proceeds so as to selectively reduce the conjugated diene, so that a sample that is 25% hydrogenated consists essentially of dihydrofarnesene (e.g. one or more dihydrofarnesene structures shown in Examples 8 and 9 herein).

Described herein are feedstocks in which the partial hydrogenation proceeds so as to selectively produce a mono-olefin (e.g. hexahydrofarnesene in the case of farnesene (e.g. β-farnesene) and tetrahydromyrcene in the case of myrcene) in greater quantities than would be statistically expected. The mono-olefin-rich feedstock produced from partial hydrogenation of hydrocarbon terpenes (e.g. hydrocarbon terpenes microbially produced via genetically engineered cells using a renewable carbon source as described herein) can be used in place of, or in addition to, an olefinic feedstock derived from fossil fuel sources (e.g. a linear or branched mono-olefin or a linear or branched alpha-olefin derived from petroleum products).

In one embodiment, described herein are olefinic feedstocks comprising partially hydrogenated acyclic or cyclic $C_{10}$-$C_{30}$ hydrocarbon terpene (e.g. myrcene, ocimene, or farnesene), wherein the partially hydrogenated hydrocarbon terpene comprises at least about 60% mono-olefin and less than about 25% alkane. In some variations, the hydrocarbon terpene is produced by bioengineered microorganisms using a renewable carbon source. In some variations, the olefinic feedstock comprises at least about 65% mono-olefin and less than about 25% alkane. In some variations, the olefinic feedstock comprises at least about 70% mono-olefin and less than about 20% alkane. In some variations, the olefinic feedstock of comprises at least about 75% mono-olefin and about 10% or less alkane. For example, some olefinic feedstocks comprise at least about 60% hexahydrofarnesene and less than about 25% farnesane, at least about 65% hexahydrofarnesene and less than about 25% farnesane, at least about 70% hexahydrofarnesene and less than about 20% farnesane, at least about 75% hexahydrofarnesene and about 10% or less farnesane. In certain variations, β-farnesene used to make the feedstocks is made by bioengineered microorganisms using a renewable carbon source.

Described herein are feedstock compositions derived from β-farnesene that are about 60-80% (e.g. about 60%, 61%, 62%, 63%, 64%, 65%, 66%, 67%. 68%. 69%, 70%, 71%, 72%, 73%, 74%, 75%, 76%, 77%, 78%, 79%, or 80%) hydrogenated and hexahydrofarnesene is produced in an amount greater than about 50%, e.g. hexahydrofarnesene is present at about 50-80% of the total partially hydrogenated farnesene sample, e.g. about 50, 55, 60, 65, 70, 75, or 80% (as measured by area %). The hexahydrofarnesene-rich feedstock can be used in place of, or in addition to an olefinic feedstock having a similar molecular weight (e.g. a linear or branched mono-olefin, or a linear or branched alpha-olefin). For example, the hexahydrofarnesene-rich feedstock may be used in place of or in addition to a $C_{12}$-$C_{15}$ linear or branched mono-olefin derived from fossil fuels. In some reactions, the hexahydrofarnesene-rich feedstock may be used to substitute for or to supplement a $C_{12}$-$C_{15}$ linear or branched alpha-olefin feedstock.

Described herein are feedstock compositions derived from β-farnesene that are about 70-80% (e.g. about 70%, 71%, 72%, 73%, 74%, 75%, 76%, 77%, 78%, 79%, or 80%) hydrogenated and hexahydrofarnesene is produced in an amount greater than about 50%, e.g. hexahydrofarnesene is present at about 50-80% of the total partially hydrogenated farnesene sample, e.g. about 50, 55, 60, 65, 70, 75 or 80%. The hexahydrofarnesene-rich feedstock may be used in place of, or in addition to an olefinic feedstock having a similar molecular weight (e.g. a linear or branched mono-olefin, or a linear or branched alpha-olefin). For example, the hexahydrofarnesene-rich feedstock may be used in place of or in addition to a $C_{12}$-$C_{15}$ linear or branched mono-olefin derived from fossil fuels. In some reactions, the hexahydrofarnesene-rich feedstock may be used to substitute for or to supplement a $C_{12}$-$C_{15}$ linear or branched alpha-olefin feedstock.

Described herein are feedstock compositions derived from myrcene that are about 60-70% (e.g. about 60%, 61%, 62%, 63%, 64%, 65%, 66%, 67%, 68%, 69% or 70%) hydrogenated and tetrahydromyrcene is produced in an amount greater than about 50% (e.g. about 50, 55, 60, 65, 70, 75, 80, 85, 90 or 95%). The tetrahydromyrcene-rich feedstock may be used in place of, or in addition to, an olefinic feedstock.

In some variations, a feedstock comprises partially hydrogenated β-farnesene in which least about 2 but less than about 3.8 mol $H_2$ was consumed per mol β-farnesene during hydrogenation. In some variations, a feedstock comprises partially hydrogenated β-farnesene in which about 2, 2.25, 2.5, 2.75, 3, 3.25 or 3.5 mol $H_2$ was consumed per mol β-farnesene during hydrogenation. In some variations, a feedstock comprises partially hydrogenated β-farnesene in which about 2.5, 2.6, 2.7, 2.8, 2.9, 3.0, 3.1, 3.2, 3.3, 3.4 or 3.5 mol $H_2$ was consumed per mol β-farnesene during hydrogenation. In some variations, a feedstock comprises partially hydrogenated β-farnesene in which the degree of hydrogenation is about 60-85%, e.g. about 60, 61, 62, 63, 64, 65, 66, 67, 68, 69, 70, 71, 72, 73, 74, 75, 76, 77, 78, 79, 80, 81, 82, 83, 84 or 85%, corresponding to about 2.5 to about 3.5 mol $H_2$ (e.g. 2.5, 2.6, 2.7, 2.8, 2.9, 3.0, 3.1, 3.2, 3.3, 3.4 or 3.5 mol $H_2$) per mol β-farnesene consumed during hydrogenation.

In some variations, a partially hydrogenated β-farnesene feedstock comprises at least about 50% hexahydrofarnesene, e.g. about 50, 55, 60, 65, 70, 75, or 80% hexahydrofarnesene. In some variations, a partially hydrogenated farnesene feedstock comprises at least about 50% hexahydrofarnesene (e.g. about 50, 55, 60, 65, 70, 75 or 80%) and less than about 10% (e.g. less than about 10%, less than about 5%, less than about 4%, less than about 3%, less than about 2%, or less than about 1%) dihydrofarnesene. In some variations, a partially hydrogenated farnesene feedstock comprises at least about 50% hexahydrofarnesene (e.g. about 50, 55, 60, 65, 70, 75 or 80%) and about 5% or less (e.g. less than about 5%, less than about 4%, less than about 3%, less than about 2%, or less than about 1%) farnesene (or isomers thereof). For example, in some variations, a partially hydrogenated farnesene feedstock comprises at least about 50% hexahydrofarnesene (e.g. about 50, 55, 60, 65, 70, 75 or 80%) and less than about 1% dihydrofarnesene and less than about 1% farnesene (or isomers thereof).

In some variations, a partially hydrogenated farnesene feedstock comprises at least about 50% hexahydrofarnesene (e.g. about 50, 55, 60, 65, 70, 75 or 80%) and about 25% or less farnesane, e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, or 5% or less farnesane. For example, some partially hydrogenated farnesene feedstocks comprise about 60-80% hexahydrofarnesene, and about 5-25% farnesane.

In some variations, a partially hydrogenated farnesene feedstock comprises at least about 50% hexahydrofarnesene (e.g. about 50, 55, 60, 65, 70, 75 or 80%) and about 25% or less tetrahydrofarnesene, e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, or 10% or less tetrahydrofarnesene.

In some variations, a partially hydrogenated farnesene feedstock comprises at least about 50%, or at least about 60% hexahydrofarnesene (e.g. about 50, 55, 60, 65, 70, 75 or 80%), about 25% or less farnesane, (e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, or 5% or less farnesane), and about 25% or less tetrahydrofarnesene, (e.g. about 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, or 10%). For example, some feedstocks comprise about 50-80% hexahydrofarnesene, about 0-25% tetrahydrofarnesene, and about 5-25% farnesane. Some feedstocks comprise about 60-80% hexahydrofarnesene, about 0-15% tetrahydrofarnesene, and about 5-25% farnesane. Some feedstocks comprise about 65-80% hexahydrofarnesene, about 0-5% tetrahydrofarnesene, and about 0-20% farnesane.

Some specific non-limiting examples of compositions of partially hydrogenated farnesene feedstocks are provided in Table 2A. Each "X" specifically discloses a feedstock comprising hexahydrofarnesene in the area % indicated on the horizontal axis and farnesane in the area % indicated on the vertical axis. Each of the ranges in Table 2A specifically discloses the numerical values provided as lower limits RL and upper limits RU, and also specifically discloses values within the range limits, e.g., each of the following numbers within each range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. For any of the compositions in Table 2A, the amount of aromatic compounds may be less than about 1 ppm. For any of the compositions in Table 2A, the amount of sulfur and the amount of aromatic compounds may each be less than 1 ppm. For any of the compositions in Table 2A, the terpene is microbially derived from renewable carbon sources, and has a renewable carbon content of about 100%.

4, 3, 2, or %, or no detectable amount of tetrahydrofarnesene, individually. Provided herein are each of the compositions specifically disclosed in Table 2A individually, and about 6% or less tetrahydrofarnesene, e.g. about 5, 4, 3, 2, or %, or no detectable amount of tetrahydrofarnesene, individually. For example, some feedstocks comprise about at least about 70-80% hexahydrofarnesene, about 5-10% farnesane, and about 10-20% tetrahydrofarnesene. Some feedstocks comprise at least about 70-80% hexahydrofarnesene, about 5-15% farnesane, and about 5% or less tetrahydrofarnesene.

In some variations, described herein are olefinic feedstocks comprising partially hydrogenated acyclic or cyclic $C_{10}$-$C_{30}$ conjugated hydrocarbon terpene (e.g., myrcene, ocimene, or farnesene), wherein the partially hydrogenated hydrocarbon terpene comprises less than about 10% of the corresponding alkane and less than about 10% of the starting hydrocarbon terpene. In some variations, the partially hydrogenated hydrocarbon terpene comprises about 5% or less (e.g., about 5%, 4%, 3%, 2% or 1%) of the corresponding alkane and about 5% or less of the starting hydrocarbon terpene. For example, in one variation, an olefinic feedstock comprises about 5% or less (e.g., about 5%, 4%, 3%, 2%, 1% or less) farnesane and about 5% or less (e.g., about 5%, 4%, 3%, 2%, 1%, or even less, an amount not detected by GC/MS) farnesane, with the remainder being comprised of tetrahydrofarnesene and hexahydrofarnesene in any relative amounts. For example, in some variations, partially hydrogenated farnesene comprises less than about 10% farnesene and less than about 10% farnesane, such that the combined total of hexahydrofarnesene and tetrahydrofarnesene comprises at least about 80% of the partially hydrogenated farnesene (e.g., about 80%, about 85%, about 90%, about 95%, 96%, 97%, 98% or 99% of the partially hydrogenated farnesene), wherein any relative amounts of hexahydrofarnesene and tetrahydrofarnesene may be present.

Some specific non-limiting examples of partially hydrogenated farnesene compositions wherein the combined total of hexahydrofarnesene and tetrahydrofarnesene comprises about 80% of the total composition are provided in Table 2B below, where each "X" specifically discloses a feedstock

TABLE 2A

| | | area % of hexahydrofarnesene | | | | | | | | | |
|---|---|---|---|---|---|---|---|---|---|---|---|
| | | 50-55 | 55-60 | 60-65 | 65-70 | 70-75 | 75-80 | 80-85 | 85-90 | 90-95 | >95 |
| area % of farnesane | <4 | X | X | X | X | X | X | X | X | X | X |
| | 4-6 | X | X | X | X | X | X | X | X | X | X |
| | 6-8 | X | X | X | X | X | X | X | X | X | |
| | 8-10 | X | X | X | X | X | X | X | X | X | |
| | 10-12 | X | X | X | X | X | X | X | X | X | |
| | 12-14 | X | X | X | X | X | X | X | | | |
| | 14-16 | X | X | X | X | X | X | X | | | |
| | 16-18 | X | X | X | X | X | X | X | | | |
| | 18-20 | X | X | X | X | X | X | X | | | |
| | 20-22 | X | X | X | X | X | X | | | | |
| | 22-24 | X | X | X | X | X | X | | | | |

Also provided herein are each of the compositions specifically disclosed in Table 2A individually, and about 25% or less tetrahydrofarnesene, e.g. about 25, 24, 23, 22, 21, 20, 19, 18, 17, 16, 15, 14, 13, 12, 11, 10, 9, 8, 7, 6, 5, 4, 3, 2, or %, or no detectable amount of tetrahydrofarnesene, individually. Provided herein are each of the compositions specifically disclosed in Table 2A individually, and about 10% or less tetrahydrofarnesene, e.g. about 10, 9, 8, 7, 6, 5, comprising hexahydrofarnesene in the area % indicated on the horizontal axis and tetrahydrofarnesene in the area % indicated on the vertical axis. For any of the compositions in Table 2B, the amount of sulfur may be less than about 1 ppm. For any of the compositions in Table 2B, the amount of aromatic compounds may be less than about 1 ppm. For any of the compositions in Table 2B, the amount of sulfur and the amount of aromatic compounds may each be less than 1 ppm. For any of the compositions in Table 2B, the terpene is microbially derived from renewable carbon sources, and has a renewable carbon content of about 100%.

tial amounts of hexahydrofarnesene and limited amounts of tetrahydrofarnesene are provided in Table 2C below, where each "X" specifically discloses a feedstock comprising hexa-

TABLE 2B

| | | Area % of hexahydrofarnesene | | | | | | | | | |
|---|---|---|---|---|---|---|---|---|---|---|---|
| | | <10 | 10-20 | 20-30 | 30-40 | 40-50 | 50-60 | 60-70 | 70-80 | 80-90 | >90 |
| area % of tetrahydrofarnesene | <0.5 | | | | | | | | X | X | X |
| | <1 | | | | | | | | X | X | X |
| | 2-3 | | | | | | | | X | X | X |
| | 4-5 | | | | | | | | X | X | X |
| | 5-10 | | | | | | | | X | X | X |
| | 10-20 | | | | | | | X | X | X | X |
| | 20-30 | | | | | | X | X | X | X | |
| | 30-40 | | | | X | X | X | X | X | | |
| | 40-50 | | | X | X | X | X | X | | | |
| | 50-60 | | X | X | X | X | X | | | | |
| | 60-70 | | X | X | X | X | | | | | |
| | 70-80 | X | X | X | X | | | | | | |
| | 80-90 | X | X | X | | | | | | | |
| | >90 | X | | | | | | | | | |

For each of the compositions disclosed in Table 2B, the amount of farnesene may be, individually, about 10%, 9%, 8%, 7%, 6%, 5%, 4%, 3%, 2%, 1%, 0.5%, 0.3%, or less than 0.3%, e.g., an amount not detectable by GC/MS. For each of the compositions disclosed in Table 2B, the amount of farnesane may be, individually, about 10%, 9%, 8%, 7%, 6%, 5%, 4%, 3%, 2%, 1%, 0.5%, 0.3%, or less than 0.3%, e.g., an amount not detectable by GC/MS. For example, in one variation, a partially hydrogenated farnesene feedstock that is about 60-65% hydrogenated comprises about 40-50% hexahydrofarnesene, about 40-50% tetrahydrofarnesene, less than about 10% dihydrofarnesene, less than about 1% (e.g., less than about 0.5% or no detectable amount by GC/MS) farnesane, and less than about 1% (e.g., less than about 0.5% or no detectable amount by GC/MS) farnesene.

In some variations, a partially hydrogenated farnesene composition comprises substantial amounts of hexahydrofarnesene and limited amounts of tetrahydrofarnesene. It some situations, diolefinic species may contribute to undesired branching, cross-reactions, and the like. In some variations, limited amounts of tetrahydrofarnesene present are substantially unconjugated, e.g., so that the composition comprises about 2% or less or about 1% or less conjugated diene. Some specific non-limiting examples of partially hydrogenated farnesene compositions comprising substantial amounts of hexahydrofarnesene and limited amounts of tetrahydrofarnesene are provided in Table 2C below, where each "X" specifically discloses a feedstock comprising hexahydrofarnesene in the area % indicated on the horizontal axis and tetrahydrofarnesene in the area % indicated on the vertical axis. For any of the compositions in Table 2C, the amount of sulfur may be less than about 1 ppm. For any of the compositions in Table 2C, the amount of aromatic compounds may be less than about 1 ppm. For any of the compositions in Table 2C, the amount of sulfur and the amount of aromatic compounds may each be less than 1 ppm. For any of the compositions in Table 2C, the terpene is microbially derived from renewable carbon sources, and has a renewable carbon content of about 100%.

TABLE 2C

| | | Area % of hexahydrofarnesene | | | | | | | | | |
|---|---|---|---|---|---|---|---|---|---|---|---|
| | | 50-55 | 55-60 | 60-65 | 65-70 | 70-75 | 75-80 | 80-85 | 85-90 | 90-95 | >95 |
| area % of tetrahydrofarnesene | <0.3 | X | X | X | X | X | X | X | X | X | X |
| | <0.5 | X | X | X | X | X | X | X | X | X | X |
| | <1 | X | X | X | X | X | X | X | X | X | X |
| | 1-2 | X | X | X | X | X | X | X | X | X | X |
| | 2-3 | X | X | X | X | X | X | X | X | X | X |
| | 3-4 | X | X | X | X | X | X | X | X | X | X |
| | 4-5 | X | X | X | X | X | X | X | X | X | X |
| | 5-6 | X | X | X | X | X | X | X | X | X | X |
| | 6-7 | X | X | X | X | X | X | X | X | X | X |
| | 7-8 | X | X | X | X | X | X | X | X | X | X |
| | 8-9 | X | X | X | X | X | X | X | X | X | X |
| | 9-10 | X | X | X | X | X | X | X | X | X | X |
| | 10-11 | X | X | X | X | X | X | X | X | X | X |
| | 11-12 | X | X | X | X | X | X | X | X | X | X |

For each of the compositions disclosed in Table 2C, the amount of farnesene may be, individually, about 10%, 9%, 8%, 7%, 6%, 5%, 4%, 3%, 2%, 1%, 0.5%, 0.3%, or less than 0.3%, e.g., an amount not detectable by GC/MS. For each of the compositions disclosed in Table 2C, the amount of farnesane may be, individually, about 10%, 9%, 8%, 7%, 6%, 5%, 4%, 3%, 2%, 1%, 0.5%, 0.3%, or less than 0.3%, e.g., an amount not detectable by GC/MS.

In some variations, a suitable hydrocarbon terpene feedstock comprises about 70-85% mono-olefin, about 12-17% farnesane, and about 5% or less di-olefin. In some variations, a suitable hydrocarbon terpene feedstock comprises about 70-85% mono-olefin, about 12-17% farnesane, and about 3% or less di-olefin. In some variations, a suitable hydrocarbon terpene feedstock comprises about 70-85% mono-olefin, about 12-17% farnesane, and about 2% or less di-olefin. In some variations, a suitable hydrocarbon terpene feedstock comprises about 70-85% mono-olefin, about 12-17% farnesane, and about 1% or less di-olefin. In some variations, a suitable hydrocarbon terpene feedstock comprises about 75-85% mono-olefin, about 15% or less farnesane, and about 5% or less di-olefin. In some variations, a suitable hydrocarbon terpene feedstock comprises about 75-85% mono-olefin, about 15% or less farnesane, and about 3% or less di-olefin. In some variations, a suitable hydrocarbon terpene feedstock comprises about 75-85% mono-olefin, about 15% or less farnesane, and about 2% or less di-olefin. In some variations, a suitable hydrocarbon terpene feedstock comprises about 75-85% mono-olefin, about 15% or less farnesane, and about 1% or less di-olefin.

It should be understood that analogous compositions to those shown in Table 2A, 2B, and 2C are contemplated in which the hydrocarbon terpene is a hydrocarbon terpene other than farnesene, e.g., myrcene, springene, or geranylfarnesene.

In certain embodiments, one partially hydrogenated acyclic or cyclic conjugated $C_{10}$-$C_{30}$ hydrocarbon terpene as described herein is combined with one or more different partially hydrogenated acyclic or cyclic $C_{10}$-$C_{30}$ hydrocarbon terpenes as described herein to make a mixed olefinic feedstock. For example, a mixed olefinic feedstock may comprise partially hydrogenated myrcene mixed with partially hydrogenated farnesene. Any relative amounts of each of the partially hydrogenated terpenes are contemplated, and any relative degree of hydrogenation of each of the partially hydrogenated terpenes is contemplated. For example, mixed olefinic feedstocks are contemplated in which a ratio of a first partially hydrogenated hydrocarbon terpene to a second partially hydrogenated hydrocarbon terpene is about 0.1:1, 0.2:1, 0.3:1, 0.4:1, 0.5:1, 1:1, 2:1, 3:1, 4:1, 5:1, 6:1, 7:1, 8:1, 9:1 or 10:1.

In certain embodiments, a mixed olefinic feedstock comprises one or more partially hydrogenated acyclic or cyclic $C_{10}$-$C_{30}$ hydrocarbon terpenes and one or more olefins not derived from an acyclic or cyclic $C_{10}$-$C_{30}$ hydrocarbon terpene. For example, the olefin may be selected from the group consisting of a $C_5$-$C_{30}$ linear alphaolefin, a $C_5$-$C_{30}$ branched alphaolefin, a $C_5$-$C_{30}$ linear internal olefin, and a $C_5$-$C_{30}$ branched internal olefin. For example, mixed olefinic feedstocks are contemplated in which a ratio of a partially hydrogenated hydrocarbon terpene to another olefin (e.g., an alphaolefin) is about 0.1:1, 0.2:1, 0.3:1, 0.4:1, 0.5:1, 1:1, 2:1, 3:1, 4:1, 5:1, 6:1, 7:1, 8:1, 9:1 or 10:1.

In some variations, an additive is added to a hydrogenation catalyst to increase selectivity. For example, zirconium sulfate may be added to certain catalysts (e.g., palladium containing catalysts such as Pd/C) to increase selectivity. In some variations, a catalyst poison or additive is deliberately introduced to limit reactivity of a catalyst system and to increase selectivity. Any catalyst poison known in the art may be used in an effective amount. Non-limiting examples of additives that may be used to limit reactivity of certain catalysts include triethylamine, carbon monoxide, pyridine, acetone, and ethylene diamine. In some cases, an acidic heterogeneous additive (e.g., $Nb_2O_5$) is used to increase selectivity for mono-olefins by enhancing double bond isomerization, e.g., without skeletal isomerization.

In certain embodiments, the hydrocarbon terpene feedstock may be pre-treated (e.g., to remove oxygenates such as alcohols, acids, epoxides, or glycerides, or low boiling components). Non-limiting examples of pre-treatments to remove oxygenates from hydrocarbon terpene feedstock include distillation, filtration using silica or basic alumina, treatment using molecular sieves (e.g. 13× molecular sieves), or caustic washing (e.g., using 5-30% caustic) followed by centrifuge and separation of aqueous content. In some variations, a combination of two or more of caustic wash, filtration using alumina, and distillation is used to pre-treat hydrocarbon terpene feedstock. It should be noted that such pretreatment may occur prior to and/or following a partial hydrogenation step for the hydrocarbon terpene. In some variations, a hydrocarbon terpene feedstock is treated to remove oxygenates prior to partial hydrogenation (e.g., using silica or basic alumina), and is filtered using diatomaceous earth following partial hydrogenation. In certain variations, a partially hydrogenated feedstock as described herein is stabilized by storing under an inert atmosphere (e.g., dry nitrogen) or by addition of an antioxidant such as 4-tert-butylcatechol (e.g., at 25-200 ppm).

In some variations, a hydrocarbon terpene feedstock has a purity of greater than 97%, a farnesene dimer content of less than 3%, a water content measured by Karl Fischer titration of less than 400 ppm, and total acid number (TAN) of less than 0.1%. In some variations, a hydrocarbon terpene feedstock may include an antioxidant (e.g, TBC (4-tert-butyl catechol) of about 50-125 ppm. It should be noted that in the case of a partially hydrogenated feedstock, the hydrocarbon terpene may be pretreated prior to the selective hydrogenation process using any one of or any combination of the pre-treatments described herein or known in the art. The presence of oxygenates or other contaminants may cause poisoning of catalyst or slow or unpredictable hydrogenation rates, so in some variations it may be desired to pre-treat a hydrocarbon terpene prior to the selective hydrogenation process. In some variations, the hydrocarbon terpene is not pre-treated to remove oxygenates or other contaminants prior to a selective hydrogenation process.

Partially Hydrogenated Conjugated Terpenes

Also provided herein are specific species of partially hydrogenated conjugated hydrocarbon terpenes and methods for making the same. It should be noted that a specific species of partially hydrogenated conjugated terpenes may or may not be produced by a hydrogenation process. In certain variations, a partially hydrogenated hydrocarbon terpene species is prepared by a method that includes one or more steps in addition to or other than catalytic hydrogenation.

Nonlimiting examples of specific species partially hydrogenated conjugated hydrocarbon terpenes include any of the structures provided herein for dihydrofarnesene, tetrahydrofarnesene, and hexahydrofarnesene; any of the structures provided herein for dihydromyrcene and tetrahydromyrcene; and any of the structures provided herein for dihydroocimene and tetrahydroocimene.

One example of a particular species of partially hydrogenated conjugated hydrocarbon terpene that may have utility as a feedstock is a terminal olefin having a saturated hydrocarbon tail with structure (A11):

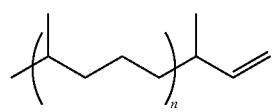

(A11)

where n=1, 2, 3, or 4.

In some variations, a mono-olefinic alphaolefin having structure A11 may be derived from a conjugated hydrocarbon terpene wherein the conjugated diene is at the 1,3-position of the terpene. Provided herein are alphaolefins derived from a 1,3-diene conjugated hydrocarbon terpene (e.g., a $C_{10}$-$C_{30}$ conjugated hydrocarbon terpene such as farnesene, myrcene, ocimene, springene, geranylfarnesene, neophytadiene, trans-phyta-1,3-diene, or cis-phyta-1,3-diene). In one nonlimiting example of an alphaolefin having the general structure A11, 3,7,11-trimethyldodec-1-ene having structure A12 and methods for making the same are provided herein.

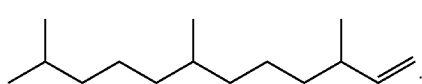

(A12)

A mono-olefinic alphaolefin having structure A11 may be prepared from the appropriate conjugated hydrocarbon terpene using any suitable method. In some variations, the mono-olefinic alphaolefin having structure A11 is produced from primary alcohol of corresponding to the hydrocarbon terpene (e.g., farnesol in the case of farnesene, or geraniol in the case of myrcene). The methods comprise hydrogenating the primary alcohol, forming a carboxylic acid ester or carbamate ester from the hydrogenated alcohol, and pyrolizing the ester (or heating the ester to drive the elimination reaction) to form the alphaolefin with a saturated hydrocarbon tail, e.g., as described in Smith, L. E.; Rouault, G. F. J. Am. Chem. Soc. 1943, 65, 745-750 for the preparation of 3,7-dimethyloct-1-ene, which is incorporated by reference herein in its entirety. The primary alcohol of the corresponding hydrocarbon terpene may be obtained using any suitable method. Examples 14 and 15 herein describe nonlimiting examples of methods for making an alphaolefin having structure A12, 3,7,11-trimethyldodec-1-ene, from farnesol.

It should be noted that other schemes for making alphaolefins having the general structure A11 from conjugated hydrocarbon terpenes are contemplated. For example, in some variations, the hydrocarbon terpene has a conjugated diene at the 1,3-position, and the conjugated diene can be functionalized with any suitable protecting group known to one of skill in the art in a first step (which may comprise one reaction or more than one reaction). The remaining olefinic bonds can be saturated in a second step (which may comprise one reaction or more than one reaction), and the protecting group can be eliminated to produce an alphaolefin having the general structure A11 in a third step (which may comprise one reaction or more than one reaction).

Any suitable protecting group and elimination scheme may be used. For example, a hydrocarbon terpene having a 1,3-conjugated diene (e.g., β-farnesene) may be reacted with an amine (e.g., a dialkyl amine such as dimethylamine or diethylamine) in the first step to produce an amine having the formula $N(R_1)(R_2)(R_3)$, where $R_1$ and $R_2$ are alkyl groups such as methyl or ethyl, and $R_3$ is an unsaturated hydrocarbon originating from the conjugated terpene. (In the case of β-farnesene,

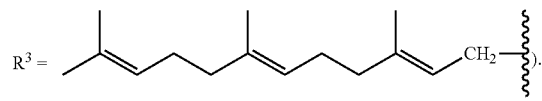 [SMILES: *C/C=C(\C)CC/C=C(\C)CCC=C(C)C]

The resulting amine may be oxidized to the N oxide using hydrogen peroxide followed by elimination to the aldehyde using acetic anhydride. Hydrogenation of the aldehyde in the presence of a catalyst may be carried out to saturate any remaining olefinic bonds on the aliphatic tail originating from the hydrocarbon terpene, and the aldehyde functionality may be eliminated to produce an alphaolefin having structure A11. Scheme I below illustrates an example of such a preparation of an alphaolefin having structure A11 using β-farnesene as a model compound.

SCHEME I

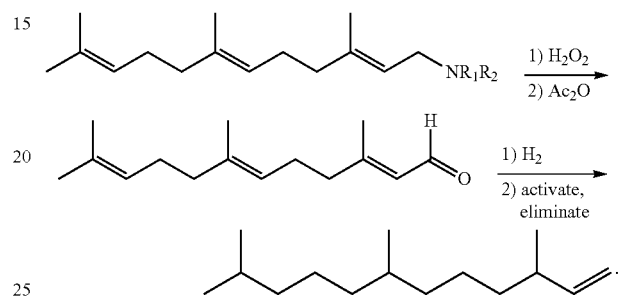

Another variation of a method to make an alphaolefin from a hydrocarbon terpene having a 1,3-conjugated diene follows Scheme II below. Here, the hydrocarbon terpene is reacted with a dialkyl amine (e.g., dimethylamine). The resulting amine has the general formula $N(R_1)_2(R_2)$, where $R_1$ and $R_2$ are alkyl groups such as methyl and $R_3$ is an unsaturated hydrocarbon originating from the hydrocarbon terpene (e.g., in the case of β-farnesene,

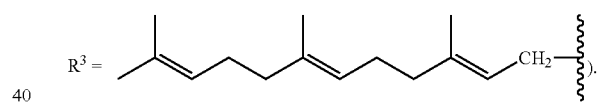

The amine $N(R_1)(R_2)(R_3)$ can be hydrogenated (e.g., using an appropriate catalyst), treated with peroxide, and heated to undergo elimination to form an alphaolefin having structure A11 (e.g., compound A12 if β-farnesene is used as the starting hydrocarbon terpene). Scheme II illustrates this method using β-farnesene as a model compound.

SCHEME II

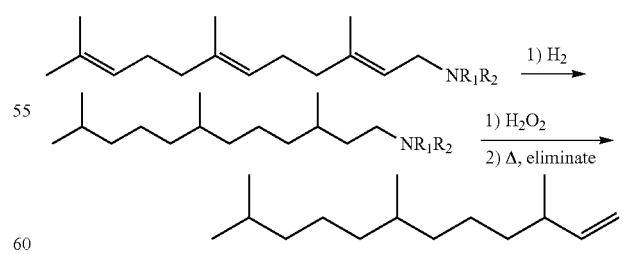

In another variation, a hydrogenated primary alcohol corresponding to a hydrocarbon terpene (e.g., hydrogenated farnesol or hydrogenated geraniol) can be dehydrated using basic aluminum oxide (e.g., at a temperature of about 250° C.) to make an alphaolefin having the general structure A11. Any suitable dehydration apparatus can be used, but in some variations, a hot tube reactor (e.g., at 250° C.) is used to carry out a dehydration of a primary alcohol. In one variation, hydrogenated farnesol can be dehydrated using basic aluminum oxide (e.g., in a hot tube reactor at 250° C.) to make compound A12, or an isomer thereof.

Other examples of particular species of partially hydrogenated conjugated hydrocarbon terpene that may have utility as a feedstock are mono-olefins having a saturated hydrocarbon tail with structure (A13) or structure (A15):

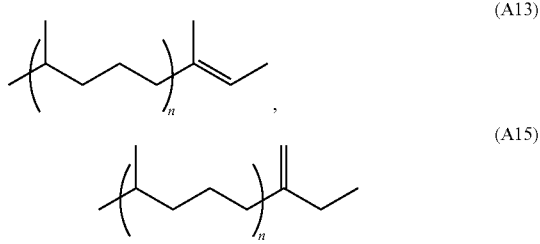

(A13)

(A15)

where n=1, 2, 3, or 4. A mono-olefin having the general structure A13, A15 or A11 may in certain instances be derived from a conjugated hydrocarbon terpene having a 1,3-diene moiety, such as myrcene, farnesene, springene, geranylfarnesene, neophytadiene, trans-phyta-1,3-diene, or cis-phyta-1,3-diene. Here again, the conjugated may be functionalized with a protecting group (e.g., via a Diels-Alder reaction) in a first step, exocyclic olefinic bonds hydrogenated in a second step, and the protecting group eliminated in a third step. In one non-limiting example of a method for making mono-olefins having the structure A13, A15 or A11, a conjugated hydrocarbon terpene having a 1,3-diene is reacted with $SO_2$ in the presence of a catalyst to form a Diels-Alder adduct. The Diels-Alder adduct may be hydrogenated with an appropriate hydrogenation catalyst to saturate exocyclic olefinic bonds. A retro Diels-Alder reaction may be carried out on hydrogenated adduct (e.g., by heating, and in some instances in the presence of an appropriate catalyst) to eliminate the sulfone to form a 1,3-diene. The 1,3-diene can then be selectively hydrogenated using a catalyst known in the art to result in a mono-olefin having structure A11, A13 or A15, or a mixture of two or more of the foregoing. Non-limiting examples of regioselective hydrogenation catalysts for 1,3-dienes are provided in Jong Tae Lee et al, "Regioselective hydrogenation of conjugated dienes catalyzed by hydridopentacyanocobaltate anion using β-cyclodextrin as the phase transfer agent and lanthanide halides as promoters," J. Org. Chem., 1990, 55 (6), pp. 1854-1856; in V. M. Frolov et al., "Highly active supported palladium catalysts for selective hydrogenation of conjugated dienes into olefins," Reaction Kinetics and Catalysis Letters, 1984, Volume 25, Numbers 3-4, pp. 319-322; in Tungler, A., Hegedüs, L., Fodor, K., Farkas, G., Fürcht, Á. and Karancsi, Z. P. (2003) "Reduction of Dienes and Polyenes," in *The Chemistry of Dienes and Polyenes*, Volume 2 (ed. Z. Rappoport), John Wiley & Sons, Ltd, Chichester, UK. doi: 10.1002/0470857226.ch12; and in Tungler, A., Hegedüs, L., Fodor, K., Farkas, G., Fürcht, Á. and Karancsi, Z. P., "Reduction of Dienes and Polyenes" in *Patai's Chemistry of Functional Groups* (John Wiley and Sons, Ltd, published online Dec. 15, 2009, DOI: 10.1002/ 9780470682531.pat0233); each of which is incorporated herein by reference in its entirety. For example, a catalyst known in the art for 1,4 hydrogen addition to 1,3-dienes results in a mono-olefin having structure A13. In one non-limiting example, β-farnesene can be reacted with $SO_2$ in the presence of a catalyst to form a Diels-Alder adduct, which is subsequently hydrogenated, and the sulfone eliminated to form a 1,3-diene, which is subsequently selectively hydrogenated using a catalyst known in the art for regioselective hydrogen additions to 1,3-dienes to form 3,7,11-trimethyldodec-2-ene, 3,7,11-trimethyldodec-1-ene, or 3-methylene-7,11-dimethyldodecane, or a mixture of any two or more of the foregoing.

In yet another example of a particular species of partially hydrogenated hydrocarbon terpene that may have utility as a feedstock, a terminal olefin of the general structure A14 may be made from a conjugated hydrocarbon terpene having a 1,3-conjugated diene and at least one additional olefinic bond (e.g., myrcene, farnesene, springene, or geranylfarnesene):

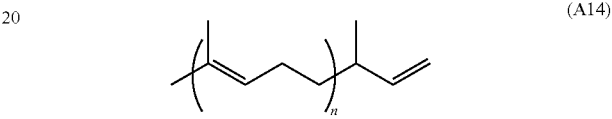

(A14)

where n=1, 2, 3, or 4. In one nonlimiting variation, a compound having the structure A14 may be derived from an unsaturated primary alcohol corresponding to the relevant hydrocarbon terpene (e.g., farnesol in the case of farnesene, or geraniol in the case of myrcene). The unsaturated primary alcohol may be exposed to a suitable catalyst under suitable reaction conditions to dehydrate the primary alcohol to form the terminal olefin A14.

In one non-limiting example, a stoichiometric deoxygenation-reduction reaction may be conducted to form compounds having structure A14 from a primary alcohol (e.g., farnesol or geraniol) of a hydrocarbon terpene. One prophetic example of such a reaction can be conducted according to a procedure described in Dieguez et al., "Weakening C—O Bonds: Ti(III), a New Reagent for Alcohol Deoxygenation and Carbonyl Coupling Olefination," J. Am. Chem. Soc. 2010, vol. 132, pp. 254-259, which is incorporated by reference herein in its entirety: A mixture of titanocene dichloride ($\eta^5$-$C_5H_5$)$_2$TiCl$_2$(Cp$_2$TiCl$_2$) (3.88 mmol) and Mn dust (2.77 mmol) in strictly deoxygenated tetrahydrofuran (THF) (7 mL) can be heated at reflux under stirring until the red solution turns green. Then, to this mixture can be added a solution of the primary alcohol (e.g., farnesol or geraniol) (1.85 mmol) in strictly deoxygenated THF (4 mL). After the starting materials disappear, the reaction can be quenched with 1N HCl and extracted with tert-butylmethyl ether (t-BuOMe). The organic phase can be washed with brine, filtered and concentrated in vacuo to yield a crude product, which can be purified, e.g., by column chromatography (hexane/t-BuOMe, 8:1) over silica gel column to afford a compound having structure A14 (e.g., 3,7,11-trimethyldodeca-1,6,10-triene if farnesol is used as the starting material).

Other reactions may be conducted to form compounds having structure A14 from a primary alcohol (e.g., farnesol or geraniol) of a hydrocarbon terpene. One prophetic example of such a reaction can be conducted according to another procedure described in Dieguez et al., "Weakening C—O Bonds: Ti(III), a New Reagent for Alcohol Deoxygenation and Carbonyl Coupling Olefination," J. Am. Chem. Soc. 2010, vol. 132, pp. 254-259, which is incorporated herein by reference in its entirety: A mixture of Cp$_2$TiCl$_2$ (0.639 mmol) and Mn dust (17.04 mmol) in thoroughly deoxygenated THF (8 mL) and under Ar atmosphere can be stirred until the red solution turned green. This mixture may then be heated at reflux and the corresponding trimethylsilylchloride (TMSCl) (8.52 mmol) may be added. The primary alcohol (e.g., farnesol) (1.92 mmol) in strictly deoxygenated THF (2 mL) may then be added. After the starting materials disappear, the reaction may be quenched with t-BuOMe, washed with 1 N HCl, brine, dried, and concentrated under reduced pressure. The resulting crude may be purified, e.g., by column chromatography (hexane/t-BuOMe, 8:1) on silica gel to afford compound having structure A14 (e.g., 3,7,11-trimethyldodeca-1,6,10-triene if farnesol is used as the starting material).

An olefinic feedstock as described herein may comprise any useful amount of the particular species (e.g., alphaolefinic species having structure A11, A12 or A15, monoolefinic species having structure A13, or unsaturated terminal olefin species having structure A14), made either by a partial hydrogenation route or by another route, e.g., as described herein. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% species having structure A11, A12, A13, A14, or A15. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodec-1-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3-methylene-7,11-dimethyldodecane. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodec-2-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7,11-trimethyldodeca-1,6,10-triene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethyloct-1-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethyloct-2-ene. In certain variations, an olefinic feedstock comprises at least about 1%, at least about 5%, at least about 10%, at least about 20%, at least about 30%, at least about 40%, at least about 50%, at least about 60%, at least about 70%, at least about 80%, or at least about 90% 3,7-dimethylocta-1,6-diene.

The alphaolefinic species of the conjugated hydrocarbon terpenes (e.g., compounds having structures A11, A12, A14 or A15) may be used as substitutes for, or as supplements to (e.g., in a co-feed configuration) conventional linear alphaolefins or branched alphaolefins in any industrial process known to utilize such alphaolefins, e.g., oligomerization utilizing alphaolefins, polymerization utilizing alphaolefins, hydroformylation utilizing alphaolefins, or carbonylation utilizing alphaolefins. The internal olefins species (e.g., compounds having structure A13) may be used as substitutes for, or as supplements to (e.g., in a co-feed configuration) conventional internal olefins in any industrial process known to utilize such internal olefins, e.g., oligomerization using internal olefins, polymerization using internal olefins, hydroformylation using internal olefins, or carbonylation using internal olefins. In some variations, the olefinic feedstocks comprising alphaolefinic species or internal olefinic species of partially hydrogenated hydrocarbon terpenes are suitable for catalytic reaction with one or more alphaolefins to form a mixture of isoparaffins comprising adducts of the terpene and the one or more alphaolefins. In some variations, at least a portion of the mixture of isoparaffins so produced may be used as a base oil. In some variations, the olefinic feedstocks comprising alphaolefinic species or internal olefinic species of partially hydrogenated hydrocarbon terpenes may be used to produce products such as alcohols, detergents, surfactants, polymers, plastics, rubbers, or oils.

It is noted that the processes and compositions provided herein have been described with respect to a limited number of embodiments and variations thereof. In certain embodiments, the processes may include one or more steps not specifically mentioned herein. In certain embodiments, steps may be performed in any sequence. In certain embodiments, one or more steps may be omitted or combined with another step but still achieve substantially the same results. Additional variations and modifications from the described embodiments are contemplated.

Each publication, patent, and patent application mentioned in this specification is incorporated herein by reference in its entirety, as if put forth fully below.

Although the claimed subject matter has been described in some detail by way of illustration and example for purposes of clarity of understanding, it will be readily apparent to those of ordinary skill in the art in light of the teachings herein that certain changes and modifications may be made thereto without departing from the spirit or scope of the appended claims.

The following examples are intended for illustrative purposes only and do not limit in any way the scope of the present invention.

EXAMPLES

Example 1. Preparation of 60% Hydrogenated β-Farnesene Containing No Detectable Amount of β-Farnesene and No Detectable Amount of Farnesane β-farnesene was filtered through activated alumina 20 mL of the alumina filtered β-farnesene was put into a reactor with 25 mg of 0.3 wt % Pd/Al$_2$O$_3$ (available from Johnson Matthey, PRICAT 309/7, 0.3% Pd/Alumina Trilobe 2.5 mm) that had been ground from pellets. The slurry so formed was stirred at about 1000 rpm. The reactor was heated to about 100° C. The reactor was pressurized to about 100 psig, and approximately 3 molar equivalents of hydrogen were delivered to the reactor (including auxiliary plumbing). The reaction was allowed to proceed for several hours. Analysis of the composition of the product by GC-MS (as described for Example 2 below) showed the sample had been 60% hydrogenated with the following distribution of species: 0 area % farnesene, 0 area % farnesane, 41.2 area % mono-olefin, 49.2 area % di-olefin, and 6.4 area % tri-olefin.

Examples 2-5. Preparation of Partially Hydrogenated Mono-Olefinic Feedstock from β-Farnesene Using Two Stage Hydrogenation For each of Examples 2-5, β-farnesene was hydrogenated to about 60% as described in Example 1 in a first stage, except that the β-farnesene was not treated with alumina prior to use, 100 mg of 0.3 wt % $Pd/Al_2O_3$ was used per 20 mL farnesene, and the reaction temperature was 160° C. In a second stage, the reactor was heated to a higher temperature (200° C. for Example 2, 220° C. for Example 3, 240° C. for Example 4, and 260° C. for Example 5), and the hydrogen pressure was decreased to about 20 psig in reactor pressure.

The composition of each of the partially hydrogenated products was analyzed by GC-MS and by GC/FID. Conditions for the GC-MS were as follows: Agilent 6890 GC, Column Agilent HP-1, 50 m×0.2 mm, 0.110 micron film, P/N 19091Z-005, Agilent 5973 Mass Selective Detector, oven ramp from 50° C. to 320° C., inlet in split mode (50:1 split ratio), helium as carrier gas, hexane as diluent, trans-β-farnesene or farnesane used as reference. Analysis of the composition of each of the products by GC/FID is as follows. An Agilent model 7890 GC having a flame ionization detector is used. A sample of partially hydrogenated farnesene is dissolved in n-heptane (at about 1 mg/mL) containing 100 μg/mL n-hexadecane that serves as a retention time reference. An Agilent model DB-17 ms GC column (60 m, 0.25 mm, 0.25 micron) is used that is made from 50% phenyl- and 50% methyl-polysiloxane. The parameters are as follows: inlet type is multi-mode or split-splitless, a split ratio 1:20 is used, a constant pressure of about 10.64 psi is used, inlet temperature is 250° C., flow rate is about 0.597 mL/min, carrier gas is hydrogen, injection volume is 1 microliter, the oven is set to have an initial temperature of 150° C., a run time of 20 minutes is used. The phenyl component in the column gives the stationary phase the ability to interact with the pi-electrons of the various double-bonds of the partially hydrogenated farnesene species. A variety of hydrogenated farnesene samples were analyzed on a GC-MS using the same column type, informing assignments as to molecular weight for each peak. β-farnesene and farnesane (at 0.5 mg/mL each) were used as assay calibration standards, and peak assignments as to molecular weight. A calibration table is created most easily from a chromatogram of 75% hydrogenated farnesene using the retention times and identifications suggested in Table 3. Systems will differ in the exact retention times, but the order remains the same. The integration parameters and compound identification windows were adjusted to identify each peak of the sample, to not split overlapping peaks except where appropriate (overlapping peaks having similar amplitudes are split), and to exclude the solvent peak. The GC-FID is used to quantify the weight contribution of each molecular weight constituent peak, proportional to the peak's area percent. Using a manual setup, each peak is given a unique name, an area of 1.0, and an amount corresponding to the molecular mass of the peak shown in Table 3. The n-hexadecane is given an amount of 1.0, an area of 1.0 and a multiplier of a very small number, e.g., $1\times10^{-10}$, and n-hexadecane is set as the only time reference peak. The calculation proceeds as follows. The sample is injected, separated by the column and detected. Peak areas are integrated and identified with the appropriate mass. The calibration report is set-up to multiply each peak's area percent times the calibration factor (amt/area) (the molecular mass). The resulting sum of amounts is reported as a number between 204 and 212, which represents the average molecular mass. The values for each mass level (204 to 212) are summed and divided by the overall sum to obtain and report the fraction for each mass level: Farnesane has a mass level of 212, hexahydrofarnesene has a mass level of 210, tetrahydrofarnesene has a mass level of 208, dihydrofarnesene has a mass level of 206, and farnesene (and its isomers) has a mass level of 204. The n-hexadecane is identified, but its amount contribution is very small and negligible. The peak area percent contributions for each molecular weight are summed and the average molecular weight of the entire sample is calculated to provide degree of hydrogenation. Results for Examples 2-5 are provided in Table 4, with compositional results measured by GC-MS and GC-FID both shown (GC-FID results in parentheses).

TABLE 3

Peak assignments as to molecular weight according to GC-MS

| Mass | Retention Time (approx.) (min) | |
|---|---|---|
| 210a | 9.32 | |
| 210b | 9.45 | |
| 210c | 9.53 | |
| 212 | 9.67 | Farnesane |
| 210i | 10.09 | |
| 210d | 10.22 | |
| 210e | 10.32 | |
| 208a | 10.44 | |
| 210f | 10.56 | |
| 208b | 10.64 | |
| 210g | 10.91 | |
| 208c | 11.03 | |
| 208d | 11.14 | |
| 210h | 11.29 | |
| 208e | 11.49 | |
| 208f | 11.58 | |
| 208q | 11.73 | |
| 208g | 11.99 | |
| 208s | 12.05 | |
| 208h | 12.15 | |
| 208i | 12.28 | |
| 208j | 12.36 | |
| 206a | 12.48 | |
| 208u | 12.54 | |
| 208k | 12.59 | |
| 208l | 12.84 | |
| 208m | 12.94 | |
| 208n | 13.05 | |
| 208o | 13.16 | |
| 208t | 13.41 | |
| 208p | 13.55 | |
| 208r | 13.64 | |
| 206b | 13.94 | |
| 206n | 14.02 | |
| 206m | 14.09 | |
| 206c | 14.38 | |
| 206d | 14.60 | |
| 206e | 14.87 | |
| 206l | 15.12 | |
| 206f | 15.20 | |
| 206g | 15.38 | |
| 206h | 15.52 | |
| 206i | 15.68 | |
| 204 | 16.10 | Farnesene |
| 206j | 16.18 | |
| 206k | 17.03 | |
| — | 18.60 | n-Hexadecane |

TABLE 4

| Example | Catalyst | First stage hydrogenation pressure (psig) | First stage T (° C.) | Second stage hydrogenation pressure (psig) | Second stage T (° C.) | % hydrogenation | area % farnesane | area % hexahydrofarnesene | area % tetrahydrofarnesene | Area % dihydrofarnesene | Area % farnesene |
|---|---|---|---|---|---|---|---|---|---|---|---|
| 2 | 0.3 wt % Pd/Al$_2$O$_3$ | 100 | 160 | 20 | 200 | 78 (77)$^c$ | 17.2 (19.1) | 74.8 (69.5) | 8.0 (11.3) | 0 (0.1) | 0 (0) |
| 3 | 0.3 wt % Pd/Al$_2$O$_3$ | 100 | 160 | 20 | 220 | 75 (75)$^c$ | 11.5 (13.6) | 79.0 (73.8) | 9.4 (12.6) | 0 (0.1) | 0 (0) |
| 4 | 0.3 wt % Pd/Al$_2$O$_3$ | 100 | 160 | 20 | 240 | 75 (75)$^c$ | 8.4 (10.7) | 82.9 (77.6) | 8.7 (11.6) | 0 (0) | 0 (0) |
| 5 | 0.3 wt % Pd/Al$_2$O$_3$ | 100 | 160 | 20 | 260 | 73 (72)$^c$ | 6.3 (7.8) | 80.5 (74.1) | 13.2 (18.0) | 0 (0.1) | 0 (0) |
| 6 | 5 wt % Pd/C | 0-970 | 40-50 | 0-970 | 140 | 71$^{a,b}$ | 5 | 74** | 21** | 0* | 0* |
| 7 | 5 wt % Pd/C | 0-970 | 40-50 | 0-970 | 140 | 78$^{a,b}$ | 8 | 76** | 16** | 0* | 0* |

*Assumed to be zero, based on GC-MS
*Calculated from GC-MS area % measured for farnesane and Bromine index as described in Examples 6 and 7
$^a$% hydrogenation measured by Bromine index of total sample.
$^b$sample characterized by GC-MS using a 50 m column as described.
$^c$% hydrogenation measured by GC-MS and GC-FID. Area % numbers in parentheses refer to GC FID area %; area % numbers not in parentheses refer to GC-MS area %.

Example 6. Preparation of 71% Hydrogenated Olefinic Feedstock from β-Farnesene The instant example provides a partially hydrogenated mono-olefinic farnesene feedstock prepared according to the staged hydrogenation methods described above.

To a one liter reactor (Parr Instrument Co., Moline, Ill.) was added 499.4 g microbial-derived β-farnesene (97% pure, Amyris, Emeryville Calif.) which had been distilled with a wiped film distillation apparatus and to which 100 ppmw 4-tert-butylcatechol was added. To the β-farnesene was added 1.5 g Pd/C (5 wt %) catalyst (Pd on activated carbon, surface area 1050 m$^2$/g, pore volume 0.61 cc/g, Strem Chemicals, Newburyport, Mass.) to make a slurry. The slurry was stirred at about 250-300 rpm. The reactor was pressurized to 970 psig with hydrogen gas. The 970 psig hydrogen gas corresponded to about 0.5 molar equivalents of hydrogen. After the pressure in the reactor decreased to 0 psig, indicating the hydrogen had been substantially consumed, another pulse of hydrogen was added to pressurize the reactor to 970 psig. A total of 6 pulses of hydrogen were added to the reactor in this manner, with the first two pulses auto-heating the reactor to about 40° C.-50° C. Towards the end of consumption of the third pulse, the reactor was heated to about 140° C. to complete the consumption of the hydrogen. For the 4$^{th}$, 5$^{th}$, and 6$^{th}$ pulses, the reactor was heated to about 140° C. Following completion of the 6$^{th}$ pulse, the slurry was removed from the reactor. The catalyst was removed from the slurry by filtration through silica gel, yielding 453.4 of partially hydrogenated farnesene characterized by GC-MS as described for Example 2, except that the samples were diluted in ethyl acetate, as shown in FIG. 1. The bromine index of the partially hydrogenated farnesene was measured according to ASTM 2710 using a titrant strength of 0.02 M bromide-bromate, and indicated the sample was 71% hydrogenated. The farnesane content in the hydrogenated sample was measured to be 5% by GC-MS, based on the total hydrogenated sample. The GC-MS spectrum showed no detectable amount of farnesene or dihydrofarnesene. The area percents of hexahydrofarnesene and tetrahydrofarnesene in the hydrogenated sample were calculated algebraically using the % hydrogenation in the total sample determined from the measured bromine index and the measured area % for the saturated component. Results are summarized in Table 4. The area % farnesane is measured to within +/−2%, and the area % of hexahydrofarnesene and tetrahydrofarnesene are measured to within +/−4% accuracy.

Example 7. Preparation of a 78% Hydrogenated Olefinic Feedstock from β-Farnesene The instant example provides another example of a mono-olefinic farnesene feedstock prepared according to the methods described herein.

Figure 2:
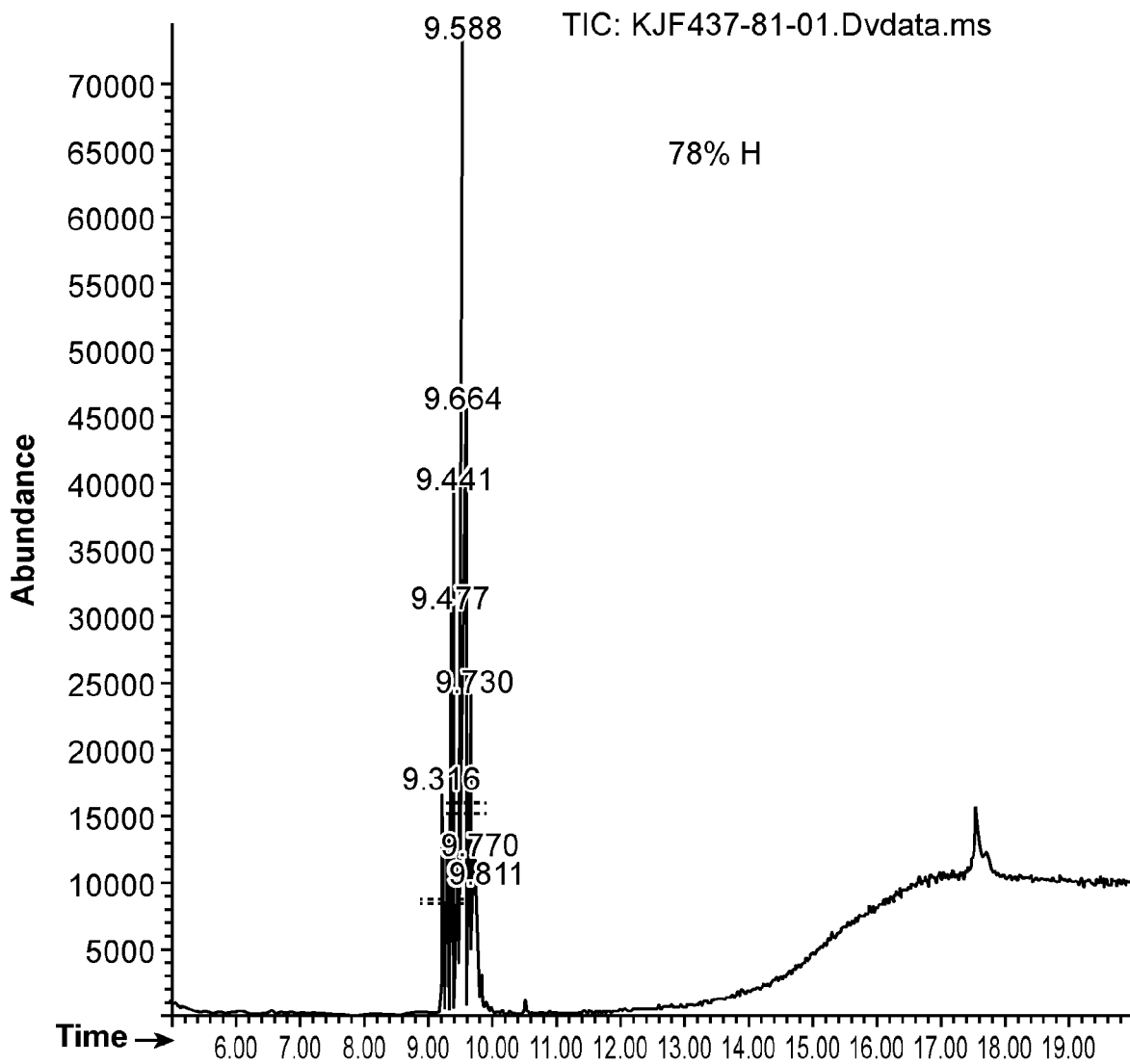
FIG. 2 provides a GC-MS spectrum of β-farnesene that is 78% hydrogenated.

Example 7 was prepared and analyzed as in Example 6. FIG. 2 shows the GC-MS spectrum for Example 7. Results are summarized in Table 4.

Example 8. Preparation of a 25% Hydrogenated Olefinic Feedstock from β-Farnesene The instant example provides a dihydrofarnesene feedstock prepared according to the methods described herein.

Example 8 was carried out as in Example 6, except that only two pulses of hydrogen gas (corresponding to a total of one molar equivalent) were delivered to the reactor. The results were analyzed by GC-MS and NMR. A $^1$H NMR spectrum of the product is shown in FIG. 3. By NMR and GC-MS, the reaction product included the following species in the indicated molar percents:

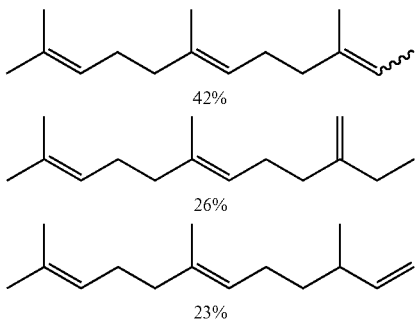

42%

26%

23%

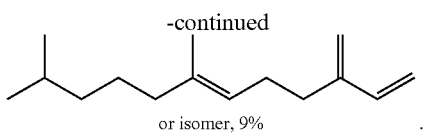

or isomer, 9%

Example 9: Alternate Preparation of a 25% Hydrogenated Olefinic Feedstock from β-Farnesene The instant example provides another example of a dihydrofarnesene feedstock prepared according to the methods described herein.

β-farnesene (26.0 g, 0.127 mol) and 0.26 g of Lindlar's catalyst (5% Pd/Pb on $CaCO_3$, available from Sigma Aldrich) were placed in a 100 mL autoclave. The apparatus was evacuated/flushed with $N_2$ three times and then charged with one equivalent of hydrogen (690 psig). The mixture was stirred (500 rpm) at 19° C. for 18 hours. The catalyst was removed by filtration to afford 25.8 g (98.5%) of a mixture of the following five compounds, with their corresponding molecular ion weights.

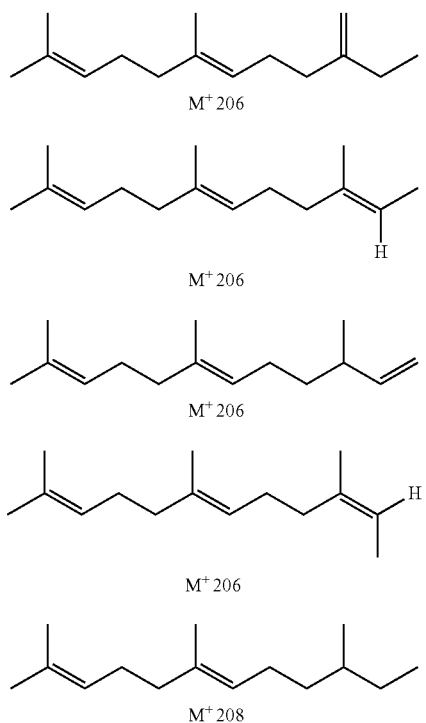

The mixture was analyzed using GC/MS as described for Example 2, and showed the following distribution of species:

| $R_T$ (Min.)* | $M^+$ | % Run #1 | % Run #2 |
|---|---|---|---|
| 9.63 | 206 | 21.4 | 21.6 |
| 9.76 | 208 | 13.5 | 11.9 |
| 9.84 | 206 | 25.1 | 26.6 |
| 9.89 | 206 | 28.7 | 28.5 |
| 9.93 | 206 | 10.3 | 9.8 |

Example 10. Preparation of 75% Hydrogenated Olefinic Feedstock from β-Farnesene Using Single Stage Controlled Hydrogenation The instant example provides an additional example of a mono-olefinic farnesene feedstock prepared according to the methods described herein.

A catalyst (5 wt % Pd/C, available from Strem Chemicals, as described in Example 6 above) was immersed into β-farnesene (Amyris, as described in Example 6) to form a slurry in a closed reactor at a loading of 3.1 g/kg liquid. The slurry was agitated. The reactor was purged with nitrogen using 3 pressure/vacuum cycles, pressuring to 100 psig with nitrogen and evacuating to 3 or less psia in each cycle. After the third cycle, the reactor was left under 3 or less psia nitrogen, and agitation was stopped. The reactor was pressurized to 50 psig with hydrogen and allowed to stabilize. After stabilization, hydrogen was delivered to the reactor at 50 psig while the slurry was agitated. The reactor was heated to 100° C. The cumulative uptake of hydrogen was monitored using a flow totalizer. As the exothermic reaction proceeded the reactor was heated or cooled as appropriate to maintain the reaction temperature at 100° C. After 3.0 molar equivalent of hydrogen was consumed (as measured by the flow totalizer), the hydrogen flow and agitation were stopped. The reactor was purged with nitrogen as described above, leaving about 15 psig overpressure of nitrogen in the reactor headspace. The reactor was cooled to less than about 30° C., and the catalyst was filtered from the liquid by filtration. The partially hydrogenated farnesene was analyzed using GC-FID and GC-MS using an Agilent DB-17 ms 60 m column as described above for Examples 2-5, and was also characterized by GC-MS using an HP-1 50 m long×200 micron ID×110 nm film thickness column and using hexane as a solvent as described for Example 2. GC-FID results are shown in parentheses. Poorer resolution of peaks was achieved using the 50 m column, leading to increased need for splitting overlapping areas. Peak areas corresponding to each of farnesene, farnesane, dihydrofarnesene, tetrahydrofarnesene, and hexahydrofarnesene were determined to result in the species distribution as shown in Table 5. The sample was calculated to have an average molecular weight of 210.0 by GC-FID, corresponding to 75% hydrogenated. The Bromine number of the sample was measured according to ASTM D1159 to be 80.6, and is estimated to be 76 if the substance responds to bromine as a triunsaturate (refer to Table 1).

Example 11. Preparation of 78% Hydrogenated Olefinic Feedstock from β-Farnesene Using Single Stage Controlled Partial Hydrogenation The instant example provides an additional example of a mono-olefinic farnesene feedstock prepared according to the methods described herein.

Example 11 was carried out as in Example 10, except that 3.1 molar equivalents of hydrogen were consumed during the reaction, and a catalyst loading of 2.1 g/kg was used. The partially hydrogenated farnesene was analyzed using GC-FID and GC-MS as described for Example 10. Results are shown in Table 5. The sample was calculated to have an average molecular weight of 210.3 by GC-FID, corresponding to 78% hydrogenated. The Bromine number of the sample by GC-was measured according to ASTM D1159 to be 71.9, and is estimated to be 65.9 if the substance responds to bromine as a triunsaturate (refer to Table 1).

Example 12. Preparation of 67% Hydrogenated Olefinic Feedstock from β-Farnesene Using Single Stage Controlled Partial Hydrogenation The instant example provides an additional example of a farnesene feedstock comprising predominantly di-olefins and mono-olefins prepared according to the methods described herein.

Example 12 was carried out as in Example 10, except that 2.5 molar equivalents of hydrogen were consumed during the reaction, and a catalyst loading of 2.1 g/kg was used. The partially hydrogenated farnesene was analyzed using GC-MS as described for Example 10. Results are shown in Table 5. The sample was calculated to have an average molecular weight of 209.3 by GC-FID, corresponding to 67% hydrogenated. The Bromine number of the sample was measured according to ASTM D1159 to be 112.9, and is estimated to be 109.2 if the substance responds to bromine as a tri-unsaturate (refer to Table 1).

Example 13. Preparation of 85% Hydrogenated Olefinic Feedstock from β-Farnesene Using Single Stage Partial Hydrogenation The instant example provides an additional example of a mono-olefinic farnesene feedstock prepared according to the methods described herein.

Example 13 was carried out as in Example 10, except that 3.35 molar equivalents of hydrogen were consumed during the reaction, and a catalyst loading of 2.1 g/kg was used. The partially hydrogenated farnesene was analyzed using GC-MS as described for Example 10. Results are shown in Table 5. The sample was calculated to have an average molecular weight of 210.8 by GC-FID, corresponding to 85% hydrogenated. The Bromine number of the sample was measured according to ASTM D1159 to be 52.7, and is estimated to be 49.2 if the substance responds to bromine as a tri-unsaturate (refer to Table 1).

TABLE 5

| Example | % hydrogenation | % farnesane | % hexahydrofarnesene | % tetrahydrofarnesene | % dihydrofarnesene | % farnesene |
|---|---|---|---|---|---|---|
| 10[a] | 75 (75)** | (18.3%) 16.0% | (65.3%) 68.6% | (16.4%) 15.2% | (0) <0.3% | (0) <0.3% |
| 11[a] | 78 (78)** | (24.9%) 23.3% | (64.6%) 66.6% | (10.4%) 10.1% | (0) <0.3% | (0) <0.3% |
| 12[a] | 63 (67)** | (8.5%) 7.8% | (50.5%) 49.8% | (40.5%) 34.1% | (0.5%) 2% | (0) 6% |
| 13[a] | 85 (84)** | (40.9%) 37.7% | (58.3%) 58.8% | (0.8%) 3.0% | (0) <0.3% | (0) <0.3% |

[a]% Samples characterized by GC-MS using 50 m column and GC-FID using 60 m column as described in Example 2. Area % numbers in parentheses refer to those measured by GC-FID; area % numbers not in parentheses refer to those measured by GC-MS.

Example 14. Preparation of 3,7,11-Trimethyldodec-1-Ene (Method A)

The instant example provides an example of an alphaolefin prepared according to the methods described herein.

The compound 3,7,11-trimethyldodec-1-ene was synthesized according to the following reaction: a) Commercially available farnesol (Compound 1 below) is hydrogenated in the presence of a palladium catalyst to produce 3,7,11-trimethyl-1-dodecanol (Compound 2 below). b) Stearoyl chloride (Compound 4 below) is prepared from stearic acid (Compound 3 below) and thionyl chloride. c) Compound 4 is reacted with Compound 2 and pyridine to form Compound 5 below. d) Compound 5 is distilled under heat to produce stearic acid and 3,7,11-trimethyldodec-1-ene (Compound 6 below).

Schematic Reaction for Method A for preparation of 3,7,11-trimethyl-1-dodec-1-ene from farnesol

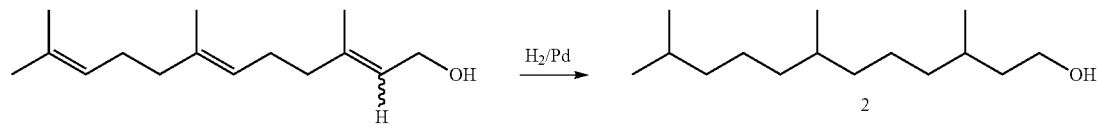

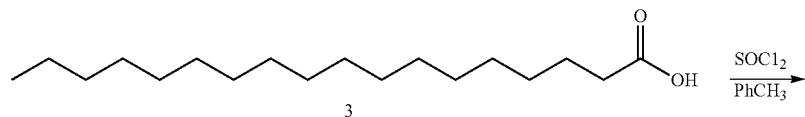

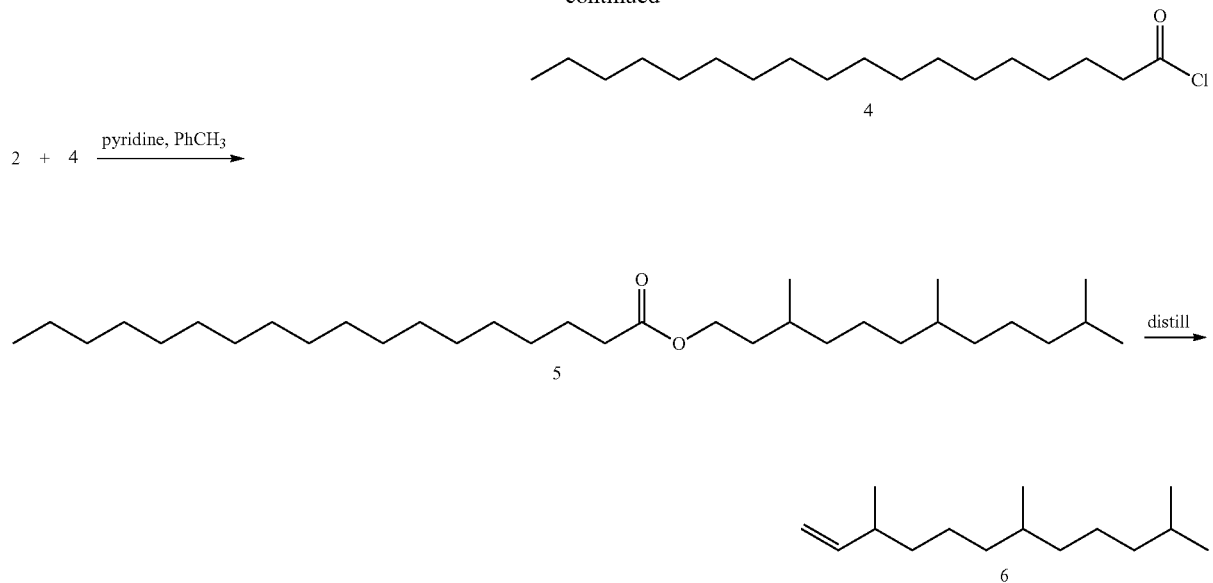

a. Preparation of 3,7,11-trimethyl-1-dodecanol (Compound 2) from Commercially Available Farnesol Farnesol (95% pure, St. Louis, Mo., 202 g, 0.81 mol, ca. 3:1 mixture of 2E/2Z isomers, available from Sigma-Aldrich as catalog No. F203), 0.5 g of 5% Pd/C (matrix activated carbon support, available from Sigma-Aldrich as catalog No. 205680) and 200 mL of hexane were placed in a 1 L autoclave. After three evacuate/$N_2$ flush cycles the reactor was charged with 400 psig of $H_2$, and stirred at 500 rpm. The reaction began to take up $H_2$ and liberate heat but stalled at approximately 50% completion. An additional 0.5 g of Pd/C was added to the cooled reactor under $N_2$. The reaction was heated to 75° C. under 600 psig of $H_2$. After 48 hr the reactor was cooled, the catalyst removed by vacuum filtration and the hexane under reduced pressure. A small amount of 2,6,10-trimethyldodecane was removed by vacuum distillation to afford 151 g (82.0%) of 3,7,11-trimethyl-1-decanol (Compound 2) as a colorless oil.

b. Preparation of Stearoyl Chloride (Compound 4)

A 2 L three-necked round-bottomed flask equipped with a mechanical stirrer, reflux condenser, heating mantle and pressure equalizing addition funnel was charged with stearic acid (97.6 g, 0.343 mol) and 750 mL of toluene. The mixture was stirred, heated to refluxing. Thionyl chloride (26.3 mL, 42.8 g, 0.360 mol) was added over a period of 30 minutes. The mixture was refluxed for an additional three hours and at ambient temperature over night. A small amount (12.0 g) of unreacted stearic acid was removed by vacuum filtration and the toluene removed under reduced pressure to afford 90.3 g (99.0% based on recovered starting material) of stearoyl chloride (Compound 4) as a light yellow oil.

c. Preparation of (3,7,11-Trimethyl-1-dodecyl) Stearate (Compound 5)

A 2 L three-necked round-bottomed flask equipped with a mechanical stirrer, thermometer and pressure equalizing addition funnel was charged with 68.8 g (0.301 mol) of Compound 2, pyridine (29.2 g, 0.361 mol) and 300 mL of toluene. A solution of steroyl chloride (Compound 4) in 400 mL of toluene was added dropwise over 20 minutes with rapid stirring and occasional warming of the addition funnel with a heat gun to prevent the acid chloride from precipitating. As the addition progressed, a granular precipitate of pyridine hydrochloride formed that became quite thick by the end of the reaction. The mixture was stirred for an additional three hours at which time the pyridine hydrochloride was removed by vacuum filtration. Removal of the solvent by rotary evaporation afforded an oil that was dissolved in 250 mL of hexane and cooled to 4° C. to precipitate unreacted stearic acid. After filtration the hexane was removed under reduced pressure to afford 128 g of crude Compound 5 containing unreacted Compound 2. The oil was passed down a 7×23 cm column of silica gel with hexane to afford 87.7 g (58.9%) of Compound 5 as colorless oil.

d. Preparation of 3,7,11-trimethyldodec-1-ene (6)

(3,7,11-Trimethyl-1-dodecyl) stearate (Compound 5, 87.7 g, 0.177 mol) was placed in a 200 mL round-bottomed flask equipped with a distillation head, magnetic stirrer and heating mantle and pyrolyzed at ambient pressure to afford crude Compound 6 (bp 230° C.) contaminated with a small amount of stearic acid. The crude product was slurried with 200 mL of pentane and vacuum filtered. The last traces of stearic acid were removed by passing the filtrate through a 40×35 mm pad of silica gel which resulted in the isolation of 31.9 g (85.5%) of Compound 6 as a colorless oil after removal of the pentane under reduced pressure.

Example 15. Preparation of 3,7,11-trimethyldodec-1-ene (Method B)

Example 15 provides an alternate synthesis (Method B) of 3,7,11-trimethyldodec-1-ene from farnesol. In step a) of Method B, 3,7,11-trimethyl-1-decanol (Compound 2, as prepared in Example 9 above) is reacted with diphenylcarbamoyl chloride (Compound 7 below, available from Sigma Aldrich) to form 3,7,11-trimethyl-1-dodecyl-N,N-diphenyl-carbamate (Compound 8 below). In step b) of Method B, Compound 8 is prepared from Compound 8.

Method B for preparation of 3,7,11-trimethyl-1-dodec-1-ene from farnesol

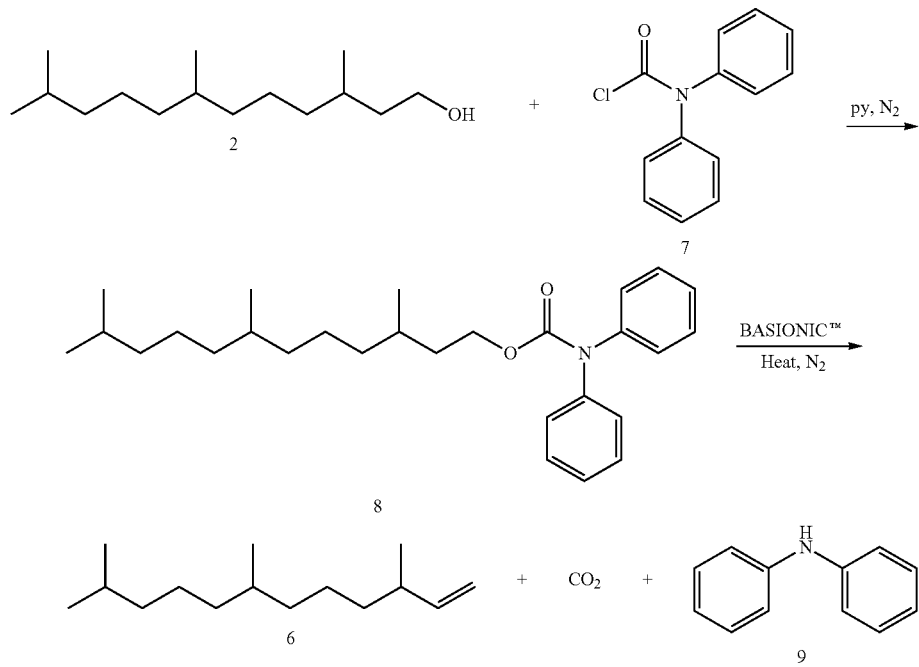

a. Preparation of 3,7,11-Trimethyl-1-dodecyl-N,N-diphenylcarbamate (Compound 8)

A 50 mL round-bottomed flask equipped with a magnetic stirrer and reflux condenser attached to a nitrogen inlet was charged with Compound 2, as prepared above in Example 9 (4.93 g, 21.6 mmol), diphenylcarbamoyl chloride (Compound 7, available from Sigma Aldrich, 5.50 g, 23.8 mmol) and 6.5 mL of freshly distilled (NaOH) pyridine. The flask was immersed in an oil bath maintained at 115° C. for 15 hours. The mixture was allowed to cool and partitioned between ether (20 mL) and water (100 mL). The layers were separated and the aqueous phase washed with 4×15 mL portions of ether. The extracts were combined, dried (MgSO$_4$) and the solvent removed under reduced pressure to afford 9.17 g (100%) of crude 8 as an orange oil that was subsequently passed through a 1×4.5 cm pad of silica gel with 10% ethyl acetate/hexane to remove some unreacted Compound 7.

b. Preparation of 3,7,11-Trimethyldodec-1-ene (Compound 6)

A 50 mL round-bottomed flask equipped with a magnetic stirrer, heating mantle and short path distillation head was charged with 5.0 g (11.8 mmol) of Compound 8 and 5.0 g of BASIONIC™ (available from BASF Corporation) ionic liquid. The mixture was strongly heated which resulted in the isolation of 2.6 g of a mixture of Compound 6 and Compound 9 (by $^1$HNMR) which was not separated.

Examples 16-31. Preparation of 75-78% Hydrogenated β-Farnesene

For each of Examples 16-31, a 1-Liter reactor with an H$_2$ reservoir was charged with 660 mL β-farnesene as described in Example 6. Catalyst as specified in Table 5 was mixed into the farnesene and the reactor was stirred at 1000 rpm, except Example 16, which was stirred at 500 rpm. After purging as described in Example 6, the reactor was pressurized with hydrogen to 100 psig (external). The reactor was allowed to self-heat as provided in Table 6, and then heated using an external heater to a first stage reaction temperature of 100° C. After a decline in hydrogenation rate to near zero indicated the 1.5 equivalents of hydrogen had been consumed, the temperature was increased in a second stage as shown in Table 6. For Examples 16-23, 27-28 and 30, hydrogen pressure in the second stage was the same as in the first stage (100 psig). For Examples 24-26, 29 and 31, hydrogen pressure in the second stage was lowered relative to the first stage, as shown in Table 6. For Example 31, the hydrogen pressure was initially reduced to 10 psig in the second stage after 1.5 equivalents hydrogen were consumed, then increased to 20 psig after 2.3 equivalents hydrogen were consumed, and increased again to 30 psig after 2.9 equivalents hydrogen were consumed.

In Examples 16-26, 28-29, and 31, 0.3 wt % Pd/Al$_2$O$_3$ was supplied by Johnson Matthey (Type 335, powder, size D50:45). In Example 27, 5 wt % Pd/C as in Example 6 is used. In Example 30, 0.5 wt % Pd/titanium silicate (powder, D50=25 µm, available from Strem Chemicals) is used. In Examples, 23-27, and 29-31, a catalyst loading of 18 ppm Pd in farnesene was used. In Example 28, a catalyst of 14 ppm Pd in farnesene was used.

Figure 4A:
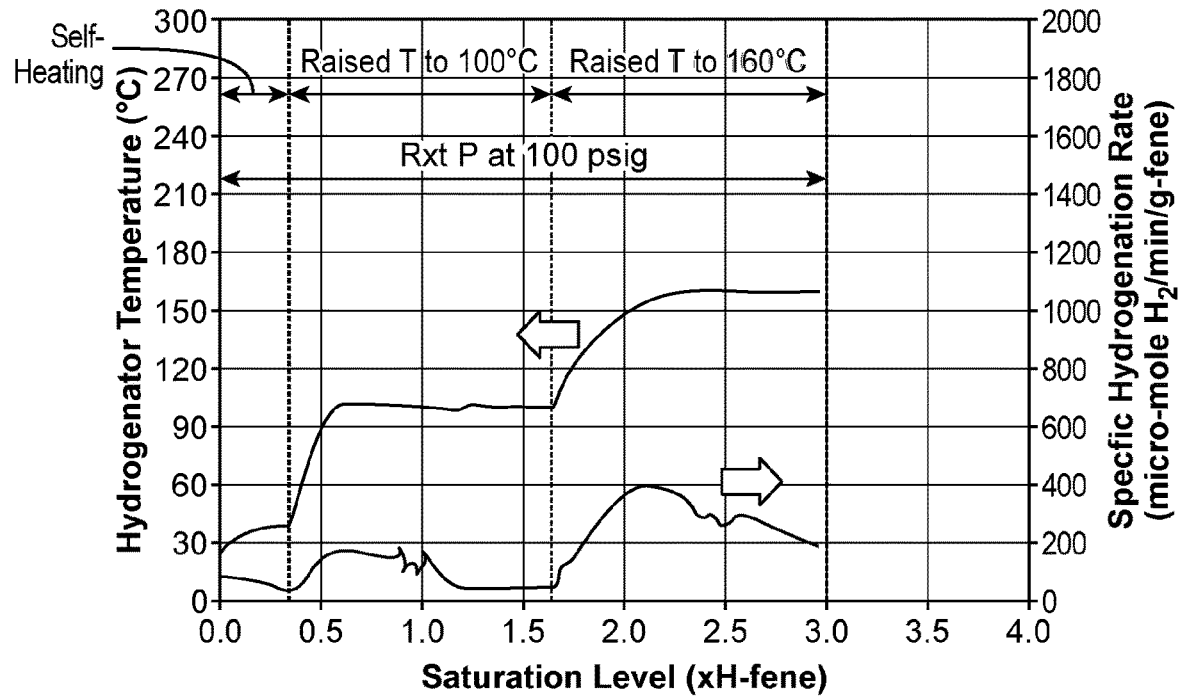
FIG. 4A provides a reaction profile for Example 23.
Figure 4B:
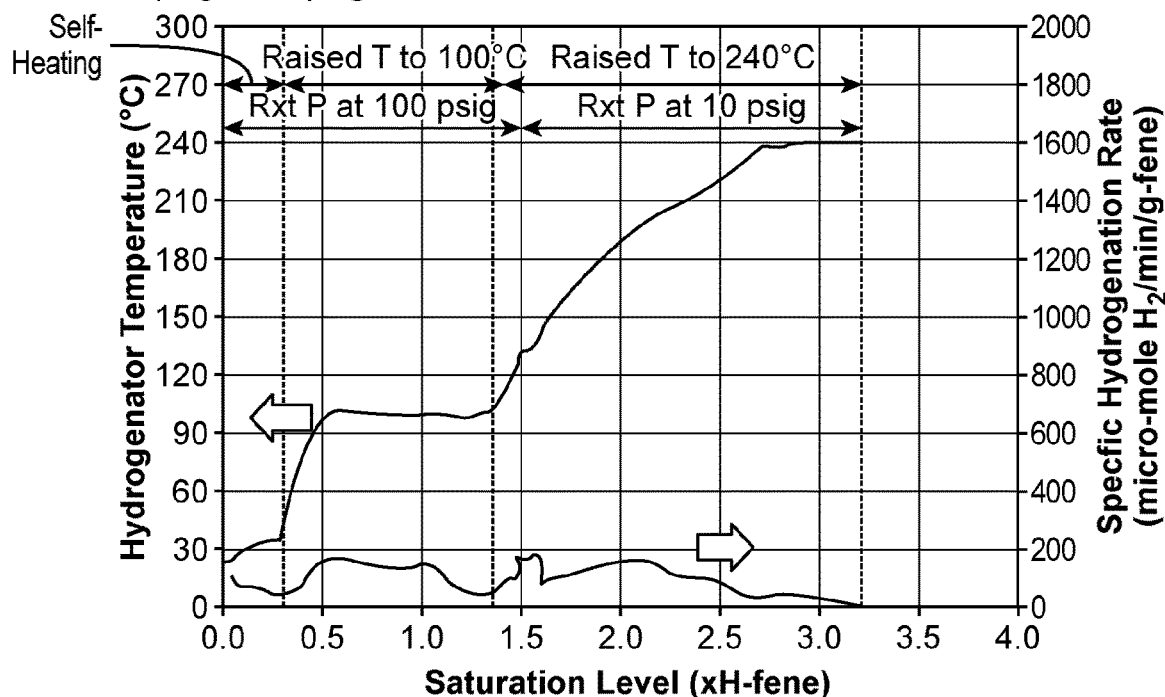
FIG. 4B provides a reaction profile for Example 25.
Figure 5A:
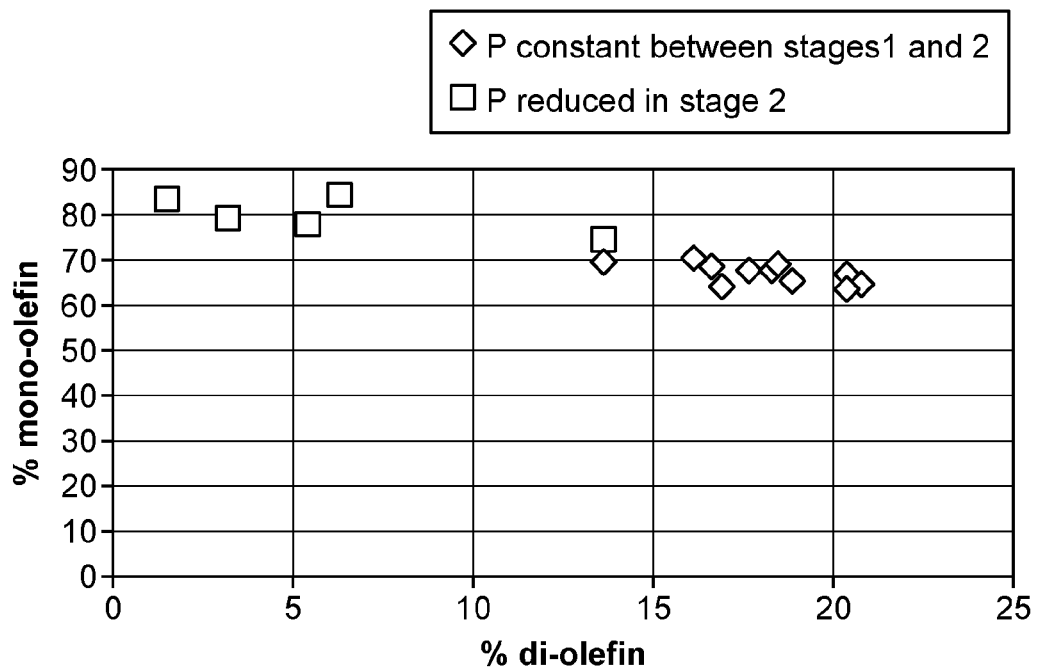
FIGS. 5A-5F provide plots of experimental results for Examples 16-31.
Figure 5B:
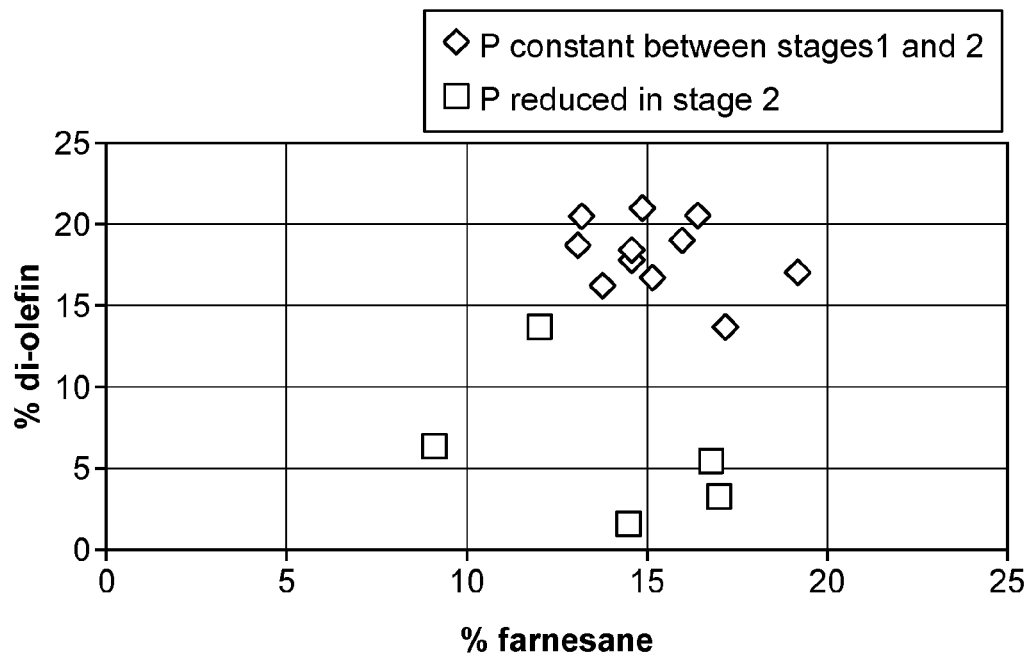
Figure 5C:
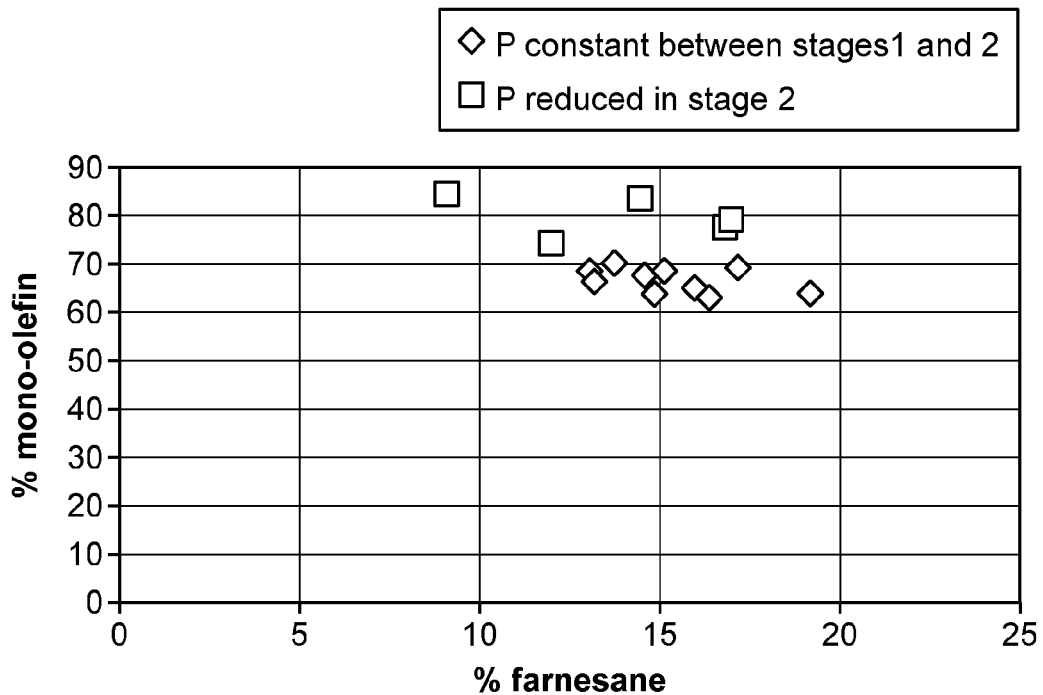
Figure 5D:
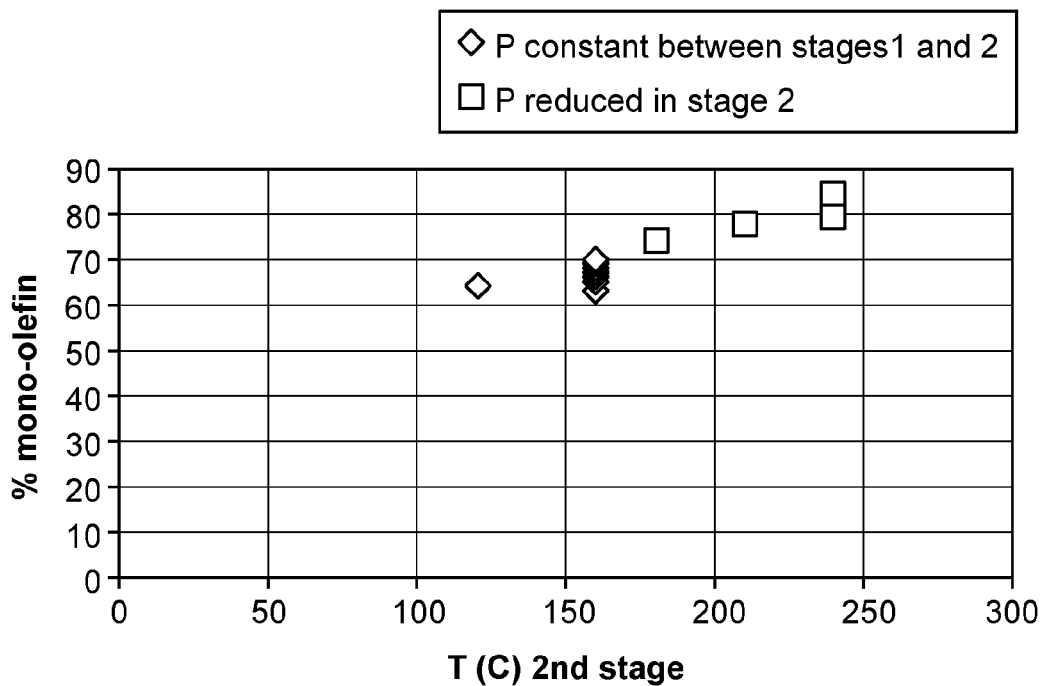
Figure 5E:
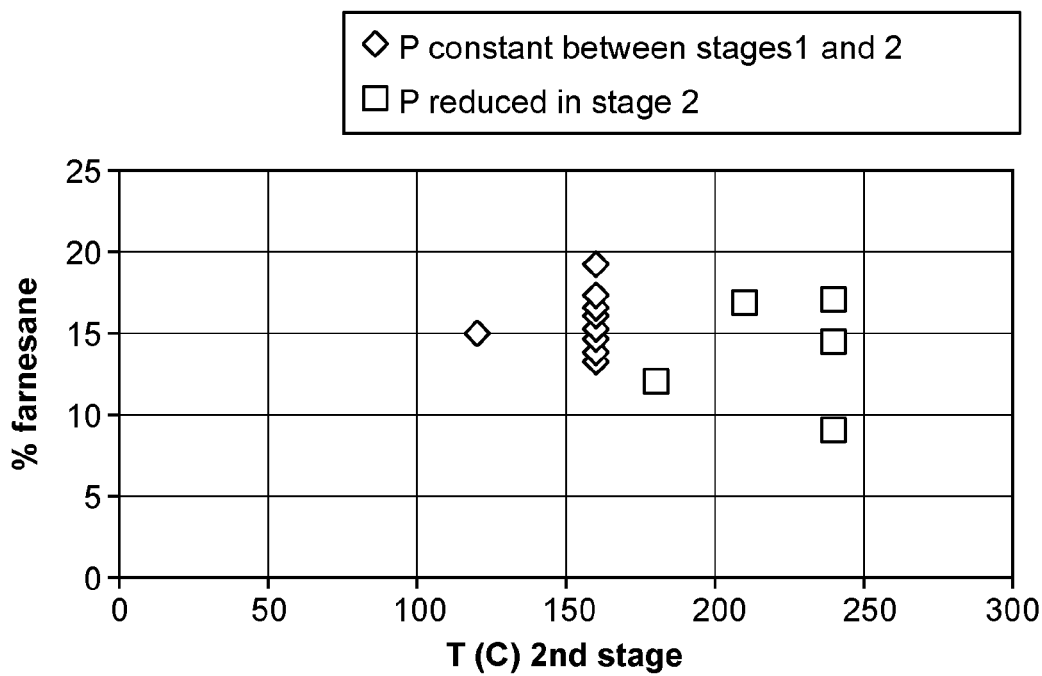
Figure 5F:
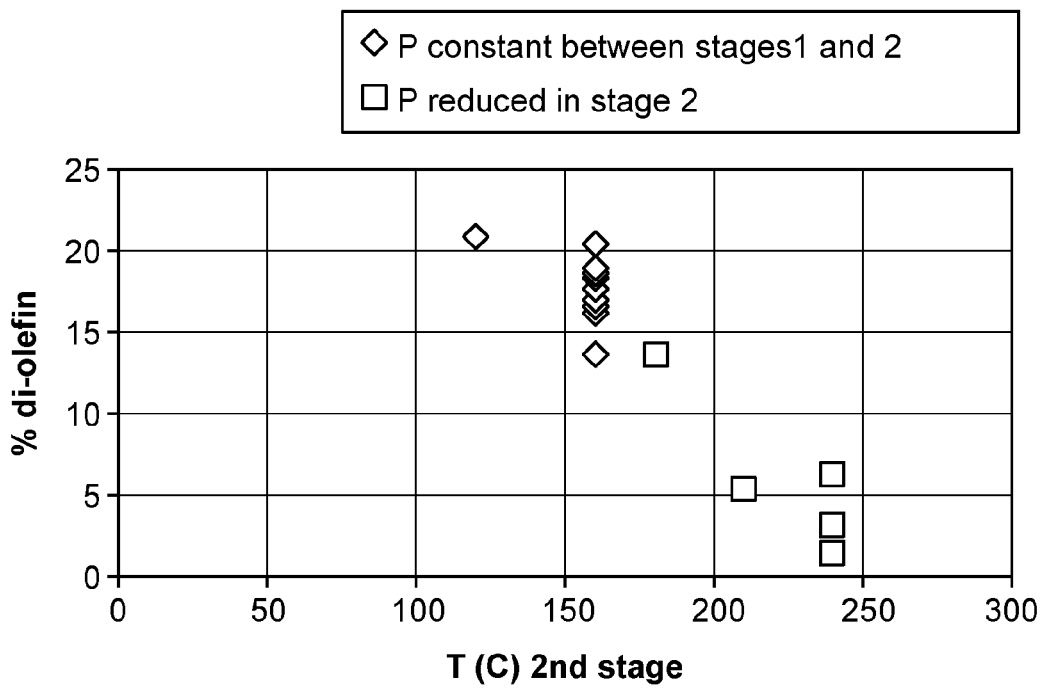

FIG. 4A illustrates the temperature and specific hydrogenation rate (µmole H$_2$/min/g-farnesene) for the hydrogenation process of Example 23. In Example 23, hydrogen pressure is 100 psig in the first and second stages. FIG. 4B illustrates the temperature and specific hydrogenation rate for the hydrogenation process of Example 25. In Example 25, hydrogen pressure is 100 psig in the first stage, and is reduced to 10 psig in the second stage.

Table 6 provides total equivalents of hydrogen consumed, run time, % mono-olefin, % di-olefin, % tri-olefin, and % farnesane for each of Examples 16-31. The relative quantities of the species were measured by GC-FID as described above for Example 2. For each of Examples 16-31, the amount of tetra-olefin present was negligible. Results are plotted in FIGS. 5A-5F. As shown in FIGS. 5A-5F, % mono-olefin is increased while % di-olefin is reduced by increasing temperature in the second stage and reducing pressure in the second stage. A composition comprising 75% or greater (in some cases 80% or greater) mono-olefin and 5% or less di-olefin is achieved using a second stage temperature of 210-240° C. and a second stage pressure of 10 psig.

The effect of pretreatment of β-farnesene to remove oxygenates and other polar substances was investigated. For Example 16, the β-farnesene was filtered with silica gel (1.1 L farnesene/400 ml silica gel). For Examples 17-18, the β-farnesene was filtered with basic alumina (0.9 kg farnesene/0.45 kg alumina basic, standard activity 1). For Example 19, the β-farnesene was treated by mixing with 0.45 kg Selexorb™ CDX ⅛" and stirred 1 hour. For Example 20, the β-farnesene was treated with caustic, washed with water, and treated with Celite. For Example 21, the β-farnesene was treated with 1 wt % NaOH beads. For Example 22, the β-farnesene was treated with 0.2 wt % NaOH. For Examples 23-30, the β-farnesene had been redistilled and filtered through basic alumina prior to use. For Example 31, the 13-farnesene was not pretreated. The untreated farnesene exhibited very slow hydrogenation rates. Specific hydrogenation rates were measured after 2 equivalents of hydrogen had been consumed: Example 16 (silica gel treatment), specific hydrogenation rate of 400 μmole $H_2$/min/g-farnesene; Example 17 (basic alumina treatment), specific hydrogenation rate of 1200 μmole $H_2$/min/g-farnesene; Example 19 (Selexorb™ treatment), specific hydrogenation rate of 600 μmole $H_2$/min/g-farnesene; Example 20 (caustic-water treatment), specific hydrogenation rate of 210 μmole $H_2$/min/g-farnesene; Example 21 (1 wt % NaOH bead treatment), specific hydrogenation rate of 400 μmole $H_2$/min/g-farnesene; Example 22 (0.2 wt % NaOH bead treatment), specific hydrogenation rate of 400 μmole $H_2$/min/g-farnesene.

TABLE 6

Examples 16-31

| Ex. | Self-heat | T (° C.) stage 1 | T (° C.) stage 2 | P $H_2$ (psig) stage 1 | P $H_2$ (psig) stage 2 | Catalyst | Run time | Mol. $H_2$ | % monoolefin | % diolefine | % triolefin | % farnesane |
|---|---|---|---|---|---|---|---|---|---|---|---|---|
| 16 | To 39° C. | 100 | 160 | 100 | 100 | 3300 mg 0.3 wt % Pd/Al$_2$O$_3$ | 2 h 22 min | 2.97 | 69.9 | 16.1 | 0.25 | 13.75 |
| 17 | To 71° C. | 100 | 160 | 100 | 100 | 3300 mg 0.3 wt % Pd/Al$_2$O$_3$ | 1 h 35 min | 2.94 | 68.23 | 18.51 | 0.19 | 13.07 |
| 18 | To 56° C. | 100 | 120 | 100 | 100 | 3300 mg 0.3 wt % Pd/Al$_2$O$_3$ | 1 h 9 min | 2.91 | 63.76 | 20.79 | 0.5 | 14.88 |
| 19 | To 92° C. | 100 | 160 | 100 | 100 | 3300 mg 0.3 wt % Pd/Al$_2$O$_3$ | 1 h 7 min | 2.92 | 66.19 | 20.37 | 0.25 | 13.19 |
| 20 | To 65° C. | 100 | 160 | 100 | 100 | 3300 mg 0.3 wt % Pd/Al$_2$O$_3$ | 1 h 59 min | 2.97 | 64.89 | 18.89 | 0.24 | 15.97 |
| 21 | To 84° C. | 100 | 160 | 100 | 100 | 3300 mg 0.3 wt % Pd/Al$_2$O$_3$ | 1 h 31 min | 2.96 | 67.56 | 17.67 | 0.21 | 14.56 |
| 22 | To 88° C. | 100 | 160 | 100 | 100 | 3300 mg 0.3 wt % Pd/Al$_2$O$_3$ | 1 h 30 min | 2.98 | 68.08 | 16.61 | 0.16 | 15.15 |
| 23 | To 38° C. | 100 | 160 | 100 | 100 | 3300 mg 0.3 wt % Pd/Al$_2$O$_3$ | 2 h 36 min | 3.05 | 69.06 | 13.61 | 0.16 | 17.18 |
| 24 | To 36° C. | 100 | 210 | 100 | 20 | 3300 mg 0.3 wt % Pd/Al$_2$O$_3$ | 2 h 25 min | 3.11 | 77.58 | 5.45 | 0.16 | 16.81 |
| 25 | To 34° C. | 100 | 240 | 100 | 10 | 3300 mg 0.3 wt % Pd/Al$_2$O$_3$ | 5 h 4 min | 3.12 | 83.55 | 1.52 | 0.49 | 14.44 |
| 26 | To 40° C. | 100 | 240 | 100 | 10 | 3300 mg 0.3 wt % Pd/Al$_2$O$_3$ | 3 h 28 min | 3.02 | 84.3 | 6.3 | 0.3 | 9.1 |
| 27 | To 28° C. | 100 | 160 | 100 | 100 | 198 mg 5 wt % Pd/C | 2 h 25 min | 2.95 | 62.9 | 20.4 | 0.3 | 16.4 |
| 28 | To 35° C. | 100 | 160 | 100 | 100 | 2567 mg 0.3 wt % Pd/Al$_2$O$_3$ | 4 h 25 min | 2.96 | 67.0 | 18.3 | 0.1 | 14.6 |
| 29 | To 37° C. | 100 | 160 | 100 | 10 | 3300 mg 0.3 wt % Pd/Al$_2$O$_3$ | 3 h 17 min | 2.98 | 74.2 | 13.6 | 0.2 | 12.0 |
| 30 | To 27° C. | 100 | 160 | 100 | 100 | 1980 mg 0.5 wt % Pd/titanium silicate | 4 h 45 min | 2.9 | 63.6 | 16.9 | 0.1 | 19.2 |

TABLE 6-continued

Examples 16-31

| Ex. | Self-heat | T (° C.) stage 1 | T (° C.) stage 2 | P H$_2$ (psig) stage 1 | P H$_2$ (psig) stage 2 | Catalyst | Run time | Mol. H$_2$ | % monoolefin | % diolefine | % triolefin | % farnesane |
|---|---|---|---|---|---|---|---|---|---|---|---|---|
| 31 | none | 100 | 240 | 100 | 10, 20, 30 | 3300 mg 0.3 wt % Pd/Al$_2$O$_3$ | 10 h 30 min | 3.14 | 79.0 | 3.2 | 0.1 | 17.0 |

Example 32. Staged Hydrogenation in a Fixed Bed Reactor

Sixteen fixed bed reactors operating in parallel (Flowrence® fixed bed reactors, available from Avantium), each having a length of 48 cm and an inner diameter (id) of 2.0 mm, were configured to have two catalyst zones and two heated zones to accomplish a two stage hydrogenation reaction of β-farnesene. Each reactor was oriented vertically and fluid was directed into an inlet at the top of the reactor to flow downwards through the reactor. The catalyst was 0.3 wt % Pd/Al$_2$O$_3$ Pricat™ 309/7 extrudates, available from Johnson Matthey. The extrudates were crushed and sieved to a particle size of 212-425 μm. The feed was 25 vol/vol % β-farnesene in Durasyn® 164 PAO fluid. β-farnesene was supplied by Amyris (>97% pure) and received no further pretreatment before use. Pure hydrogen (no nitrogen diluent) was used. Each reactor was operated in trickle flow mode and configured to have two hydrogenation zones. A first (top) hydrogenation zone begins at the inlet and extends for the top to a maximum distance of 6 cm, depending on quantity of catalyst in the first zone. Each reactor is packed with catalyst in the first zone and is heated to maintain a temperature of 120° C. Below the first zone is an unheated intermediate section packed with inert Zirblast® ceramic beads, containing no catalyst, and extending for 26-43 cm below the top zone, with the length of the unheated intermediate section depending on quantity of catalyst used in the top and bottom zones. The second (bottom) hydrogenation zone begins below the unheated intermediate zone and extends downward for 2-14 cm (depending on quantity of catalyst in second zone), is packed with catalyst and heated to maintain a temperature of 225° C. The bottom two centimeters of the reactor are heated to 225° C. and are packed with inert Zirblast® ceramic beads with no catalyst. A diagram of the reactors is shown in FIG. 6. A factorial design was set up to result in 16 different combinations of top and bottom catalyst loadings as shown in Table 7A.

TABLE 7A

| Reactor | Bottom inert Zirblast® ceramic 225° C. [mass (mg), length (cm)] | Bottom catalyst 225° C. [mass (mg), length (cm)] | Inert Zirblast® ceramic [mass (mg), length (cm)] | Top catalyst 120° C. [mass (mg), length (cm)] |
|---|---|---|---|---|
| 1 | 591, 2.1 | 53, 2.6 | 3115, 41.8 | 0, 0 |
| 2 | 587, 2 | 52, 2.4 | 2956, 39.7 | 25, 1 |
| 3 | 580, 1.9 | 54, 2.2 | 2834, 35.2 | 48, 2.5 |
| 4 | 569, 1.8 | 56, 23.5 | 2611, 35.4 | 103, 4.9 |
| 5 | 576, 1.9 | 130, 6.5 | 2715, 36.4 | 0, 0 |
| 6 | 577, 1.8 | 138, 6.7 | 2616, 35.1 | 25, 1.3 |
| 7 | 583, 1.9 | 132, 6.4 | 2465, 33.2 | 52, 2.5 |
| 8 | 568, 1.5 | 131, 6 | 2252, 28.1 | 126, 5.3 |
| 9 | 586, 2 | 259, 13 | 2144, 28.4 | 0, 0 |
| 10 | 586, 1.9 | 266, 14.1 | 2013, 27.2 | 29, 1.1 |
| 11 | 577, 1.7 | 266, 13.6 | 1916, 25.6 | 64, 2.9 |
| 12 | 581, 1.5 | 259, 11.9 | 1684, 20.8 | 126, 5.3 |
| 13 | 576, 1.5 | 0, 0 | 3270, 43.6 | 0, 0 |
| 14 | 588, 1.9 | 0, 0 | 3145, 42.1 | 30, 1.3 |
| 15 | 581, 1.7 | 0, 0 | 3030, 40.5 | 63, 2.9 |
| 16 | 582, 1.7 | 0, 0 | 2819, 38.3 | 124, 5.8 |

The reaction was operated with a liquid hourly space velocity (LHSV) of 5-55 g-feed/g-catalyst/hour (×¼ for farnesene LHSV) and gas hourly space velocity (GHSV) of 330-3000 Nml/g-catalyst/hour. Hydrogen was supplied in excess at 20-30%. Outlet pressure was 1 atmosphere. Liquid and gas flow rates are adjusted to limit hydrogenation at about 75% if possible. When the top loading of the catalyst is set to zero (reactors 1, 5, 9 and 13), the residence time in the heated zone induces thermal dimerization or polymerization of the farnesene and leads to blocked reactors after about 70 h. Catalyst reactivation at 250° C. did not reopen blocked reactors. Reactors neighboring blocked reactors (2, 4, 10, and 12) were impacted by the blocked reactors. When the bottom loading of the catalyst is set to zero (reactors 13-16), the degree of hydrogenation was less than 40%. Reactors having both top and bottom catalysts can achieve mono-olefin greater than 80% as long as activity is controlled to inhibit excess formation of farnesane. Reactors 3, 6, 7, 8, 11, 14, 15, 16 were running at 24 mg/min 25 vol % farnesene in Durasyn®, 45 Nml/min H$_2$, 40 and 35 Nml/min H$_2$, and a pressure drop less than 5 barg. Reactor 11 experienced pressure oscillations. Reactors 8 and 11 resulted in a degree of hydrogenation that was greater than 80%.

Reactors 3, 6, and 7 are measured under optimized conditions, and detailed experimental conditions and results are provided in Table 7B. Stable operation for these reactors was observed over 500 h. The catalyst could be reactivated at 250° C. under hydrogen. For samples, having degree of hydrogenation ranging from 72%-78%, mono-olefin content (as measured by GC) ranged from about 79-81%, di-olefin content ranged from 11%-2%, and farnesane ranged from 8-18%. Parameters for the GC-MS measurement are as follows. A Thermo Trace-GC with FID detection and DSQ II mass spectroscopy with electric ionization is used. The column type is VF-WaxMS 0.25 mm×0.25 micron×30 m. The start temperature is 60° C. and the hold time is 0 minute. The temperature is ramped to 150° C. at a rate of 6° C./min. and held for 6 minutes, and then ramped to 250° C. at 30° C./min and held for 2 minutes. The injection temperature is 250° C. Split flow at 200 mL/min is used. FID temperature is 275° C. The injection volume is 0.5 microliters. Monoolefins (molecular weight of 210) are observed with retention times at 5.95-6.15, 6.25-7.03, and 7.15 minutes. Di-olefins (molecular weight of 208) are observed with retention times at 7.06 and 7.2-8.35 minutes. Tri-olefins (molecular weight of 206) are observed with retention times at 8.35-9.3 minutes. Tetra-olefins (molecular weight of 204) are observed with retention times of 9.4-9.6 minutes. Farnesane (MW 212) is observed with a retention time of 6.2 minutes. Parameters for GC-FID are as follows. A Thermo Trace-GC with FID detection is used. The column type is VF-WaxMS 0.25 mm×0.25 micron×30 m. The start temperature is 80° C., with a hold time of 0 minutes. The temperature is ramped to 140° C. with a hold time of 0 minutes. Split flow at 80 mL/min is used. The injection temperature is 250° C. The carrier flow rate is 2 mL/min. The FID temperature is 270° C. The injection volume is 0.2 microliters. Mono-olefins are observed with retention times of 5.62-7.02 minutes, di-olefins are observed with retention times of 7.02-9.18 minutes, tri-olefins are observed with retention times of 9.18-11.45 minutes, farnesane is observed at 5.04 minutes with a window of 0.15, tetra-olefins are observed at a retention time of 11.92 minutes with a window of 0.5, and farnesol is observed with a retention time of 13.5 minutes with a window of 0.2.

TABLE 7B

|  | Reactor 3 | Reactor 6 | Reactor 7 |
|---|---|---|---|
| Zone 1 catalyst top loading (mg), 125° C. | 48 | 25 | 52 |
| Zone 2 catalyst bottom loading (mg), 225° C. | 54 | 138 | 132 |
| Total catalyst loading (mg) | 102 | 163 | 187 |
| Average $H_2$ feed flow (Nml/min) | 2.2 | 2.2 | 2.2 |
| LHSV (g-feed/g-cat/h) based on total catalyst loading (×0.25 for farnesene LHSV) | 14-17 | 8-9 | 7.5-8.5 |
| GHSV (Nml/g-cat/h) | 1290 | 810 | 700 |
| Reactor pressure drop (bar) | 2.5 | 1.2 | 1.2 |
| Total catalyst activity (mol farnesene/g-cat/h) | 0.018 (approx.) | 0.011 (approx.) | 0.011 (approx.) |
| Degree of hydrogenation (%) | 71-77 | 77-79 | 78-79 |
| Farnesane (%) | 8.5 | 15.8 | 17.6 |
| Mono-olefin (%) | 79.0 | 81.0 | 79.8 |
| di-olefin (%) | 11.4 | 2.4 | 2.1 |
| Tri-olefin (%) | 0.8 | 0.3 | 0.2 |
| Farnesene (%) | 0.2 | 0.3 | 0.3 |

Example 33. Effect of Hydrogen Pressure on Selectivity

In a first hydrogenation stage, 23.5% hydrogenated β-farnesene is prepared as follows. A reactor (10 L flask) was charged with farnesene (6.9 liter, 5540 g, 27.1 mol) and palladium 5% on alumina (Acros Organics Lot A0217435) (10 g) was added. The mixture was evacuated and flushed with hydrogen 2 times. To the well stirred mixture (with a stirring bar and stirring blade), hydrogen was applied via a balloon (max 1 mol (22 liter) each balloon). Initial the temperature rose to 23° C. and was steady for a long period of time. In order enhance the reaction rate it was decided after 2 days to increase the temperature of the mixture: first to 30° C. and later to 48° C. (internally measured). Overnight the mixture was also stirred in hydrogen atmosphere at room temperature. The reaction progress was monitored by determination of the refraction index. In total the reaction took 10 days. The mixture was filtered through a layer (approximately 2 cm with a diameter of 18 cm) silica (40 mesh) covered by a paper filter with vacuum. The resulting mixture was still blackish turbid and was filtered again through a 3 cm layer silicagel with a diameter of 12 cm with vacuum. Obtained was a clear liquid 5405 g (26.23 mol, 97% yield) with a refractive index of 1.4708. The refractive index of farnesene is approximately 1.4880 and a sample having a degree of hydrogenation of 30% has a refractive index of approximately 1.4700. The composition of the 23.5% hydrogenated β-farnesene is 0.1% farnesane, 0.7% mono-olefin, 2.8% di-olefin, 86.3% tri-olefin, and 10.1% farnesene by GC-FID.

The 23.5% hydrogenated farnesene was distilled and treated with 10 wt % $Al_2O_3$ and 10 wt % silica. 20 g of the pretreated 25% hydrogenated farnesene is loaded into a reactor with 400 mg 0.3 wt % $Pd/Al_2O_3$ (Johnson Matthey 309/7). The reactor is stirred at 1200 rpm. The temperature of the reactor was set to 200° C. The hydrogen pressure was set to about 30 psig. The reaction was allowed to proceed until a total of about 3 equivalents hydrogen were consumed, including the 0.94 equivalents from the first stage. The experiment was repeated for hydrogen pressures of 50, 70, 90 and 110 psig. Results are shown in Table 8, where % of each species is determined by GC-FID as described in Example 2. Using a degree of hydrogenation of slightly less than 75%, a second stage hydrogen pressure of 50 psig and a second stage temperature of 200° C., a composition comprising 85% mono-olefin, <1% di-olefin, and <15% farnesane is achieved.

TABLE 8

| Stage 2 Hydrogen pressure (psig) | % hydrogenation | Reaction time (h) | % monoolefin | % diolefin | % triolefin | % farnesane | Monoolefin:di-olefin |
|---|---|---|---|---|---|---|---|
| 30 | 78.0 | 1.40 | 69.448 | 0.202 | 0.093 | 30.257 | 342.974 |
| 50 | 73.9 | 0.87 | 85.052 | 0.538 | 0.074 | 14.336 | 158.169 |
| 70 | 77.5 | 0.50 | 71.635 | 0.204 | 0.045 | 28.116 | 351.199 |
| 90 | 69.5 | 0.32 | 81.964 | 10.201 | 0.566 | 7.269 | 8.035 |
| 110 | 76.3 | 0.32 | 75.680 | 0.536 | 0.071 | 23.713 | 141.257 |

Example 34. Monitoring Population of Species During Hydrogenation

A first hydrogenation stage is carried out as in Example 33, except that about 30-40% hydrogenation is accomplished in the first stage. Three different second stage hydrogenations are carried out with the temperature being 200° C., with the hydrogen pressure being 2 bar, 1 bar, or 0.5 bar. Samples are taken as the hydrogenation proceeds and species are analyzed as described in Example 32. Results are shown in FIGS. 7A-7C. Second stage hydrogenation conditions for the data shown in FIG. 7A are 200° C., 2 bar hydrogen pressure; second stage hydrogenation conditions for the data shown in FIG. 7B are 200° C., 1 bar hydrogen pressure; second stage hydrogenation conditions for the data shown in FIG. 7C are 200° C., 0.5 bar hydrogen pressure. "X" represents farnesene content, solid squares represent mono-olefin content, solid triangles represent di-olefin content, and solid diamonds represent farnesane content. As shown in FIGS. 7B and 7C, it is possible to stop hydrogenation at less than 75% hydrogenated (e.g., about 74% hydrogenated) and at which mono-olefin content is maximized, di-olefin content has decreased to about 2% or less, and alkane content is about 10%.

What is claimed is:

1. An olefinic feedstock comprising at least about 70-80% hexahydrofarnesene, about 5-10% farnesane, and about 10-20% tetrahydrofarnesene; or at least about 70-80% hexahydrofarnesene, about 5-15% farnesane, and about 5% or less tetrahydrofarnesene.

2. The olefinic feedstock of claim 1, comprising about 10% tetrahydrofarnesene, or about 5% or less tetrahydrofarnesene.

3. The olefinic feedstock of claim 1 further comprising an olefin selected from the group consisting of a $C_5$-$C_{20}$ linear alpha olefin, a $C_5$-$C_{20}$ branched alpha olefin, a $C_5$-$C_{20}$ linear internal olefin, and a $C_5$-$C_{20}$ branched internal olefin.

4. The olefinic feedstock of claim 2, comprising at least about 75% hexahydrofarnesene and about 10% tetrahydrofarnesene; at least about 75% hexahydrofarnesene and about 5% or less tetrahydrofarnesene; or at least about 75% hexahydrofarnesene and about 3% or less tetrahydrofarnesene.

5. The olefinic feedstock of claim 2, comprising less than about 1 ppm sulfur; less than about 1 ppm aromatic compounds; or less than about 1 ppm sulfur and less than about 1 ppm aromatic compounds.

* * * * *